United States Patent
Colley et al.

(10) Patent No.: US 11,661,415 B2
(45) Date of Patent: *May 30, 2023

(54) PROCESS FOR PREPARING A COMPOUND USEFUL TO TREAT MYCOSES

(71) Applicant: PULMOCIDE LIMITED, London (GB)

(72) Inventors: Thomas Christopher Colley, London (GB); Kazuhiro Ito, London (GB); Garth Rapeport, London (GB); Peter Strong, London (GB); Peter John Murray, London (GB); Stuart Thomas Onions, Nottinghamshire (GB); Mihiro Sunose, Nottinghamshire (GB)

(73) Assignee: PULMOCIDE LIMITED, London (GB)

(*) Notice: Subject to any disclaimer, the term of this patent is extended or adjusted under 35 U.S.C. 154(b) by 270 days.

This patent is subject to a terminal disclaimer.

(21) Appl. No.: 17/089,441

(22) Filed: Nov. 4, 2020

(65) Prior Publication Data

US 2021/0048874 A1    Feb. 18, 2021

Related U.S. Application Data

(63) Continuation of application No. 16/849,476, filed on Apr. 15, 2020, now Pat. No. 10,858,345, which is a continuation of application No. 16/569,128, filed on Sep. 12, 2019, now Pat. No. 10,662,179, which is a continuation of application No. 16/422,062, filed on May 24, 2019, now Pat. No. 10,450,304, which is a continuation of application No. 16/139,591, filed on Sep. 24, 2018, now Pat. No. 10,344,022, which is a continuation of application No. 15/524,505, filed as
(Continued)

(30) Foreign Application Priority Data

Dec. 5, 2014 (EP) ..................... 14196662

(51) Int. Cl.
| | |
|---|---|
| *C07D 405/06* | (2006.01) |
| *G06F 1/3234* | (2019.01) |
| *G11C 11/4074* | (2006.01) |
| *C07D 405/00* | (2006.01) |
| *A61K 31/496* | (2006.01) |
| *A61K 45/06* | (2006.01) |
| *C07D 405/14* | (2006.01) |

(52) U.S. Cl.
CPC .......... *C07D 405/06* (2013.01); *A61K 31/496* (2013.01); *A61K 45/06* (2013.01); *C07D 405/00* (2013.01); *C07D 405/14* (2013.01); *G06F 1/3268* (2013.01); *G11C 11/4074* (2013.01)

(58) Field of Classification Search
CPC .................................................. C07D 405/00
See application file for complete search history.

(56) References Cited

U.S. PATENT DOCUMENTS

| | | | |
|---|---|---|---|
| 5,039,676 | A | 8/1991 | Saksena et al. |
| 5,486,625 | A | 1/1996 | Leong et al. |
| 5,714,490 | A | 2/1998 | Saksena et al. |
| 10,093,659 | B2 | 10/2018 | Sunose et al. |
| 10,106,531 | B2 | 10/2018 | Colley et al. |

(Continued)

FOREIGN PATENT DOCUMENTS

| | | |
|---|---|---|
| EP | 0228125 B1 | 3/1992 |
| EP | 0957101 A1 | 11/1999 |

(Continued)

OTHER PUBLICATIONS

Jen; Ear Nose Throat J. 2004, 83, 692, 694-695. (Year: 2004).*

(Continued)

*Primary Examiner* — Daniel R Carcanague
(74) *Attorney, Agent, or Firm* — Birch, Stewart, Kolasch & Birch, LLP

(57) ABSTRACT

A process for preparing a compound of formula (II):

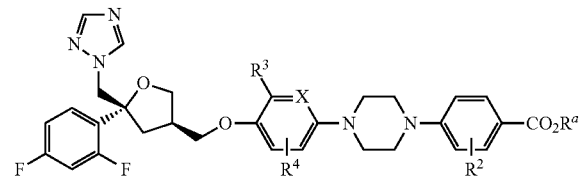

(II)

includes reacting a compound of formula (VIII):

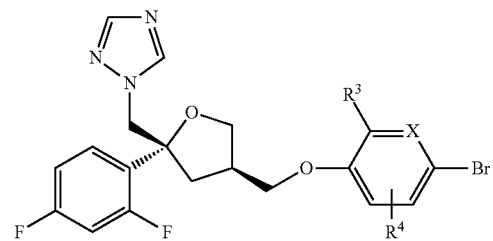

(VIII)

with a compound of formula (XIV):

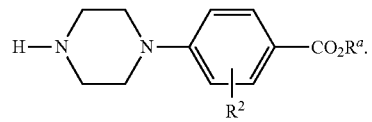

(XIV)

20 Claims, 1 Drawing Sheet

Related U.S. Application Data application No. PCT/GB2015/053733 on Dec. 4, 2015, now Pat. No. 10,106,531.

(56) References Cited

U.S. PATENT DOCUMENTS

| | | |
|---|---|---|
| 10,344,022 B2 | 7/2019 | Colley et al. |
| 10,487,073 B2 | 11/2019 | Sunose et al. |
| 2017/0037035 A1 | 2/2017 | Sunose et al. |
| 2020/0031809 A1 | 1/2020 | Sunose et al. |
| 2020/0399253 A1 | 12/2020 | Sunose et al. |

FOREIGN PATENT DOCUMENTS

| | | |
|---|---|---|
| WO | WO 89/04829 A1 | 6/1989 |
| WO | WO 95/17407 A1 | 6/1995 |
| WO | WO 96/38443 A1 | 12/1996 |
| WO | WO 02/080678 A1 | 10/2002 |
| WO | WO 2013/036866 A1 | 3/2013 |
| WO | WO 2016/087878 A1 | 6/2016 |

OTHER PUBLICATIONS

Posaconazole Oral Suspension, Product Information, Dec. 2008. 38 Pages. (Year: 2008).*

Joshi; Journal of Pharmaceutical Science and Technology 2011, 3, 651-681. (Year: 2011).*

Bowyer, et al.—Pest Management Science 70 (2014) 2: 173-178—"Environmental fungicides and triazole resistance in Aspergillus".

Colley, T. et al; Antimicrob. Agents and Chem., (2017) 61 (5), 1-14—"In Vitro and In Vivo Antifungal Profile of a Novel and Long-Acting Inhaled Azole, PC945, on Aspergillus fumigatus Infection".

Gregson, et al.—Antimicrobial Agents and Chem. (2013) 57 (11) 5778-5780—In Vitro Susceptibility of Aspergillus fumigatus . . . .

Hepperle, et al.—Tetrahedron Letters 43 (2002) 18: 3359-3363—"Mono N-arylation of piperazine(III): metal-catalyzed N-arylation and its application . . . ".

Kimura, G. et al; Antimicrob. Agents and Chem., (2017) 61 (9), 1-13—"In Vivo Biomarker Analysis of the Effects of Intranasally Dosed PC945, a Novel Antifungal Triazole, on Aspergillus fumigatus Infection in Immunocompromised Mice".

Pfaller, et al.—J. of Clin. Microbiology (2009) 47 (10) 3142-3146—"Wild-Type MIC Distribution and Epidemiological Cutoff Values for Aspergillus fumigatus . . . ".

Saksena, et al.—Tetrahedron Letters 45 (2004) 44: 8249-8251—"Stereoselective Grignard additions to N-formyl hydrazone: a concise synthesis of . . . ".

Zacchino, et al—Expert Opinion Ther. Patents (2014) 24(3) 323-338—Novel antifungal agents: a patent review (2011-present).

* cited by examiner

PROCESS FOR PREPARING A COMPOUND USEFUL TO TREAT MYCOSES

CROSS-REFERENCE TO RELATED APPLICATIONS

This application is a Continuation of co-pending U.S. application Ser. No. 16/849,476 filed on Apr. 15, 2020, which is a Continuation of co-pending U.S. application Ser. No. 16/569,128 filed on Sep. 12, 2019, now U.S. Pat. No. 10,662,179, issued May 26, 2020, which is a Continuation of co-pending U.S. application Ser. No. 16/422,062 filed on May 24, 2019, now U.S. Pat. No. 10,450,304, issued Oct. 22, 2019, which is a Continuation of U.S. application Ser. No. 16/139,591 filed on Sep. 24, 2018, now U.S. Pat. No. 10,344,022, issued Jul. 9, 2019, which is a Continuation of U.S. application Ser. No. 15/524,505, filed on May 4, 2017, now U.S. Pat. No. 10,106,531, issued Oct. 23, 2018, which is a National Phase of PCT International Application No. PCT/GB2015/053733 filed on Dec. 4, 2015, which claims priority under 35 U.S.C. § 119(a) to Patent Application No. 14196662.2 filed in Europe on Dec. 5, 2014. All of the above applications are hereby expressly incorporated by reference into the present application.

FIELD OF THE INVENTION

This invention relates to a compound useful in the treatment of mycoses, compositions containing it and its use in therapy.

BACKGROUND OF THE INVENTION

The incidence of fungal infections has increased substantially over the past two decades and invasive forms are leading causes of morbidity and mortality, especially amongst immunocompromised or immunosuppressed patients. Disseminated candidiasis, pulmonary aspergillosis, and emerging opportunistic fungi are the most common agents producing these serious mycoses. It is a particular feature of fungi that they are able to generate an extracellular matrix (ECM) that binds them together and allows them to adhere to their in vitro or in vivo substrates. These biofilms serve to protect them against the hostile environments of the host immune system and to resist antimicrobial killing (Kaur and Singh, 2013).

Pulmonary aspergillosis can be segmented into those patients suffering with non-invasive disease versus those with an invasive condition. A further sub-division is used to characterise patients who exhibit an allergic component to aspergillosis (known as ABPA; allergic bronchopulmonary aspergillosis) compared with those that do not. The factors precipitating pulmonary aspergillosis may be acute, such as exposure to high doses of immuno-suppressive medicines or to intubation in an intensive care unit. Alternatively, they may be chronic, such as a previous infection with TB (Denning et al., 2011a). Chronic lung infections with *aspergillus* can leave patients with extensive and permanent lung damage, requiring lifetime treatment with oral azole drugs (Limper et al., 2011).

A growing body of research suggests that *aspergillus* infection may play an important role in clinical asthma (Chishimba et al., 2012; Pasqualotto et al., 2009). Furthermore, recently published work has correlated *aspergillus* infection with poorer clinical outcomes in patients with COPD (Bafadhel et al., 2013). Similarly cross-sectional studies have shown associations between the presence of *Aspergillus* spp. and *Candida* spp. in the sputum and worsened lung function (Chotirmall et al., 2010; Agbetile et al., 2012).

Invasive aspergillosis (IA) exhibits high mortality rates in immunocompromised patients, for example, those undergoing allogenic stem cell transplantation or solid organ transplants (such as lung transplants). The first case of IA reported in an immunocompromised patient occurred in 1953. This event was concurrent with the introduction of corticosteroids and cytotoxic chemotherapy into treatment regimens (Rankin, 1953). Invasive aspergillosis is a major concern in the treatment of leukaemia and other haematological malignancies given its high incidence and associated mortality. Death rates usually exceed 50% (Lin et al., 2001) and long term rates can reach 90% in allogeneic hematopoietic stem cell transplantation recipients, despite the availability of oral triazole medicines (Salmeron et al., 2012). In patients undergoing solid organ transplantation (particularly of the lung), the use of high doses of steroids leaves patients vulnerable to infection (Thompson and Patterson, 2008) which is a serious problem. The disease has also appeared in less severely immunocompromised patient populations. These include those suffering with underlying COPD or cirrhosis, patients receiving high dose steroids, and individuals fitted with central venous catheters or supported by mechanical ventilation (Dimopoulos et al., 2012).

Existing anti-fungal medicines are predominantly dosed either orally or systemically. These commonly exploited routes of delivery are poor for treating lung airways infections, since drug concentrations achieved at the site of infection tend to be lower than those in organs. This is especially so for the liver, which is a site of toxicity: up to 15% of patients treated with voriconazole suffer raised transaminase levels (Levin et al., 2007; Lat and Thompson, 2011). Exposure of the liver also results in significant drug interactions arising from the inhibition of hepatic P450 enzymes (Jeong, et al., 2009; Wexler et al., 2004).

Furthermore, the widespread use of triazoles, both in the clinic and in agriculture has led to a growing and problematic emergence of resistant mycoses in some locations (Denning et al., 2011b; Bowyer and Denning, 2014).

It is clearly evident that an urgent medical need exists for novel anti-fungal medicines that deliver improved efficacy and better systemic tolerability profiles.

SUMMARY OF THE INVENTION

In a first aspect, the invention provides compounds of formula (I), (I)

[Chemical structure of formula (I) showing a triazole group connected through a tetrahydrofuran ring bearing a 2,4-difluorophenyl group, linked via an oxygen to a pyridine/benzene ring with substituents $R^3$, $R^4$ and X, connected to a piperazine, then to another aromatic ring with $R^2$, linked via a carboxamide to a further aromatic ring bearing R, $R^{1a}$, $R^{1b}$ and Y]

wherein:
R represents hydrogen, halo, cyano, $C_{1-4}$ haloalkyl, $C_{1-4}$ haloalkoxy, or $SO_2NR^5R^6$;
$R^{1a}$ and $R^{1b}$ independently represent hydrogen or halo;
$R^2$ represents hydrogen, halo, cyano, $C_{1-4}$ alkyl, $C_{1-4}$ alkoxy or $C_{1-4}$ haloalkoxy;
$R^3$ represents, halo, cyano, $C_{1-4}$ alkyl, or $C_{1-4}$ hydroxyalkyl;
$R^4$ represents, hydrogen or $C_{1-4}$ alkyl;
X represents CH or N;
Y represents CH or N;
$R^5$ and $R^6$ independently represent hydrogen or $C_{1-4}$ alkyl
and pharmaceutically acceptable salts thereof (sometimes referred to hereinafter as "compounds of the invention" or "compounds of the disclosure").

Biological data disclosed herein below reveals that the compounds of the invention are potent inhibitor of *Aspergillus fumigatus* growth in in vitro assays. In immunosuppressed mice compounds of the invention demonstrated potent inhibition of *Aspergillus fumigatus* infections. Other desirable properties of compounds of the invention are described herein.

BRIEF DESCRIPTION OF THE FIGURES

In FIGS. 1-3, the symbol *** indicates significance with P<0.001.

DETAILED DESCRIPTION OF THE INVENTION

Figure 1:
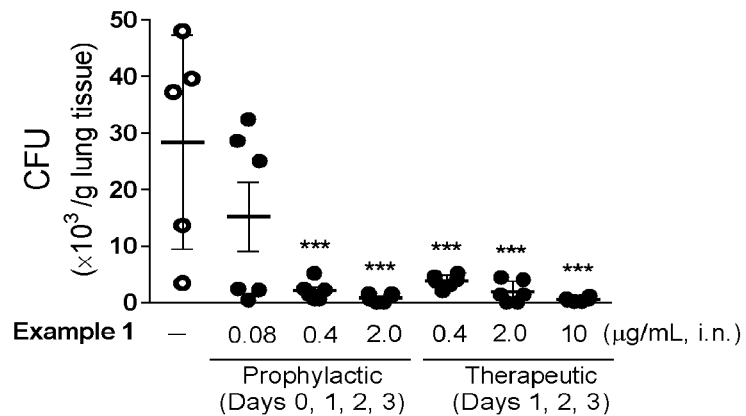
FIG. 1 displays the effects of prophylactic and therapeutic treatment with compound Example 1 on CFU in the lungs of *Aspergillus fumigatus* infected, immuno-compromised, neutropenic mice.

Alkyl groups may be branched or straight chain. $C_{1-4}$ alkyl groups may for example represent $C_{1-3}$ alkyl or $C_{1-2}$ alkyl. Exemplary alkyl groups include methyl, ethyl, n-propyl, i-propyl, n-butyl, t-butyl and $CH_2CHMe_2$. In one embodiment alkyl refers to straight chain alkyl.

Alkoxy as used herein means-Oalkyl and includes straight or branched chain alkoxy, for example methoxy, ethoxy, propoxy, butoxy.

Hydroxyalkyl means alkyl with a hydroxyl substituent in any position. Examples include hydroxymethyl, 2-hydroxyethyl, 3-hydroxy-n-propyl and 4-hydroxy-n-butyl.

Halogens may suitably be Br, Cl or F, especially Cl or F, particularly F.

In one embodiment there is provided a pharmaceutically acceptable salt of the compound of the invention.

The compounds of the disclosure include those wherein the atom specified is a naturally occurring or non-naturally occurring isotope. In one embodiment the isotope is a stable isotope. Thus the compounds of the disclosure include, for example those containing one or more deuterium atoms in place of hydrogen atoms and the like.

The disclosure also extends to all polymorphic forms of the compounds herein defined.

The disclosure also extends to all solvate of the compounds herein defined. Examples of solvates include hydrates.

Suitably R represents H, F, CN, $OCHF_2$, $OCF_3$, $SO_2NH_2$, $SO_2NHMe$, $SO_2NMe_2$ or Cl, especially F or CN, more preferably F.
Suitably $R^{1a}$ represents H, F or Cl, especially H.
Suitably $R^{1b}$ represents H or F, especially H.
Suitably $R^2$ represents H, Me or OMe, especially H.
Suitably $R^3$ represents Me, CN, Cl, $CH_2OH$ or F, especially Me.
Suitably $R^4$ represents H or Me, especially H.
Suitably $R^5$ represents H or Me.
Suitably $R^6$ represents H or Me.
Suitably $NR^5R^6$ represents $NH_2$, NHMe or $NMe_2$.
Suitably X represents CH or N, especially CH.
Suitably Y represents CH (which carbon atom may optionally be substituted by R, $R^{1a}$, or $R^{1b}$ for example by F) or N, especially CH.
Suitably $R^{1a}$ and $R^{1b}$ each represent H and R represents F, CN, $OCHF_2$, $OCF_3$, $SO_2NH_2$, $SO_2NHMe$, $SO_2NMe_2$, or Cl, especially $R^{1a}$ and $R^{1b}$ represent H and R represents F or CN, more preferably $R^{1a}$ and $R^{1b}$ represent H and R represents F.
Alternatively suitably $R^{1a}$ represents F, $R^{1b}$ represents H and R represents F or $OCHF_2$, for example, $R^{1a}$ represents F, $R^{1b}$ represents H and R represents F.
Alternatively suitably $R^{1a}$ represents Cl, $R^{1b}$ represents H and R represents F.
Suitably $R^4$ represents H and $R^3$ represents Me, CN, Cl, $CH_2OH$ or F, especially $R^4$ represents H and $R^3$ represents Me.
Alternatively suitably $R^4$ represents Me and $R^3$ represents Me.

Suitably Y represents CH, $R^{1a}$ and $R^{1b}$ each represent H and R is in the 3-position or 4-position, especially the 4-position.

Alternatively suitably Y represents CH, $R^{1b}$ represents H and R and $R^{1a}$ are in the 2,4-positions, 3,4-positions, 2,5-positions or 3,5-positions, especially the 2,4-positions.

Alternatively suitably Y represents N, $R^{1a}$ and $R^{1b}$ each represent H and R is in the 4-position, 5-position or 6-position, especially the 5-position.

Suitably Y represents CH and R, $R^{1a}$ and $R^{1b}$ are in the 2, 4 and, 6-positions.

Suitably $R^2$ is located ortho to the nitrogen of the piperazinyl substituent. Alternatively, $R^2$ is located meta to the nitrogen of the piperazinyl substituent.

Suitably $R^4$ is located ortho to the oxygen of the ether substituent.

Suitably the aromatic moiety comprising Y represents 4-fluorophenyl, 3-fluorophenyl, 2,4-difluorophenyl, 2,5-difluorophenyl, 3,4-difluorophenyl, 3,5-difluorophenyl, 4-cyanophenyl, 3-cyanophenyl, 4-difluoromethoxyphenyl, 4-(trifluoromethoxy)phenyl, 4-sulfamoylphenyl, 4-(N-methylsulfamoyl)phenyl, 4-(N—N-dimethylsulfamoyl) phenyl, 4-cyano-2-fluorophenyl, 4-(difluoromethoxy)-3-fluorophenyl, 4-chloro-2-fluorophenyl, 4-chloro-3-fluorophenyl, 2,4,6-trifluorophenyl, 5-fluoropyridin-2-yl, 5-cyanopyridin-2-yl, 6-cyanopyridin-2-yl, 4-cyanopyridin-2-yl, 5-(trifluoromethoxy)pyridin-2-yl or 5-chloropyridin-2-yl, especially 4-fluorophenyl or 4-cyanophenyl, more preferably 4-fluorophenyl.

In an embodiment, the compound of formula (I) is selected from:

4-(4-(4-(((3R,5R)-5-((1H-1,2,4-triazol-1-yl)methyl)-5-(2,4-difluorophenyl)tetrahydrofuran-3-yl) methoxy)-3-methylphenyl)piperazin-1-yl)-N-(4-fluorophenyl)benzamide;

4-(4-(4-(((3R,5R)-5-((1H-1,2,4-triazol-1-yl)methyl)-5-(2,4-difluorophenyl)tetrahydrofuran-3-yl) methoxy)-3-methylphenyl)piperazin-1-yl)-N-(2,4-difluorophenyl)benzamide;

4-(4-(5-(((3R,5R)-5-((1H-1,2,4-triazol-1-yl)methyl)-5-(2,4-difluorophenyl)tetrahydrofuran-3-yl) methoxy)-6-methylpyridin-2-yl)piperazin-1-yl)-N-(4-fluorophenyl)benzamide;

4-(4-(4-(((3R,5R)-5-((1H-1,2,4-triazol-1-yl)methyl)-5-(2,4-difluorophenyl)tetrahydrofuran-3-yl) methoxy)-3-cyanophenyl)piperazin-1-yl)-N-(4-fluorophenyl)benzamide;

4-(4-(4-(((3R,5R)-5-((1H-1,2,4-triazol-1-yl)methyl)-5-(2,4-difluorophenyl)tetrahydrofuran-3-yl) methoxy)-2,5-dimethylphenyl)piperazin-1-yl)-N-(4-fluorophenyl)benzamide;

4-(4-(4-(((3R,5R)-5-((1H-1,2,4-triazol-1-yl)methyl)-5-(2,4-difluorophenyl)tetrahydrofuran-3-yl) methoxy)-3-methylphenyl)piperazin-1-yl)-N-(5-fluoropyridin-2-yl)benzamide;

4-(4-(5-(((3R,5R)-5-((1H-1,2,4-triazol-yl)methyl)-5-(2,4-difluorophenyl)tetrahydrofuran-3-yl) methoxy)-3-methylphenyl)piperazin-1-yl)-N-(5-cyanopyridin-2-yl)benzamide;

4-(4-(4-(((3R,5R)-5-((1H-1,2,4-triazol-1-yl)methyl)-5-(2,4-difluorophenyl)tetrahydrofuran-3-yl) methoxy)-3-methylphenyl)piperazin-1-yl)-N-(3-cyanophenyl)benzamide;

4-(4-(4-(((3R,5R)-5-((1H-1,2,4-triazol-yl)methyl)-5-(2,4-difluorophenyl)tetrahydrofuran-3-yl) methoxy)-3-methylphenyl)piperazin-1-yl)-N-(4-cyanophenyl)benzamide;

4-(4-(4-(((3R,5R)-5-((1H-1,2,4-triazol-yl)methyl)-5-(2,4-difluorophenyl)tetrahydrofuran-3-yl) methoxy)-3-chlorophenyl)piperazin-1-yl)-N-(4-cyanophenyl)benzamide;

4-(4-(4-(((3R,5R)-5-((1H-1,2,4-triazol-1-yl)methyl)-5-(2,4-difluorophenyl)tetrahydrofuran-3-yl) methoxy)-3,5-dimethylphenyl)piperazin-1-yl)-N-(4-cyanophenyl)benzamide;

4-(4-(4-(((3R,5R)-5-((1H-1,2,4-triazol-1-yl)methyl)-5-(2,4-difluorophenyl)tetrahydrofuran-3-yl) methoxy)-3-methylphenyl)piperazin-1-yl)-N-(4-difluoromethoxyphenyl)benzamide;

4-(4-(5-(((3R,5R)-5-((1H-1,2,4-triazol-1-yl)methyl)-5-(2,4-difluorophenyl)tetrahydrofuran-3-yl) methoxy)-3-methylphenyl)piperazin-1-yl)-N-(4-(trifluoromethoxy)phenyl)benzamide;

4-(4-(4-(((3R,5R)-5-((1H-1,2,4-triazol-1-yl)methyl)-5-(2,4-difluorophenyl)tetrahydrofuran-3-yl) methoxy)3-methylphenyl)piperazin-1-yl)-N-(3-fluorophenyl)benzamide;

4-(4-(4-(((3R,5R)-5-((1H-1,2,4-triazol-1-yl)methyl)-5-(2,4-difluorophenyl)tetrahydrofuran-3-yl) methoxy)-3,5-dimethylphenyl)piperazin-1-yl)-N-(4-fluorophenyl)benzamide;

4-(4-(4-(((3R,5R)-5-((1H-1,2,4-triazol-1-yl)methyl)-5-(2,4-difluorophenyl)tetrahydrofuran-3-yl) methoxy)-3-hydroxymethylphenyl)piperazin-1-yl)-N-(4-fluorophenyl)benzamide;

4-(4-(4-(((3R,5R)-5-((1H-1,2,4-triazol-1-yl)methyl)-5-(2,4-difluorophenyl)tetrahydrofuran-3-yl) methoxy)-3-fluorophenyl)piperazin-1-yl)-N-(4-fluorophenyl)benzamide;

4-(4-(4-(((3R,5R)-5-((1H-1,2,4-triazol-1-yl)methyl)-5-(2,4-difluorophenyl)tetrahydrofuran-3-yl) methoxy)-3-chlorophenyl)piperazin-1-yl)-N-(4-fluorophenyl)benzamide;

4-(4-(4-(((3R,5R)-5-((1H-1,2,4-triazol-1-yl)methyl)-5-(2,4-difluorophenyl)tetrahydrofuran-3-yl) methoxy)-3-methylphenyl)piperazin-1-yl)-N-(4-sulfamoylphenyl)benzamide;

4-(4-(4-(((3R,5R)-5-((1H-1,2,4-triazol-1-yl)methyl)-5-(2,4-difluorophenyl)tetrahydrofuran-3-yl) methoxy)-3-methylphenyl)piperazin-1-yl)-N-(4-(N-methylsulfamoyl)phenyl)benzamide;

4-(4-(4-(((3R,5R)-5-((1H-1,2,4-triazol-1-yl)methyl)-5-(2,4-difluorophenyl)tetrahydrofuran-3-yl)methoxy)3-methylphenyl)piperazin-1-yl)-N-(4-(N,N-dimethylsulfamoylphenyl)benzamide;

4-(4-(4-(((3R,5R)-5-((1H-1,2,4-triazol-1-yl)methyl)-5-(2,4-difluorophenyl)tetrahydrofuran-3-yl) methoxy)-3-fluorophenyl)piperazin-1-yl)-N-(4-sulfamoylphenyl)benzamide;

4-(4-(4-(((3R,5R)-5-((1H-1,2,4-triazol-1-yl)methyl)-5-(2,4-difluorophenyl)tetrahydrofuran-3-yl) methoxy)-3-methylphenyl)piperazin-1-yl)-N-(4-cyano-2-fluorophenyl)benzamide;

4-(4-(4-(((3R,5R)-5-((1H-1,2,4-triazol-1-yl)methyl)-5-(2,4-difluorophenyl)tetrahydrofuran-3-yl) methoxy)3-fluorophenyl)piperazin-1-yl)-N-(4-cyano-2-fluorophenyl)benzamide;

4-(4-(4-(((3R,5R)-5-((1H-1,2,4-triazol-1-yl)methyl)-5-(2,4-difluorophenyl)tetrahydrofuran-3-yl) methoxy)-3-methylphenyl)piperazin-1-yl)-N-(4-(difluoromethoxy)-3-fluorophenyl)benzamide;

4-(4-(4-(((3R,5R)-5-((1H-1,2,4-triazol-1-yl)methyl)-5-(2,4-difluorophenyl)tetrahydrofuran-3-yl) methoxy)-3-methylphenyl)piperazin-1-yl)-N-(2,5-difluorophenyl)benzamide;

4-(4-(4-(((3R,5R)-5-((1H-1,2,4-triazol-1-yl)methyl)-5-(2,4-difluorophenyl)tetrahydrofuran-3-yl) methoxy)-3-methylphenyl)piperazin-1-yl)-N-(3,4-difluorophenyl)benzamide;

4-(4-(4-(((3R,5R)-5-((1H-1,2,4-triazol-1-yl)methyl)-5-(2,4-difluorophenyl)tetrahydrofuran-3-yl) methoxy)3-methylphenyl)piperazin-1-yl)-N-(3,5-difluorophenyl)benzamide;

4-(4-(4-(((3R,5R)-5-((1H-1,2,4-triazol-1-yl)methyl)-5-(2,4-difluorophenyl)tetrahydrofuran-3-yl) methoxy)-3-methylphenyl)piperazin-1-yl)-N-(4-chloro-2-fluorophenyl)benzamide;

4-(4-(4-(((3R,5R)-5-((1H-1,2,4-triazol-1-yl)methyl)-5-(2,4-difluorophenyl)tetrahydrofuran-3-yl) methoxy)-3-methylphenyl)piperazin-1-yl)-N-(4-chloro-3-fluorophenyl)benzamide;

4-(4-(4-(((3R,5R)-5-((1H-1,2,4-triazol-1-yl)methyl)-5-(2,4-difluorophenyl)tetrahydrofuran-3-yl) methoxy)3-methylphenyl)piperazin-1-yl)-N-(2,4,6-trifluorophenyl)benzamide;

4-(4-(4-(((3R,5R)-5-((1H-1,2,4-triazol-1-yl)methyl)-5-(2,4-difluorophenyl)tetrahydrofuran-3-yl) methoxy)-3-methylphenyl)piperazin-1-yl)-N-(4-fluorophenyl)-3-methylbenzamide;

4-(4-(4-(((3R,5R)-5-((1H-1,2,4-triazol-1-yl)methyl)-5-(2,4-difluorophenyl)tetrahydrofuran-3-yl) methoxy)-3-methylphenyl)piperazin-1-yl)-N-(4-fluorophenyl)-2-methylbenzamide;

4-(4-(4-(((3R,5R)-5-((1H-1,2,4-triazol-1-yl)methyl)-5-(2,4-difluorophenyl)tetrahydrofuran-3-yl) methoxy)3-methylphenyl)piperazin-1-yl)-N-(4-fluorophenyl)-3-methoxybenzamide;

4-(4-(4-(((3R,5R)-5-((1H-1,2,4-triazol-1-yl)methyl)-5-(2,4-difluorophenyl)tetrahydrofuran-3-yl) methoxy)-3-methylphenyl)piperazin-1-yl)-N-(4-fluorophenyl)-2-methoxybenzamide;

4-(4-(4-(((3R,5R)-5-((1H-1,2,4-triazol-1-yl)methyl)-5-(2,4-difluorophenyl)tetrahydrofuran-3-yl) methoxy)-3-methylphenyl)piperazin-1-yl)-N-(6-cyanopyridin-2-yl)benzamide;

4-(4-(4-(((3R,5R)-5-((1H-1,2,4-triazol-1-yl)methyl)-5-(2,4-difluorophenyl)tetrahydrofuran-3-yl) methoxy)-3-methylphenyl)piperazin-1-yl)-N-(4-cyanopyridin-2-yl)benzamide;

4-(4-(4-(((3R,5R)-5-((1H-1,2,4-triazol-1-yl)methyl)-5-(2,4-difluorophenyl)tetrahydrofuran-3-yl) methoxy)-3-hydroxymethylphenyl)piperazin-1-yl)-N-(5-cyanopyridin-2-yl)benzamide;

4-(4-(4-(((3R,5R)-5-((1H-1,2,4-triazol-1-yl)methyl)-5-(2,4-difluorophenyl)tetrahydrofuran-3-yl) methoxy)-3-methylphenyl)piperazin-1-yl)-N-(5-(trifluoromethoxy)pyridin-2-yl)benzamide;

4-(4-(4-(((3R,5R)-5-((1H-1,2,4-triazol-1-yl)methyl)-5-(2,4-difluorophenyl)tetrahydrofuran-3-yl) methoxy)-3-fluorophenyl)piperazin-1-yl)-N-(5-fluoropyridin-2-yl)benzamide;

4-(4-(4-(((3R,5R)-5-((1H-1,2,4-triazol-1-yl)methyl)-5-(2,4-difluorophenyl)tetrahydrofuran-3-yl) methoxy)-3-methylphenyl)piperazin-1-yl)-N-(5-chloropyridin-2-yl)benzamide;

4-(4-(4-(((3R,5R)-5-((1H-1,2,4-triazol-1-yl)methyl)-5-(2,4-difluorophenyl)tetrahydrofuran-3-yl) methoxy)6-methylpyridin-2-yl)piperazin-1-yl)-N-(5-cyanopyridin-2-yl)benzamide;

4-(4-(4-(((3R,5R)-5-((1H-1,2,4-triazol-1-yl)methyl)-5-(2,4-difluorophenyl)tetrahydrofuran-3-yl) methoxy)-6-methylpyridin-2-yl)piperazin-1-yl)-N-(5-fluoropyridin-2-yl)benzamide;

and pharmaceutically acceptable salts thereof.

In an embodiment, the compound of formula (I) is not: 4-(4-(4-(((3R,5R)-5-((1H-1,2,4-triazol-1-yl)methyl)-5-(2,4-difluorophenyl)tetrahydrofuran-3-yl) methoxy)-3-methylphenyl)piperazin-1-yl)-N-(4-fluorophenyl) benzamide or a pharmaceutically acceptable salt thereof.

The compounds of the invention may be prepared from commercially available starting materials by the non-limiting synthetic methodologies depicted below (Schemes 1-3).

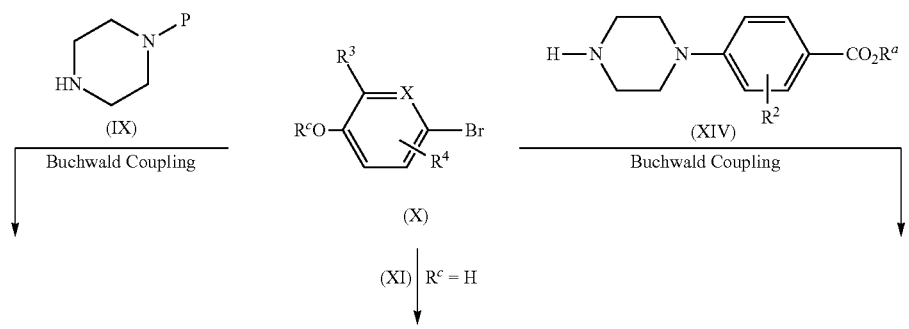

Scheme 1

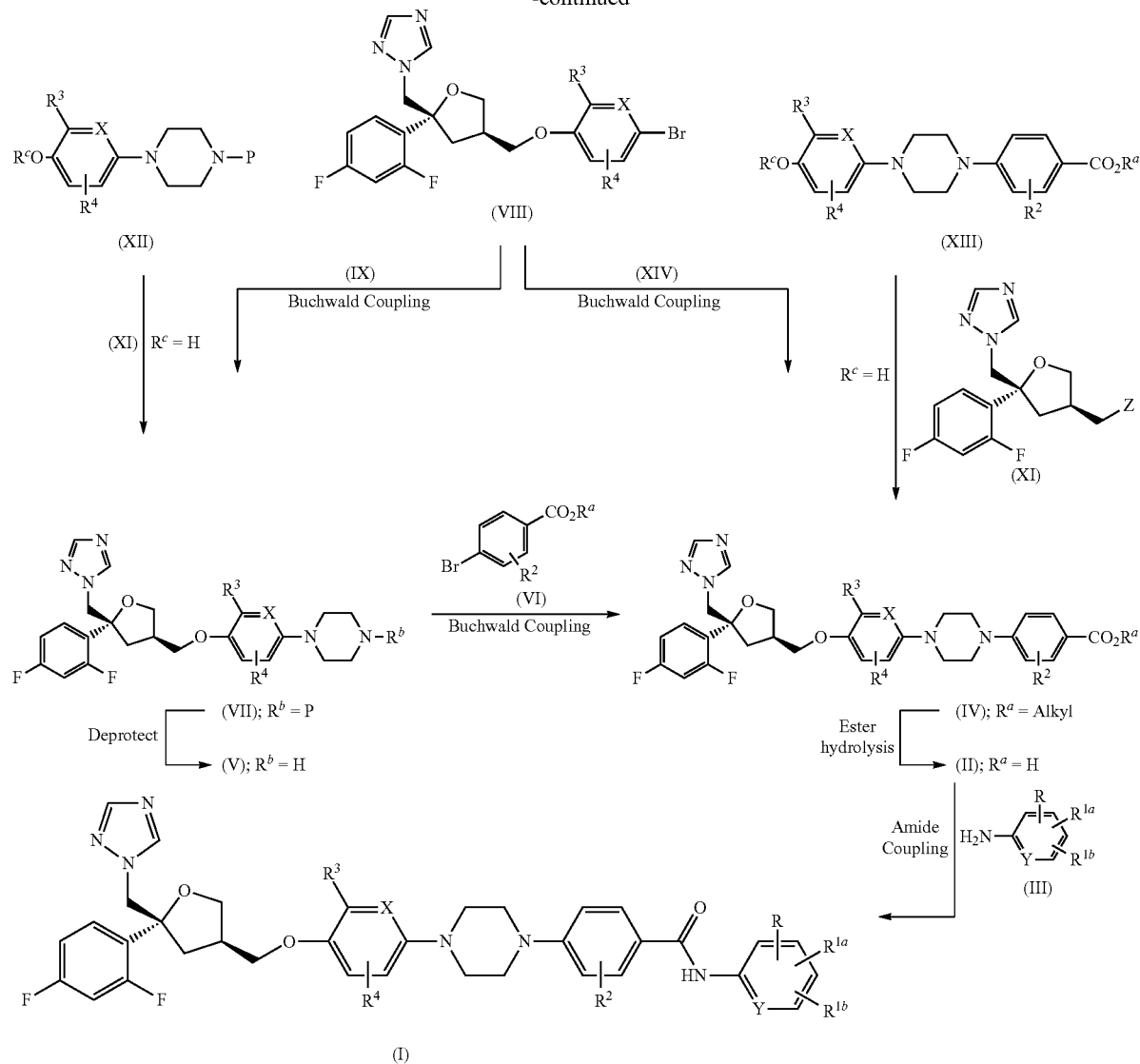

Thus compounds of formula (I) may be obtained by a general process (Scheme 1) whereby a benzoic acid precursor (II), or a suitably protected derivative thereof, is reacted with an activating agent, to generate a reactive, electrophilic carboxylic acid derivative, followed by subsequent reaction with an amine of formula (III), or a suitably protected derivative thereof. It will be understood by persons skilled in the art that, in some instances, the activated carboxylic acid derivative, such as an acid chloride, may be isolated or in other cases may be a transient intermediate that is not isolated, but generated in situ and used directly. Reagents suitable for the activation of the carboxylate group include carbonyl diimidazole, 1-chloro-N,N,2-trimethylprop-1-en-1-amine and a wide selection of peptide coupling agents such as benzotriazol-1-yloxytripyrrolidinophosphonium hexafluorophosphate (PyBOP®), N-(3-dimethylaminopropyl)-W-ethylcarbodiimide hydrochloride (EDCl.HCl) and the like. Such reactions are conveniently carried out in a non-polar, aprotic solvent, such as DCM or, in some cases, polar, non protic solvents such as pyridine. The resulting amides may be generated at or below ambient temperature, such as RT or may be formed at elevated temperatures for example 60° C. A review of methodologies for the preparation of amides is covered in: '*Amide bond formation and peptide coupling*' Montalbetti, C. A. G. N. and Falque, V. *Tetrahedron*, 2005, 61, 10827-10852. The compounds of formula (I) are revealed, in those instances wherein one or more protective groups have been employed by appropriate deprotection steps.

The intermediates of formula (II) may be derived by a noble metal-mediated bond forming process, such as a Buchwald coupling reaction, between a piperazine derivative of formula (V) and a 4-bromobenzoate of formula (VI) to provide, in the first instance, the corresponding benzoic acid esters of formula (IV). Those skilled in the art will appreciate that a wide variety of conditions may be used for affecting transformations of this kind. In particular, palladium catalysts and phosphine ligands such as RuPhosG3 and RuPhos are routinely employed in the presence of a base, for example, cesium carbonate or lithium hexamethyldisilazide. Such coupling procedures are commonly carried out in polar, non protic solvents such as DMF and at elevated temperatures, for example at 70-80° C. The compounds of formula (II) are obtained following subsequent hydrolysis of the esters (IV) to the free acid. Conditions suitable for this functional group interconversion depend upon the nature of the ester. Primary and secondary esters (for example $R^a$=Me, Et and $Pr^i$) are conveniently saponified by exposure to a suitable inorganic base, for example lithium hydroxide, in an aqueous mixture of aprotic and/or protic solvents, such THF:methanol:water. More hindered examples (for example $R^a$=$^t$Bu) may be more readily de-esterified by treatment with a strong mineral acid such as hydrochloric acid or a strong organic acid, typically trifluoroacetic acid, used either neat or in the presence of a solvent such as DCM.

In an alternative process, using the Buchwald coupling methodology, the advanced ester intermediates of formula (IV) are also available by reaction of the aryl bromides of formula (VIII) with the piperazine motifs of formula (XIV) ($R^a$=lower alkyl, such as $C_{1-5}$ alkyl, for example methyl or ethyl, or else tert-butyl) in a similar manner to that described above. The same technology may be applied to the aryl bromide (VIII) and a suitably protected piperazine of formula (IX), thereby generating the intermediates of formula (VII), which are transformed to the aforementioned compounds of formula (V) by an appropriate deprotection step. A nitrogen protective group strategy, fit for this purpose, is a urethane employing, for example, the Boc group (P=$CO_2^t$Bu) which is stable under the conditions required for the coupling reaction and may be removed thereafter by treatment with acid. Removal of an N-Boc protective group is typically achieved by treatment with a strong organic acid such as TFA in an inert solvent such DCM at ambient temperature.

In a third approach the benzoic acid esters of formula (IV) may be derived by the reaction of the phenolic intermediates (XIII) [Y=CH] or the corresponding pyridinols [Y=N] with an alkylating agent of formula (XI), wherein Z represents a leaving group and the stereochemistry of the said reagent is absolute as depicted. Typical alkylating agents for transformations of this kind include sulfonate esters such as mesylates (Z=Me $SO_2O$) or triflates (Z=$CF_3SO_2O$) as well as alkyl halides, for example the chloromethyl or the bromomethyl derivative (Z=Cl and Br respectively).

A significant practical consideration is that the tosylate derivative (XIa) [Z=p-TolyISO$_2$O], namely: ((3S,5R)-5-((1H-1,2,4-triazol-1-yl)methyl-5-(2,4-difluorophenyl)tetrahydrofuran-3-yl) methyl 4-methylbenzenesulfonate, is a widely available reagent, in bulk, from commercial sources, in high enantiomeric purity. This derivative is also chemically and configurationally stable and, as a solid, offers operational advantages over alternative, more volatile (and therefore more hazardous) alkylating agents. The etherification process is typically carried out under basic conditions, for example in the presence of sodium ethoxide (to generate the phenoxide anion in situ) in a polar, aprotic solvent, suitably DMF, and at temperatures in the region of 40-50° C.

In a similar manner to that already described above, the 1,4-diarylated piperazines of formula (XIII) originate from the Buchwald coupling of the mono-substituted piperazines (XIV), with bromophenols of formula (X) [Y=CH, $R^c$=H] or with the corresponding bromo-pyridinols [Y=N, $R^c$=H] or, in some instances, with suitably protected derivatives thereof [$R^c$≠H]. In those cases wherein the compound of formula (X) has been protected (for example as a methyl or a benzyl ether) the desired coupled product (XIII) is obtained following an appropriate deprotection step (for example 0-demethylation with BBr$_3$ or hydrogenolysis).

The hydroxylated aryl bromides of formula (X) are also converted by the same methodology into the N-arylpiperazines of formula (XII) by a coupling reaction with a mono-protected piperazine of formula (IX). A commonly employed amine protective group for such a purpose is the Boc group in which case the compound of formula (IX) is tert-butyl piperazine-1-carboxylate. It will be apparent to those skilled in the art that other nitrogen protective groups may be selected based upon considerations of orthogonality and operational efficiency. Alkylation of the free hydroxyl function in the N-arylpiperazines of formula (XII) with the tosylate (XIa), as described above, gives rise to the intermediates of formula (VII).

It will be appreciated from the preparative routes outlined above (Scheme 1) that in some instances it is advantageous to perform the same or similar synthetic transformations in a different order, so as to improve the overall efficiency of the processes and/or the quality of the materials obtained therefrom. In addition to those examples already disclosed the hydroxylated aryl bromides of formula (X) may be transformed into the compounds of formula (VII) by conducting the two steps, outlined above, in reverse the order. Treatment of the phenols/pyridinols of formula (X) with the tosylate (XIa) provides the ether derivatives of formula (VIII), which have been converted under Buchwald coupling conditions into the intermediates of formula (VII), as previously described.

Additional strategies for preparing the compounds of the invention, using the synthetic technologies described above, are revealed below (Scheme 2) in which the same or closely related intermediates appearing above (Scheme 1) are assembled in a different order.

Scheme 2

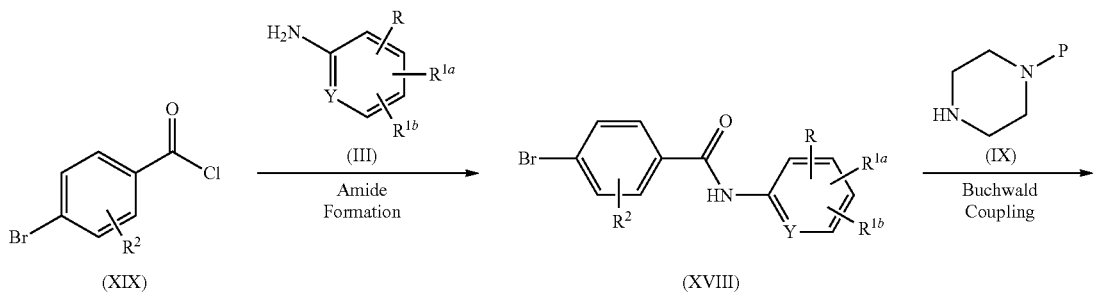

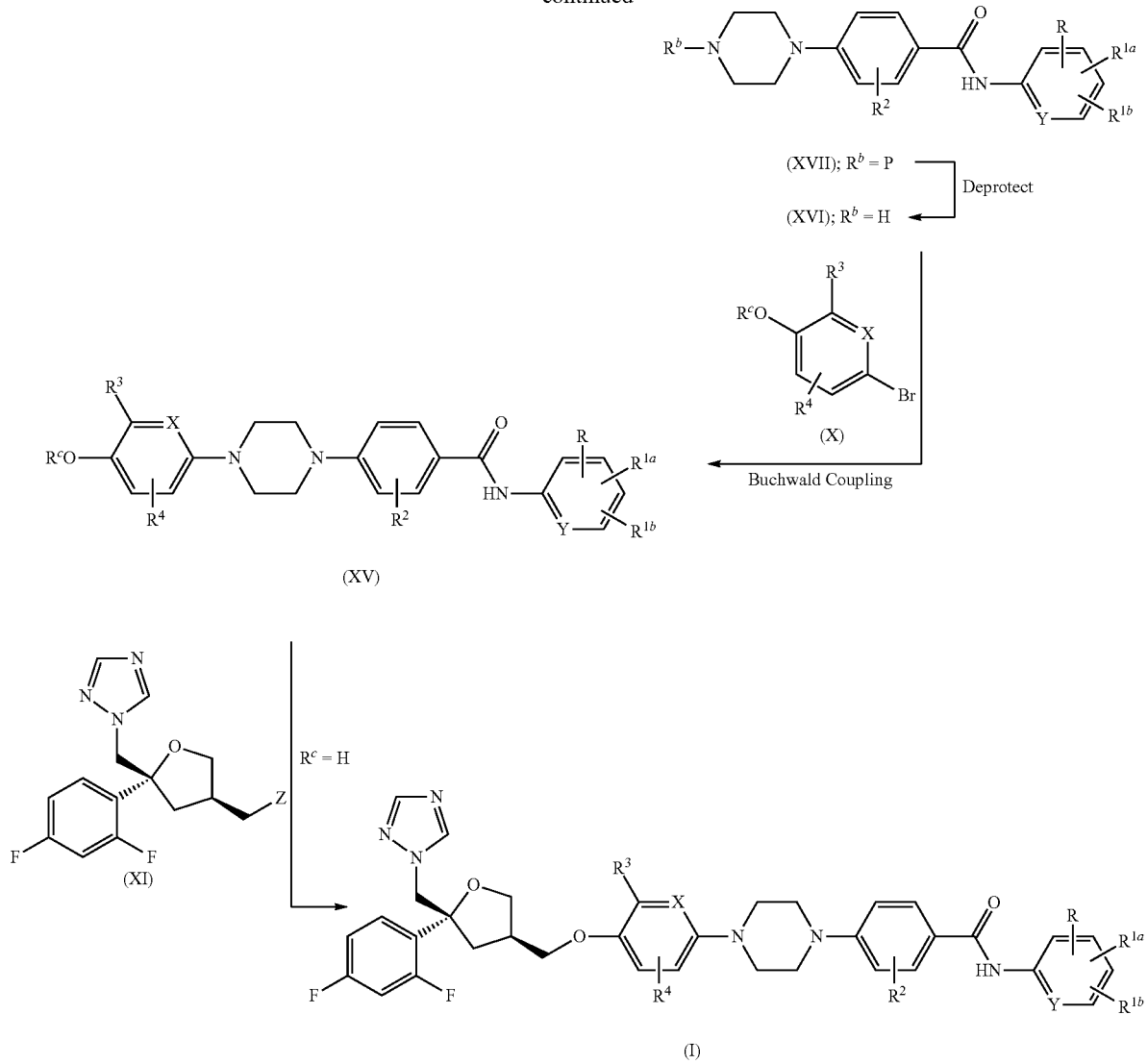

Treatment of the aniline components (III) with the benzoyl chlorides (XIX) provides the benzanilide derivatives of formula (XVIII). As already noted such amidic products may be prepared from the corresponding amine and benzoic acids directly using a wide variety of activating agents, including peptide coupling reagents, of which many are available in the art. Subjecting these products to the Buchwald coupling reaction with a suitable mono-protected piperazine (IX), under the agency of a catalyst, in the manner recorded above, gives rise to the intermediates of formula (XVII). Piperazine derivatives that are stable under these bond forming conditions include urethanes such as the N-Boc derivative, though alternatives (such as a Cbz group) may be advantageous in some cases. Removal of the amine protective group under suitable conditions and a second palladium mediated N-arylation procedure with an aromatic bromide of formula (X), or a protected derivative thereof, furnishes the advanced intermediates of formula (XV).

In some instances this transformation may be accomplished using substrates (X) in which the free hydroxyl group is present (i.e. Rc=H), In other cases it may be preferable to protect the said functionality as, for example, an ether derivative, typically as a benzyl ether, which may be reverted to the free phenol or pyridinol by O-dealkylation under hydrogenolytic conditions Representative compounds of formula (I) are then obtained by the subsequent alkylation of the hydroxyl group with a reagent of formula (XI), most suitably with the tosylate (XIa).

Compounds of the invention wherein the benzamide is formed with a 2-aminopyridine, (I) [Y=N], are accessible from the palladium mediated cross coupling of a primary carboxamide of formula (XX) with an optionally substituted, 2-bromopyridine substrate of formula (XXI). (Scheme 3). Typical reaction conditions for effecting the Buchwald amidation of aryl halides include the use of a palladium catalyst, such as tris(dibenzylideneacetone)dipalladium(0) in the presence of a phosphine ligand, commonly Xantphos and the like and under basic conditions, for example using cesium carbonate. It is usual to conduct such reactions in a polar, aprotic solvent, typically DMF, at elevated temperatures such as 80-100° C. The primary benzamides (XX) are readily generated from the corresponding benzoic acids (II) by treating them with a source of ammonia, conveniently ammonium chloride, under standard peptide coupling conditions.

Scheme 3

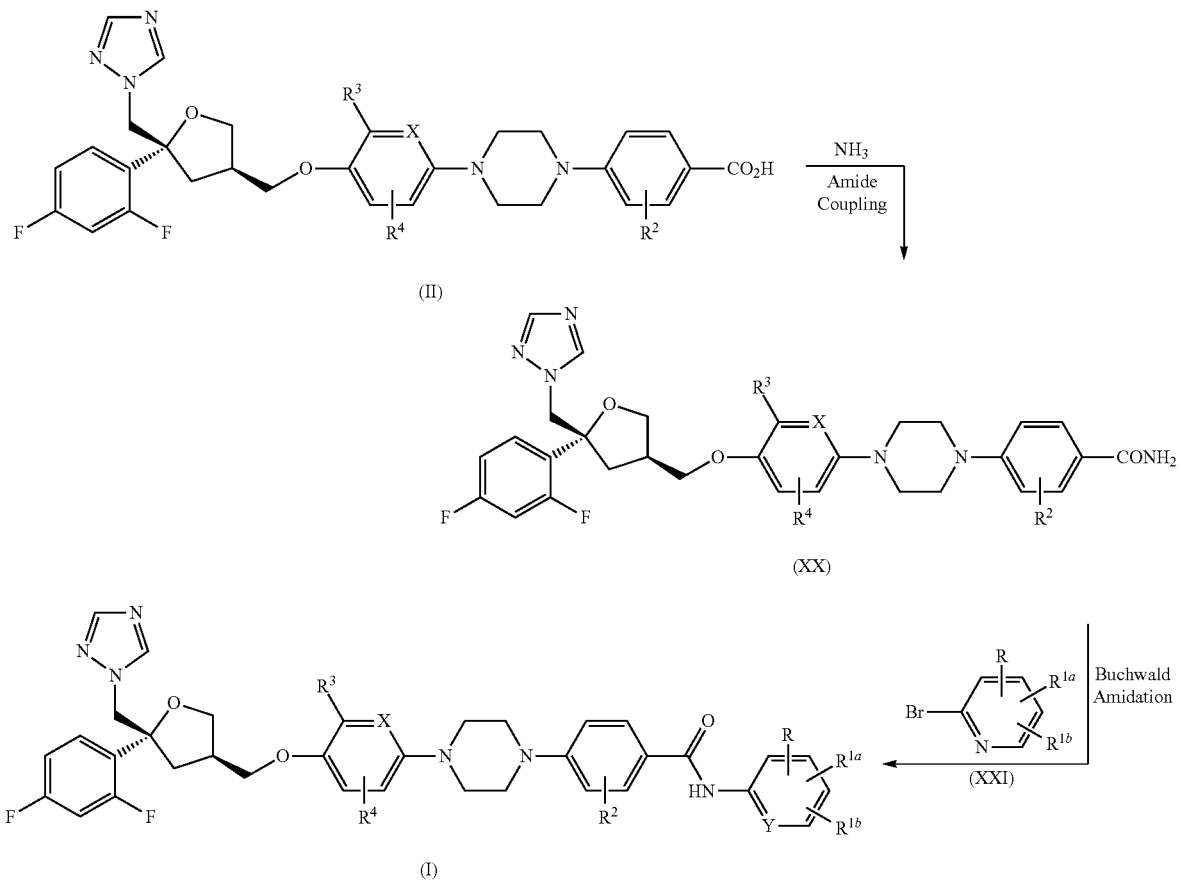

Protective groups and the means for their removal are described in "*Protective Groups in Organic Synthesis*", by Theodora W. Greene and Peter G. M. Wuts, published by John Wiley & Sons Inc; 4th Rev Ed., 2006, ISBN-10: 0471697540. A review of methodologies for the preparation of amides is covered in: "*Amide bond formation and peptide coupling*" Montalbetti, C. A. G. N. and Falque, V. *Tetrahedron*, 2005, 61, 10827-10852.

Thus the invention also provides a process for preparing a compound of formula (I) or a pharmaceutically acceptable salt thereof which comprises reacting a compound of formula (II):

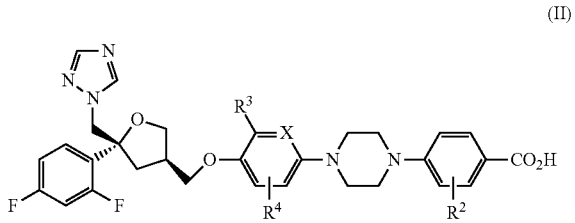

wherein:
$R^2$ represents hydrogen, halo, cyano, $C_{1-4}$ alkyl, $C_{1-4}$ alkoxy or $C_{1-4}$ haloalkoxy;
$R^3$ represents, halo, cyano, $C_{1-4}$ alkyl, or $C_{1-4}$ hydroxyalkyl;
$R^4$ represents, hydrogen or $C_{1-4}$ alkyl;
X represents CH or N;
or an activated derivative thereof (such as an acid halide, e.g. an acid chloride or an acid anhydride); or a salt thereof;
with a compound of formula (III):

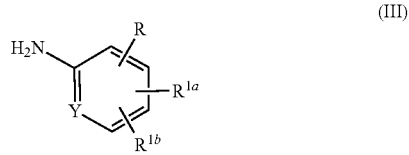

wherein:
R represents hydrogen, halo, cyano, $C_{1-4}$ haloalkyl, $C_{1-4}$ haloalkoxy, or $SO_2NR^5R^6$;
$R^{1a}$ and $R^{1b}$ independently represent hydrogen or halo;
$R^5$ and $R^6$ independently represent hydrogen or $C_{1-4}$ alkyl; and
Y represents CH or N;
or a salt thereof.

The invention also provides a process for preparing a compound of formula (I) or a pharmaceutically acceptable salt thereof which comprises reacting a compound of formula (XV):

(XV)

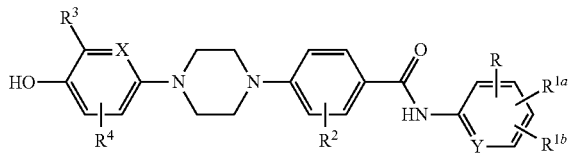

wherein:
R represents hydrogen, halo, cyano, $C_{1-4}$ haloalkyl, $C_{1-4}$ haloalkoxy, or $SO_2NR^5R^6$;
$R^{1a}$ and $R^{1b}$ independently represent hydrogen or halo;
$R^2$ represents hydrogen, halo, cyano, $C_{1-4}$ alkyl, $C_{1-4}$ alkoxy or $C_{1-4}$ haloalkoxy;
$R^3$ represents, halo, cyano, $C_{1-4}$ alkyl, or $C_{1-4}$ hydroxyalkyl;
$R^4$ represents, hydrogen or $C_{1-4}$ alkyl;
$R^5$ and $R^6$ independently represent hydrogen or $C_{1-4}$ alkyl;
X represents CH or N; and
Y represents CH or N;
or a salt thereof;
with a compound of formula (XI):

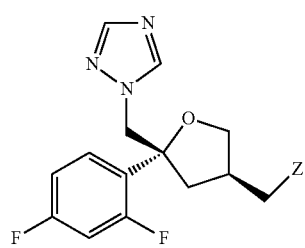

(XI)

wherein:
Z represents a leaving group such as p-TolyISO$_2$O;
or a salt thereof.

The invention also provides a process for preparing a compound of formula (I) or a pharmaceutically acceptable salt thereof which comprises reacting a compound of formula (XX):

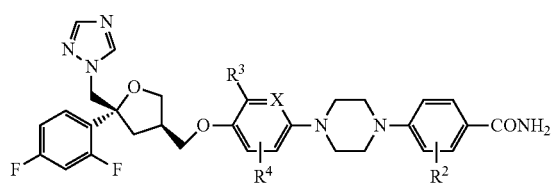

(XX)

wherein:
$R^2$ represents hydrogen, halo, cyano, $C_{1-4}$ alkyl, $C_{1-4}$ alkoxy or $C_{1-4}$ haloalkoxy;
$R^3$ represents, halo, cyano, $C_{1-4}$ alkyl, or $C_{1-4}$ hydroxyalkyl;
$R^4$ represents, hydrogen or $C_{1-4}$ alkyl; and
X represents CH or N;

or a salt thereof;
with a compound of formula (XXI):

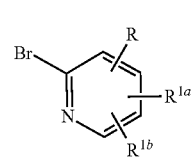

(XXI)

wherein:
R represents hydrogen, halo, cyano, $C_{1-4}$ haloalkyl, $C_{1-4}$ haloalkoxy, or $SO_2NR^5R^6$;
$R^{1a}$ and $R^{1b}$ independently represent hydrogen or halo; and
$R^5$ and $R^6$ independently represent hydrogen or $C_{1-4}$ alkyl;
or a salt thereof.

Pharmaceutically acceptable salts of the compounds of formula (I) include in particular pharmaceutically acceptable acid addition salts of said compounds. The pharmaceutically acceptable acid addition salts of compounds of formula (I) are meant to comprise the therapeutically active non-toxic acid addition salts that the compounds of formula (I) are able to form. These pharmaceutically acceptable acid addition salts can conveniently be obtained by treating the free base form with such appropriate acids in a suitable solvent or mixture of solvents. Appropriate acids comprise, for example, inorganic acids such as hydrohalic acids, e.g. hydrochloric or hydrobromic acid, sulfuric, nitric, phosphoric acids and the like; or organic acids such as, for example, acetic, propanoic, hydroxyacetic, lactic, pyruvic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic acid and the like.

Conversely said salt forms can be converted by treatment with an appropriate base into the free base form.

The definition of the compounds of formula (I) is intended to include all tautomers of said compounds.

The definition of the compounds of formula (I) is intended to include all solvates of said compound (including solvates of salts of said compound) unless the context specifically indicates otherwise. Examples of solvates include hydrates.

The compounds of the disclosure include embodiments wherein one or more atoms specified are naturally occurring or non-naturally occurring isotopes. In one embodiment the isotope is a stable isotope. Thus the compounds of the disclosure include, for example, deuterium containing compounds and the like.

The disclosure also extends to all polymorphic forms of the compounds herein defined.

Novel intermediates as described herein such as compounds of formula (II), (IV), (V), (VII), (VIII) (XIII), (XV) and (XX) and salts thereof, form a further aspect of the invention. Salts include pharmaceutically acceptable salts (such as those mentioned above) and non-pharmaceutically acceptable salts. Salts of acids (e.g. carboxylic acids) include first and second group metal salts including sodium, potassium, magnesium and calcium salts.

In an embodiment there is provided a pharmaceutical composition comprising one or more compounds of the invention optionally in combination with one or more pharmaceutically acceptable diluents or carriers.

Suitably the compounds of the invention are administered topically to the lung or nose, particularly, topically to the lung. Thus, in an embodiment there is provided a pharmaceutical composition comprising one or more compounds of the invention optionally in combination with one or more topically acceptable diluents or carriers.

Suitable compositions for pulmonary or intranasal administration include powders, liquid solutions, liquid suspensions, nasal drops comprising solutions or suspensions or pressurised or non-pressurised aerosols.

The compositions may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985). The compositions may also conveniently be administered in multiple unit dosage form.

Topical administration to the nose or lung may be achieved by use of a non-pressurised formulation such as an aqueous solution or suspension. Such formulations may be administered by means of a nebuliser e.g. one that can be hand-held and portable or for home or hospital use (i.e. non-portable). An example device is a RESPIMAT inhaler. The formulation may comprise excipients such as water, buffers, tonicity adjusting agents, pH adjusting agents, viscosity modifiers, surfactants and co-solvents (such as ethanol). Suspension liquid and aerosol formulations (whether pressurised or unpressurised) will typically contain the compound of the invention in finely divided form, for example with a $D_{50}$ of 0.5-10 µm e.g. around 1-5 µm. Particle size distributions may be represented using $D_{10}$, $D_{50}$ and $D_{90}$ values. The $D_{50}$ median value of particle size distributions is defined as the particle size in microns that divides the distribution in half. The measurement derived from laser diffraction is more accurately described as a volume distribution, and consequently the $D_{50}$ value obtained using this procedure is more meaningfully referred to as a $Dv_{50}$ value (median for a volume distribution). As used herein Dv values refer to particle size distributions measured using laser diffraction. Similarly, $D_{10}$ and $D_{90}$ values, used in the context of laser diffraction, are taken to mean $Dv_{10}$ and $Dv_{90}$ values and refer to the particle size whereby 10% of the distribution lies below the $D_{10}$ value, and 90% of the distribution lies below the $D_{90}$ value, respectively.

According to one specific aspect of the invention there is provided a pharmaceutical composition comprising one or more compounds of the invention in particulate form suspended in an aqueous medium. The aqueous medium typically comprises water and one or more excipients selected from buffers, tonicity adjusting agents, pH adjusting agents, viscosity modifiers and surfactants.

Topical administration to the nose or lung may also be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC). Suitable CFC propellants include trichloromonofluoromethane (propellant 11), dichlorotetrafluoromethane (propellant 114), and dichlorodifluoromethane (propellant 12). Suitable HFC propellants include tetrafluoroethane (HFC-134a) and heptafluoropropane (HFC-227). The propellant typically comprises 40%-99.5% e.g. 40%-90% by weight of the total inhalation composition. The formulation may comprise excipients including co-solvents (e.g. ethanol) and surfactants (e.g. lecithin, sorbitan trioleate and the like). Other possible excipients include polyethylene glycol, polyvinylpyrrolidone, glycerine and the like. Aerosol formulations are packaged in canisters and a suitable dose is delivered by means of a metering valve (e.g. as supplied by Bespak, Valois or 3M or alternatively by Aptar, Coster or Vari).

Topical administration to the lung may also be achieved by use of a dry-powder formulation. A dry powder formulation will contain the compound of the disclosure in finely divided form, typically with an MMD of 1-10 µm or a $D_{50}$ of 0.5-10 µm e.g. around 1-5 µm. Powders of the compound of the invention in finely divided form may be prepared by a micronization process or similar size reduction process. Micronization may be performed using a jet mill such as those manufactured by Hosokawa Alpine. The resultant particle size distribution may be measured using laser diffraction (e.g. with a Malvern Mastersizer 2000S instrument). The formulation will typically contain a topically acceptable diluent such as lactose, glucose or mannitol (preferably lactose), usually of comparatively large particle size e.g. an MMD of 50 µm or more, e.g. 100 µm or more or a $D_{50}$ of 40-150 µm. As used herein, the term "lactose" refers to a lactose-containing component, including α-lactose monohydrate, β-lactose monohydrate, α-lactose anhydrous, β-lactose anhydrous and amorphous lactose. Lactose components may be processed by micronization, sieving, milling, compression, agglomeration or spray drying. Commercially available forms of lactose in various forms are also encompassed, for example Lactohale® (inhalation grade lactose; DFE Pharma), InhaLac®70 (sieved lactose for dry powder inhaler; Meggle), Pharmatose® (DFE Pharma) and Respitose® (sieved inhalation grade lactose; DFE Pharma) products. In one embodiment, the lactose component is selected from the group consisting of α-lactose monohydrate, α-lactose anhydrous and amorphous lactose. Preferably, the lactose is α-lactose monohydrate.

Dry powder formulations may also contain other excipients such as sodium stearate, calcium stearate or magnesium stearate.

A dry powder formulation is typically delivered using a dry powder inhaler (DPI) device. Example dry powder delivery systems include SPINHALER, DISKHALER, TURBOHALER, DISKUS, SKYEHALER, ACCUHALER and CLICKHALER. Further examples of dry powder delivery systems include ECLIPSE, NEXT, ROTAHALER, HANDIHALER, AEROLISER, CYCLOHALER, BREEZHALER/NEOHALER, MONODOSE, FLOWCAPS, TWINCAPS, X-CAPS, TURBOSPIN, ELPENHALER, MIATHALER, TWISTHALER, NOVOLIZER, PRESSAIR, ELLIPTA, ORIEL dry powder inhaler, MICRODOSE, PULVINAL, EASYHALER, ULTRAHALER, TAIFUN, PULMOJET, OMNIHALER, GYROHALER, TAPER, CONIX, XCELOVAIR and PROHALER.

The compounds of the invention might also be administered topically to another internal or external surface (e.g. a mucosal surface or skin) or administered orally. The compounds of the invention may be formulated conventionally for such routes of administration.

The compounds of the invention are useful in the treatment of mycoses and for the prevention or treatment of disease associated with mycoses.

In an aspect of the invention there is provided use of one or more compounds of the invention in the manufacture of a medicament for the treatment of mycoses and for the prevention or treatment of disease associated with mycoses.

In another aspect of the invention there is provided a method of treatment of a subject with a mycosis which comprises administering to said subject an effective amount of one or more compounds of the invention.

In another aspect of the invention there is provided a method of prevention or treatment of disease associated with a mycosis in a subject which comprises administering to said subject an effective amount of one or more compounds of the invention.

Mycoses may, in particular, be caused by *Aspergillus* spp. such as *Aspergillus fumigatus* or *Aspergillus pullulans* and especially *Aspergillus fumigatus*. Mycoses may also be caused by *Candida* spp. e.g. *Candida albicans* or *Candida glabrata*, *Rhizopus* spp. e.g. *Rhizopus oryzae*, *Cryptococcus* spp. e.g. *Cryptococcus neoformans*, *Chaetomium* spp. e.g. *Chaetomium globosum*, *Penicillium* spp. e.g. *Penicillium chrysogenum* and *Trichophyton* spp. e.g. *Trichophyton rubrum*.

A disease associated with a mycosis is, for example, pulmonary aspergillosis.

The compound of the invention may be used in a prophylactic setting by administering the said compound prior to onset of the mycosis.

Subjects include human and animal subjects, especially human subjects.

The compounds of the invention are especially useful for the treatment of mycoses such as *Aspergillus fumigatus* infection and for the prevention or treatment of disease associated with mycoses such as *Aspergillus fumigatus* infection in at risk subjects. At risk subjects include premature infants, children with congenital defects of the lung or heart, immunocompromised subjects (e.g. those suffering from HIV infection), asthmatics, subjects with cystic fibrosis, elderly subjects and subjects suffering from a chronic health condition affecting the heart or lung (e.g. congestive heart failure or chronic obstructive pulmonary disease).

The compounds of the invention are also useful for the treatment of azole resistant mycoses such as azole resistant *Aspergillus fumigatus* infection, particularly in combination with posaconazole.

The compounds of the invention may be administered in combination with a second or further active ingredient. Second or further active ingredients may, for example, be selected from other anti-fungal agents (such as voriconazole or posaconazole), amphotericin B, an echinocandin (such as caspofungin) and an inhibitor of 3-hydroxy-3-methyl-glutaryl-CoA reductase (such as lovastatin, pravastatin or fluvastatin).

Second or further active ingredients include active ingredients suitable for the treatment or prevention of a mycosis such as *Aspergillus fumigatus* infection or disease associated with a mycosis such as *Aspergillus fumigatus* infection or conditions co-morbid with a mycosis such as *Aspergillus fumigatus* infection.

The compounds of the invention may be co-formulated with a second or further active ingredient or the second or further active ingredient may be formulated to be administered separately by the same or a different route.

For example, the compounds of the invention may be administered to patients already being treated systemically with an anti-fungal, such as voriconazole or posaconazole.

For example, the compounds of the invention may be co-administered e.g. co-formulated with one or more agents selected from amphotericin B, an echnocandin, such as caspofungin, and an inhibitor of 3-hydroxy-3-methyl-glutaryl-CoA reductase, such as lovastatin, pravastatin or fluvastatin.

The compound of the invention may alternatively (or in addition) be co-administered e.g. co-formulated with one or more agents selected from candicidin, filipin, hamycin, natamycin, nystatin, rimocidin, bifonazole, butoconazole, clotrimazole, econazole, fenticonazole, isoconazole, ketoconazole, luliconazole, miconazole, omoconazole, oxiconazole. sertaconazole, sulconazole, tioconazole, albaconazole, efinaconazole, epoxiconazole, fluconazole, isavuconazole, itraconazole, propiconazole, ravuconazole, terconazole, abafungin, amorolfin, butenafine, naftifine, terbinafine, anidulafungin, micafungin, benzoic acid, ciclopirox, flucytosine (5-fluorocytosine), griseofulvin, tolnaftate and undecylenic acid.

Preferred combination partners include intraconazole, voriconazole, caspofungin and posaconazole.

According to an aspect of the invention there is provided a kit of parts comprising (a) a pharmaceutical composition comprising one or more compounds of the invention optionally in combination with one or more diluents or carriers; (b) a pharmaceutical composition comprising a second active ingredient optionally in combination with one or more diluents or carriers; (c) optionally one or more further pharmaceutical compositions each comprising a third or further active ingredient optionally in combination with one or more diluents or carriers; and (d) instructions for the administration of the pharmaceutical compositions to a subject in need thereof. The subject in need thereof may suffer from or be susceptible to a mycosis such as *Aspergillus fumigatus* infection.

The compounds of the invention may be administered at a suitable interval, for example once per day, twice per day, three times per day or four times per day.

A suitable dose amount for a human of average weight (50-70 kg) is expected to be around 50 μg to 10 mg/day e.g. 500 μg to 5 mg/day although the precise dose to be administered may be determined by a skilled person.

The compounds of the invention are expected to have one or more of the following favourable attributes:

potent antifungal activity, particularly activity against *Aspergillus* spp. such as *Aspergillus fumigatus*, or activity against *Candida* spp., e.g. *Candida albicans* or *Candida glabrata*, *Rhizopus* spp., e.g. *Rhizopus oryzae*, *Cryptococcus* spp., e.g. *Cryptococcus neoformans*, *Chaetomium* spp., e.g. *Chaetomium globosum*, *Penicillium* spp., e.g. *Penicillium chrysogenum* or *Trichophyton* spp., e.g. *Trichophyton rubrum*, especially following topical administration to the lung or nose;

a long duration of action in lungs, preferably consistent with once daily dosing;

low systemic exposure following topical administration to the lung or nose; and an acceptable safety profile, especially following topical administration to the lung or nose.

EXPERIMENTAL SECTION

Abbreviations used herein are defined below (Table 1). Any abbreviations not defined are intended to convey their generally accepted meaning.

TABLE 1

| | Abbreviations |
|---|---|
| ABPA | allergic bronchopulmonary aspergillosis |
| aq | aqueous |
| ATCC | American Type Culture Collection |

TABLE 1-continued

| Abbreviations | |
|---|---|
| BALF | bronchoalveolar lavage fluid |
| BEAS2B | SV40-immortalised human bronchial epithelial cell line |
| Boc | tert-butyloxycarbonyl |
| br | broad |
| BSA | bovine serum albumin |
| $CC_{50}$ | 50% cell cytotoxicity concentration |
| CFU | colony forming unit(s) |
| CLSI | Clinical and Laboratory Standards Institute |
| COI | cut off index |
| conc | concentration/concentrated |
| d | doublet |
| DCM | dichloromethane |
| $DFB_{50}$ | days taken to reach a fungal burden of 50% of control |
| DIPEA | N,N-diisopropylethylamine |
| DMAP | 4-dimethylaminopyridine |
| DMEM | Dulbecco's Modified Eagle Medium |
| DMF | N,N-dimethylformamide |
| DMSO | dimethyl sulfoxide |
| DSS | dextran sodium sulphate |
| EBM | endothelial basal media |
| ECM | extracellular matrix |
| EDCl•HCl | N-(3-dimethylaminopropyl)-N'-ethylcarbodiimide hydrochloride |
| EGM2 | endothelial cell growth media 2 |
| EUCAST | European Committee on Antimicrobial Susceptibility Testing |
| (ES+) | electrospray ionization, positive mode |
| Et | ethyl |
| $Et_3N$ | triethylamine |
| EtOAc | ethyl acetate |
| FBS | foetal bovine serum |
| GM | galactomannan |
| HPAEC | Human pulmonary artery endothelial cell |
| HOBt•$H_2O$ | 1-hydroxybenzotriazole mono-hydrate |
| HPLC | reverse phase high performance liquid chromatography |
| hr | hour(s) |
| IA | invasive aspergillosis |
| i.n. | intranasal |
| IPA | 2-propanol |
| i.t. | intra-tracheal |
| LC-MS | liquid chromatography-mass spectrometry |
| Li Hep | lithium heparin |
| LiHMDS | lithium bis(trimethylsilyl)amide |
| m | multiplet |
| (M + H)+ | protonated molecular ion |
| MDA | malondialdehyde |
| Me | methyl |
| MeCN | acetonitrile |
| MeOH | methanol |
| MHz | megahertz |
| $MIC_{50}$ | 50% of minimum inhibitory concentration |
| $MIC_{75}$ | 75% of minimum inhibitory concentration |
| $MIC_{90}$ | 90% of minimum inhibitory concentration |
| min | minute(s) |
| MMD | mass median diameter |
| MOI | multiplicity of infection |
| MOPS | 3-(N-morpholino)propanesulfonic acid |
| m/z: | mass-to-charge ratio |
| NCPF | National Collection of Pathogenic Fungi |
| NMR | nuclear magnetic resonance (spectroscopy) |
| NT | not tested |
| OD | optical density |
| PBS | phosphate buffered saline |
| P | protective group |
| q | quartet |
| RT | room temperature |
| RP HPLC | reverse phase high performance liquid chromatography |
| RPMI | Roswell Park Memorial Institute medium |
| RuPhos | 2-dicyclohexylphosphino-2',6'-diisopropoxybiphenyl |
| RuPhosG3 | (2-dicyclohexylphosphino-2',6'-diisopropoxybiphenyl)[2-(2'-amino-1,1'-biphenyl)]palladium (II)methanesulfonate |
| s | singlet |
| sat | saturated |
| sc | sub-cutaneous |
| SDS | sodium dodecyl sulphate |
| t | triplet |
| TFA | trifluoroacetic acid |
| THF | tetrahydrofuran |
| TR34/L98H | An *Aspergillus fumigatus* strain containing a leucine-to-histidine substitution at codon 98 and a 34-bp tandem repeat |
| Xantphos | 4,5-bis(diphenylphosphino)-9,9-dimethylxanthene |

General Procedures

All starting materials and solvents were obtained either from commercial sources or prepared according to the literature citation. Unless otherwise stated all reactions were stirred. Organic solutions were routinely dried over anhydrous magnesium sulfate. Hydrogenations were performed on a Thales H-cube flow reactor under the conditions stated.

Column chromatography was performed on pre-packed silica (230-400 mesh, 40-63 μm) cartridges using the amount indicated. SCX was purchased from Supelco. Unless stated otherwise, the reaction mixture to be purified was first diluted with DCM. This solution was loaded directly onto the SCX and washed with MeOH. The desired material was then eluted by washing with 0.7 M $NH_3$ in MeOH.

Preparative Reverse Phase High Performance Liquid Chromatography

Method 1: Waters X-Select CSH column C18, 5 μm (19×50 mm), flow rate 28 mL min$^{-1}$ eluting with a $H_2O$-MeCN gradient containing 0.1% v/v formic acid over 6.5 min using UV detection at 254 nm. Gradient information: 0.0-0.2 min, 20% MeCN; 0.2-5.5 min, ramped from 20% MeCN to 80% MeCN; 5.5-5.6 min, ramped from 80% MeCN to 95% MeCN; 5.6-6.5 min, held at 95% MeCN.

Method 2: Waters X-Select CSH column C18, 5 μm (19×50 mm), flow rate 28 mL min$^{-1}$ eluting with a $H_2O$-MeCN gradient containing 0.1% v/v formic acid over 6.5 min using UV detection at 254 nm. Gradient information: 0.0-0.2 min, 50% MeCN; 0.2-5.5 min, ramped from 50% MeCN to 80% MeCN; 5.5-5.6 min, ramped from 80% MeCN to 95% MeCN; 5.6-6.5 min, held at 95% MeCN.

Method 3: Waters X-Select CSH column C18, 5 μm (19×50 mm), flow rate 28 mL min$^{-1}$ eluting with a $H_2O$-MeCN gradient containing 0.1% v/v formic acid over 6.5 min using UV detection at 254 nm. Gradient information: 0.0-0.2 min, 35% MeCN; 0.2-5.5 min, ramped from 35% MeCN to 65% MeCN; 5.5-5.6 min, ramped from 65% MeCN to 95% MeCN; 5.6-6.5 min, held at 95% MeCN.

Analytical Methods

Reverse Phase HPLC Methods: Waters Xselect CSH C18 XP column, 2.5 μm (4.6×30 mm) at 40° C.; flow rate 2.5-4.5 mL min$^{-1}$ eluted with a $H_2O$-MeCN gradient containing either 0.1% v/v formic acid (Method a) or 10 mM $NH_4HCO_3$ in water (Method b) over 4 min employing UV detection at 254 nm. Gradient information: 0-3.00 min, ramped from 95% $H_2O$-5% MeCN to 5% $H_2O$-95% MeCN; 3.00-3.01 min, held at 5% $H_2O$-95% MeCN, flow rate increased to 4.5 mL min$^{-1}$; 3.01 3.50 min, held at 5% $H_2O$-95% MeCN; 3.50-3.60 min, returned to 95% $H_2O$-5% MeCN, flow rate reduced to 3.50 mL min$^{-1}$; 3.60-3.90 min, held at 95% $H_2O$-5% MeCN; 3.90-4.00 min, held at 95% $H_2O$-5% MeCN, flow rate reduced to 2.5 mL min$^{-1}$.

$^1$H NMR Spectroscopy: $^1$H NMR spectra were acquired on a Bruker Advance III spectrometer at 400 MHz using residual undeuterated solvent as reference and unless specified otherwise were run in DMSO-$d_6$.

Representative Procedures for the Preparation of Intermediates tert-butyl 4-(4-hydroxy-3-methylphenyl)piperazine-1-carboxylate

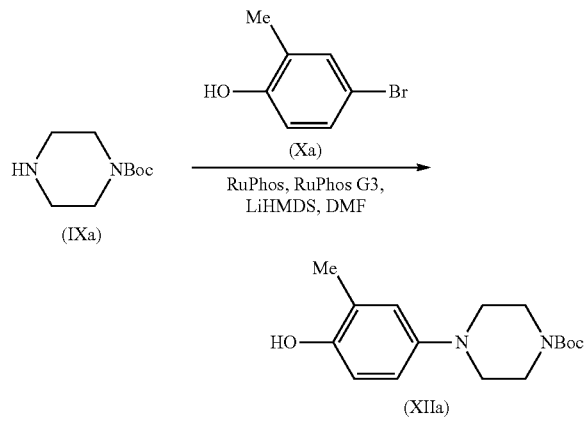

A flask charged with tert-butylpiperazin-1-carboxylate (7.44 g, 40.0 mmol), 4-bromo-2-methylphenol (Xa) (6.23 g, 33.3 mmol), RuPhos (311 mg, 0.67 mmol) and RuPhos G3 (557 mg, 0.67 mmol) was evacuated and backfilled with nitrogen three times. A solution of LiHMDS (1M in THF, 100 mL, 100 mmol) was added and the reaction mixture was heated at 70° C. for 3 hr. After cooling to RT the mixture was quenched by the addition of 1M hydrochloric acid (100 mL) and was then neutralised with 1M aq. NaHCO$_3$ (100 mL). The aq layer was extracted with EtOAc (3×100 mL) and the combined organic extracts were dried. The volatiles were removed in vacuo to give a crude product which was purified by flash column chromatography (SiO$_2$, 120 g, 0-100% EtOAc in isohexanes, gradient elution) to afford the title compound, intermediate (XIIa), as a light brown solid (7.80 g, 78%); R$^t$ 2.07 min (Method b); m/z 293 (M+H)$^+$ (ES$^+$); $^1$H NMR δ: 1.41 (9H, s), 2.07 (3H, s), 2.86-2.88 (4H, m), 3.41-3.43 (4H, m), 6.58-6.65 (2H, m), 6.71 (1H, d) and 8.72 (1H, s).

1-(4-(((3R,5R)-5-((1H-1,2,4-triazol-1-yl)methyl)-5-(2,4-difluorophenyl)tetrahydrofuran-3-yl)methoxy)-3-methylphenyl)piperazine

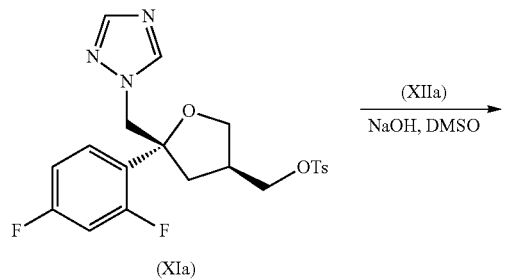

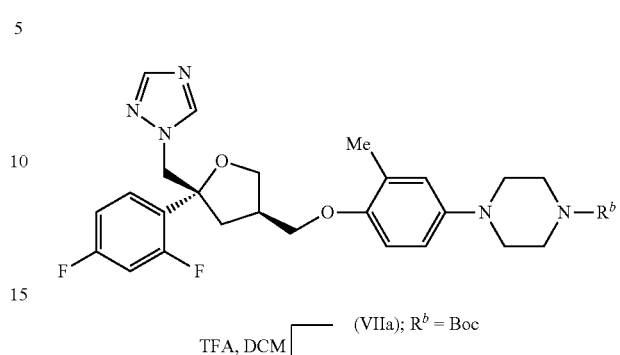

To a solution of intermediate (XIIa) (7.80 g, 25.1 mmol) in DMSO (60 mL) was added aq sodium hydroxide (3.0 mL, 12.5 M, 37.6 mmol). The mixture was stirred at RT for 10 min and was then treated portionwise with the tosylate (XIa) (ex APIChem, Catalogue Number: AC-8330, 12.4 g, 27.6 mmol). The reaction mixture was stirred at 30° C. for 18 hr, cooled to RT and water (200 mL) was added. The resulting mixture was extracted with EtOAc (3×200 mL) and the combined organic extracts were washed with brine (2×200 mL), and then dried and evaporated in vacuo to afford a brown oil. Analysis of the crude, Boc-protected product (VIIa) by $^1$H NMR indicated that it contained 10% of the alkene: (R)-1-((2-(2,4-difluorophenyl)-4-methylenetetrahydrofuran-2-yl)methyl)-1H-1,2,4-triazole, formed as an elimination by-product. The crude urethane (VIIa) was taken up into DCM (150 mL) and treated with TFA (39.0 mL, 502 mmol). After 2 hr at RT the reaction mixture was concentrated in vacuo to remove most of the volatiles and was then diluted with EtOAc (200 mL) and washed with aq. NaOH (2M, 200 mL). The aq phase was separated and was extracted with EtOAc (2×200 mL). The combined organic extracts were washed with brine (2×200 mL) and then dried and evaporated in vacuo to afford a light brown oil. The crude product was purified by flash column chromatography (SiO$_2$, 80 g, 0-10% 0.7 M NH$_3$/MeOH in DCM, gradient elution) to afford the title compound, intermediate (Va), as a viscous, light brown oil (9.46 g, 80%); R$^t$ 1.91 min (Method b); m/z 470 (M+H)$^+$ (ES$^+$); $^1$H NMR δ: 2.07 (3H, s), 2.15 (1H, dd), 2.36-2.42 (1H, m), 2.52-2.56 (1H, m), 2.79-2.81 (4H, m), 2.87-2.90 (4H, m), 3.66 (1H, dd), 3.73-3.77 (2H, m), 4.04 (1H, t), 4.57 (2H, dd), 6.64 (1H, dd), 6.70-6.75 (2H, m), 6.99 (1H, td), 7.25-7.34 (2H, m), 7.76 (1H, s) and 8.34 (1H, s).

Methyl 4-(4-(4-(((3R,5R)-5-((1H-1,2,4-triazol-1-yl)methyl)-5-(2,4-difluorophenyl)tetra hydrofuran-3-yl)methoxy)-3-methylphenyl)piperazin-1-yl)benzoate

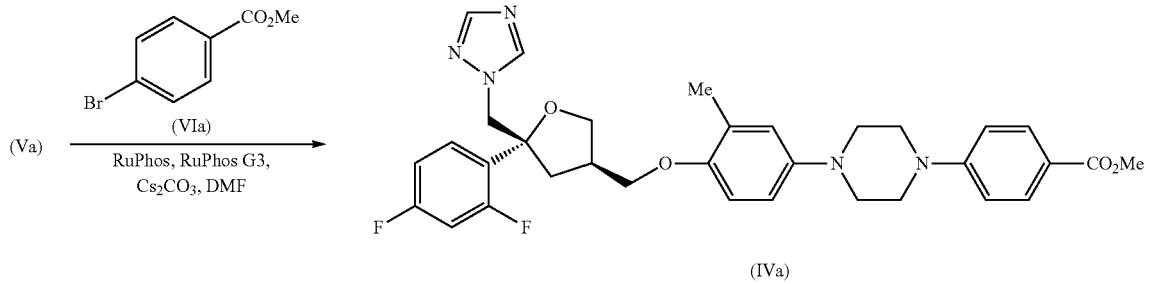 [SMILES: COC(=O)c1ccc(Br)cc1 ; COC(=O)c1ccc(N2CCN(c3ccc(OC[C@@H]4CO[C@@](Cn5cncn5)(c5ccc(F)cc5F)C4)c(C)c3)CC2)cc1 ; "(IVa)"]

A flask charged with intermediate (Va) (9.00 g, 19.2 mmol), methyl-4-bromobenzoate (VIa) (4.95 g, 23.0 mmol), RuPhos (0.18 g, 0.38 mmol, 2 mol %), RuPhosG3 (0.32 g, 0.38 mmol, 2 mol %) and cesium carbonate (9.99 g, 30.7 mmol) was evacuated and refilled with nitrogen three times before DMF (150 mL) was added. The mixture was heated at 80° C. for 22 hr and then, whilst still hot, was poured into water (150 mL) to form a brown gum. More water (300 mL) was added and the aq. phase was extracted with DCM (2×200 mL). The organic extracts were combined and concentrated in vacuo to give a brown oil which was poured into water (100 mL). The resulting precipitate was collected by filtration and then re-suspended in THF (100 mL). The mixture was heated at reflux for 1 hr during which time a cream suspension was formed. The mixture was cooled to RT and the resulting precipitate was collected by filtration, washed with THF (2×50 mL) and then dried in vacuo to afford the title compound, intermediate (IVa), as a light yellow solid (9.48 g, 79%); R' 2.79 min (Method b); m/z 604 (M+H)$^+$ (ES$^+$); $^1$H NMR δ: 2.09 (3H, s), 2.16 (1H, dd), 2.37-2.43 (1H, m), 2.52-2.58 (1H, m), 3.11-3.14 (4H, m), 3.43-3.46 (4H, m), 3.68 (1H, dd), 3.74-3.79 (5H, s overlapping over m), 4.05 (1H, dd), 4.58 (2H, dd), 6.75 (2H, br s), 6.85 (1H, br d), 7.00 (1H, td), 7.04 (2H, d), 7.25-7.34 (2H, m), 7.76 (1H, s), 7.81 (2H, d) and 8.34 (1H, s).

Ethyl 4-(4-(4-hydroxy-3-methylphenyl)piperazin-1-yl)benzoate

A flask charged with a solution of ethyl 4-(piperazin-1-yl)benzoate (XIVa) (20.0 g, 85.0 mmol) and 4-bromo-2-methylphenol (Xa) (19.2 g, 102 mmol) in DMF (213 mL) was evacuated and backfilled with nitrogen three times. RuPhos G3 (1.43 g, 1.71 mmol) was added and the flask was evacuated and backfilled with nitrogen. The reaction mixture was cooled to 0° C. and LiHMDS (17.1 g, 102 mmol) was added. The reaction was stirred at RT for 10 min, then cooled in a water bath and LiHMDS (20.0 g, 120 mmol) added in equal portions (7×2.85 g) at 5 min intervals. The resulting solution was stirred at RT for 30 min and was then cooled to 0° C. and treated with 2M hydrochloric acid (200 mL) resulting in a pH of 6-7. The mixture was stirred for 15 min at RT and was then extracted with EtOAc (220 mL). The aq layer was separated and extracted with EtOAc (4×50 mL) and the combined organics were washed with brine (6×50 mL), and then dried and evaporated in vacuo to afford a cream solid. A mixture of isohexanes and IPA (1:1, 150 mL) was added and the suspension was stirred at RT for 30 min. The solid was collected by filtration, and the filter cake was washed with a mixture of isohexanes and IPA (1:1, 2×10 mL) followed by isohexanes (4×10 mL) and dried in vacuo at 40° C. for 18 hr to afford the title compound, intermediate (XIIIa), as a cream solid (15.3 g, 50%); R' 2.29 min (Method b); m/z 341 (M+H)$^+$ (ES$^+$); $^1$H NMR δ:1.29 (3H, t), 2.09 (3H, s), 3.06-3.09 (4H, m), 3.42-3.44 (4H, m), 4.24 (2H, dd), 6.66 (2H, br s), 6.76 (1H, br s), 7.03 (2H, d), 7.80 (2H, d), 8.72 (1H, 5).

Ethyl 4-(4-(4-(((3R,5R)-5-((1H-1,2,4-triazol-1-yl)methyl)-5-(2,4-difluorophenyl)tetrahydro furan-3-yl)methoxy)-3-methylphenyl)piperazin-1-yl)benzoate

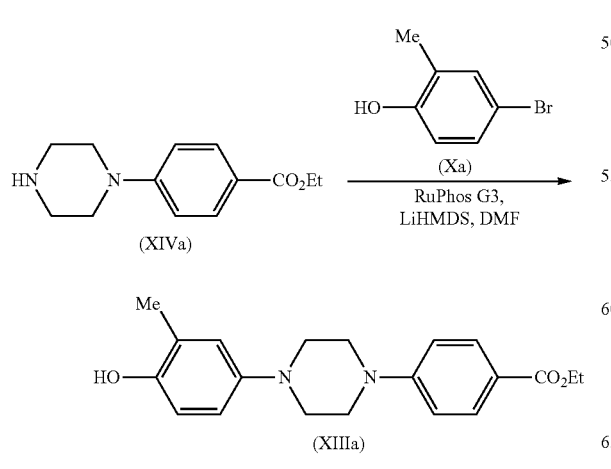

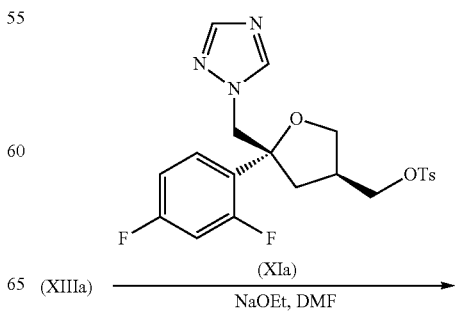

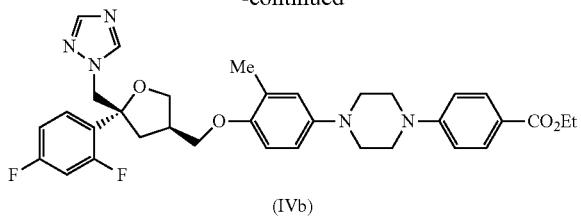

(IVb)

To a solution of intermediate (XIIIa) (15.3 g, 44.9 mmol) in DMF (110 mL) cooled to 0° C. was added sodium ethoxide (3.13 g, 46.1 mmol) and the mixture stirred at 0° C. for 10 min and then treated with the tosylate (XIa). The reaction mixture was allowed to warm to RT, heated to 50° C. for 1 hr and then cooled to RT. Hydrochloric acid (1M, 60 mL) and water (200 mL) were added and the mixture was stirred for 30 min at RT and then extracted with DCM (150 mL). The aq layer was separated and extracted with DCM (2×50 mL) and the combined organics were washed with brine (4×30 mL) and then dried and evaporated in vacuo to afford a cream solid. The solid was suspended in an equal mixture of isohexanes and IPA (80 mL) and stirred at RT for 1 hr. The solid was collected by filtration, washed with a mixture of isohexanes and IPA 1:1 (3×20 mL) and then dried in vacuo at 40° C. for 18 hr to afford the title compound, intermediate (IVb) as a white solid (16.4 g, 56%); $R^t$ 2.92 min (Method b); m/z 618 (M+H)$^+$ (ES$^+$); $^1$H NMR δ: 1.29 (3H, t), 2.10 (3H, s), 2.16 (1H, dd), 2.37-2.42 (1H, m), 2.52-2.58 (1H, m), 3.12-3.14 (4H, m), 3.43-3.46 (4H, m), 3.68 (1H, dd), 3.74-3.79 (2H, m), 4.05 (1H, dd), 4.24 (2H, dd), 4.58 (2H, dd), 6.76 (2H, br s), 6.86 (1H, br s), 6.98-7.05 (3H, m), 7.26-7.34 (2H, m), 7.77 (1H, s), 7.81 (2H, d), 8.34 (1H, s).

2-(Benzyloxy)-5-bromobenzonitrile

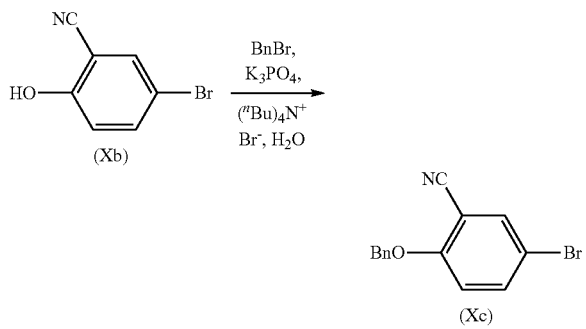

To a stirred suspension of 5-bromo-2-hydroxybenzonitrile (Xb) (1.00 g, 5.05 mmol), tetrabutylammonium bromide (814 mg, 2.53 mmol) and potassium phosphate tribasic monohydrate (1.16 g, 5.05 mmol) in water (10 mL) was added benzyl bromide (600 μL, 5.05 mmol). The mixture was stirred for 18 hr at RT and was extracted with DCM (3×20 mL). The combined organics were washed with brine (20 mL) and then dried and evaporated in vacuo. The crude product so obtained was purified by flash column chromatography (SiO$_2$, 12 g, 0-40% EtOAc in isohexanes, gradient elution) to afford the title compound, intermediate (Xc), as a white solid (1.22 g, 82%); $R^t$ 2.53 min (Method a); m/z no ionisation observed; $^1$H NMR δ: 5.30 (2H, s), 7.31 (1H, d), 7.34-7.48 (5H, m), 7.85 (1H, dd), 8.03 (1H, d).

Methyl 4-(4-(4-(benzyloxy)-3-cyanophenyl)piperazin-1-yl)benzoate

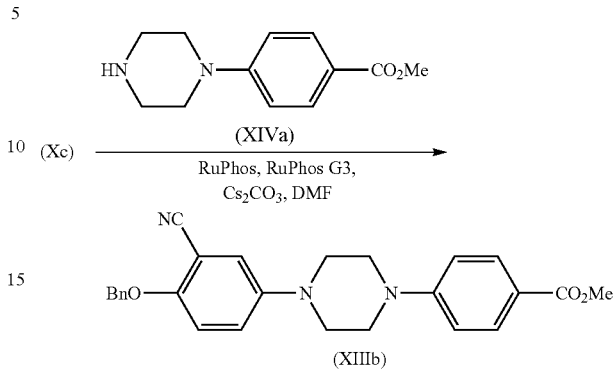

A flask charged with methyl 4-(piperazin-1-yl)benzoate (XIVa) (459 mg, 2.08 mmol), intermediate (Xc) (500 mg, 1.74 mmol), RuPhos (40.0 mg, 87.0 μmol), RuPhos G3 (67.0 mg, 87.0 μmol) and cesium carbonate (678 mg, 2.08 mmol) was evacuated and backfilled with nitrogen three times before DMF (8.0 mL) was added. The mixture was heated at 80° C. for 18 hr and was then cooled to RT and partitioned between water (50 mL) and EtOAc (50 mL). The organic phase was separated and retained and the aq layer was extracted with EtOAc (2×50 mL). The combined organics were washed with brine (3×50 mL) and then dried and evaporated in vacuo to afford a yellow solid. The crude product was triturated in diethyl ether (20 mL), collected by filtration and dried in vacuo at 40° C. for 18 hr to give the title compound, (XIIIb) as a beige solid (286 mg, 37%); $R^t$ 2.74 min (Method a); m/z 428 (M+H)$^+$ (ES$^+$); $^1$H NMR δ: 3.21-3.24 (4H, m), 3.44-3.47 (4H, m), 3.78 (3H, s), 5.22 (2H, s), 7.05 (2H, d), 7.22-7.25 (1H, m), 7.32-7.36 (3H, m), 7.39-7.47 (4H, m), 7.81 (2H, d).

Methyl 4-(4-(3-cyano-4-hydroxyphenyl)piperazin-1-yl)benzoate

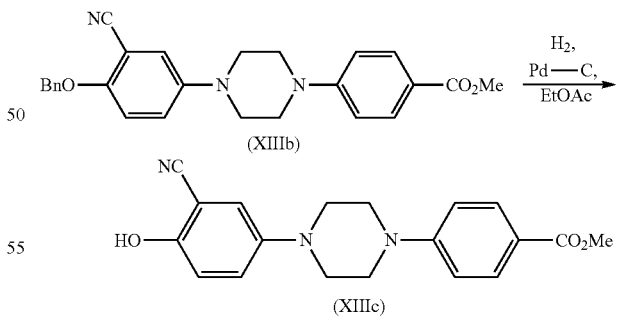

A solution of intermediate (XIIIb) (286 mg, 0.669 mmol) in EtOAc (80 mL) was hydrogenated using the H-Cube (10% palladium on carbon, 70×4 mm, full hydrogen, 30° C., 1 mL/min). The solvent was evaporated in vacuo and the residue was purified by flash column chromatography (SiO$_2$, 4 g, 0-100% EtOAc in DCM, gradient elution) to furnish the title compound, intermediate (XIIIc), as a white solid (139 mg, 60%); $R^t$ 2.06 min (Method a); m/z 338 (M+H)$^+$ (ES$^+$);

¹H NMR δ: 3.14-3.17 (4H, m), 3.43-3.46 (4H, m), 3.78 (3H, s), 6.93 (1H, d), 7.04 (2H, d), 7.16 (1H, d), 7.25 (1H, dd), 7.80 (2H, d), 10.45 (1H, s).

Methyl 4-(4-(4-(((3R,5R)-5-((1H-1,2,4-triazol-1-yl)methyl)-5-(2,4-difluorophenyl)tetra hydrofuran-3-yl)methoxy)-3-cyanophenyl)piperazin-1-yl)benzoate

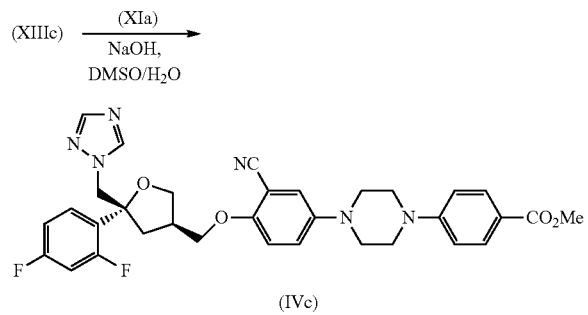 [SMILES: COC(=O)c1ccc(N2CCN(c3ccc(OC[C@@H]4CO[C@@](Cn5cncn5)(c5ccc(F)cc5F)C4)c(C#N)c3)CC2)cc1]

To a solution of intermediate (XIIIc) (139 mg, 0.412 mmol) in DMSO (1.0 mL) was added aq sodium hydroxide (30.0 μL, 12.5 M, 0.381 mmol) and the mixture stirred at RT for 10 min and then treated with a solution of the tosylate (XIa) (154 mg, 0.343 mmol) in DMSO (1.0 mL). The reaction mixture was stirred at 30° C. for 18 hr, cooled to RT and water (30 mL) was added. The resulting mixture was extracted with EtOAc (3×50 mL) and the combined organic extracts were washed with brine (2×30 mL) and dried and evaporated in vacuo to give a brown oil. The crude product was purified by flash column chromatography (SiO₂, 12 g, 0-100% EtOAc in DCM, gradient elution) to give the title compound, intermediate (IVc), as a white foam (100 mg, 46%); R$^r$ 2.59 min (Method a); m/z 615 (M+H)⁺ (ES⁺); ¹H NMR δ: 2.18 (1H, dd), 2.40-2.46 (1H, m), 2.56-2.64 (1H, m), 3.21-3.24 (4H, m), 3.45-3.47 (4H, m), 3.78-3.96 (6H, m), 4.04 (1H, dd), 4.59 (2H, dd), 6.98 (1H, td), 7.05 (2H, d), 7.11 (1H, d), 7.25-7.35 (4H, m), 7.73 (1H, s), 7.81 (2H, d), 8.33 (1H, s).

1-(((2R,4R)-4-((4-bromo-2-methylphenoxy)methyl)-2-(2,4-difluorophenyl)tetrahydro furan-2-yl)methyl)-1H-1,2,4-triazole

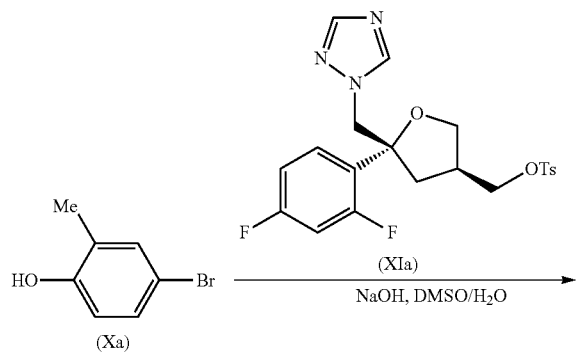

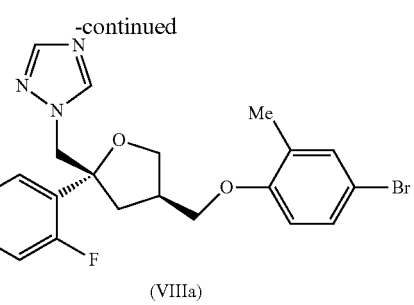

To a solution of 4-bromo-2-methyl phenol (Xa) (920 mg, 4.89 mmol) in DMSO (10 mL) was added aq sodium hydroxide (0.39 mL, 12.5 M, 4.89 mmol) and the mixture stirred at RT for 10 min and then treated with the tosylate (XIa) (2.00 g, 4.45 mmol). The reaction mixture was stirred at 60° C. for 72 hr then cooled to RT and partitioned between water (25 mL) and EtOAc (20 mL). The organic phase was separated and retained and the aq layer was extracted with EtOAc (3×25 mL). The combined organic extracts were washed with brine (3×15 mL) and then dried and evaporated in vacuo. The crude product was purified by flash column chromatography (SiO₂, 12 g, 0-30% EtOAc in DCM, gradient elution) to give the title compound, intermediate (VIIIa), as a colourless oil (1.84 g, 86%); R$^r$ 2.78 min (Method a); m/z 464 (M+H)⁺ (ES⁺); ¹H NMR δ: 2.09 (3H, s), 2.17 (1H, dd), 2.37-2.43 (1H, m), 2.52-2.60 (1H, m), 3.72-3.78 (2H, m), 3.82 (1H, dd), 4.00-4.06 (1H, m), 4.57 (2H, dd), 6.82 (1H, d), 7.00 (1H, td), 7.25-7.34 (4H, m), 7.76 (1H, s), 8.34 (1H, s).

Ethyl 4-(4-(4-(((3R,5R)-5-((1H-1,2,4-triazol-1-yl)methyl)-5-(2,4-difluorophenyl)tetrahydro furan-3-yl)methoxy)-3-methylphenyl)piperazin-1-yl)benzoate

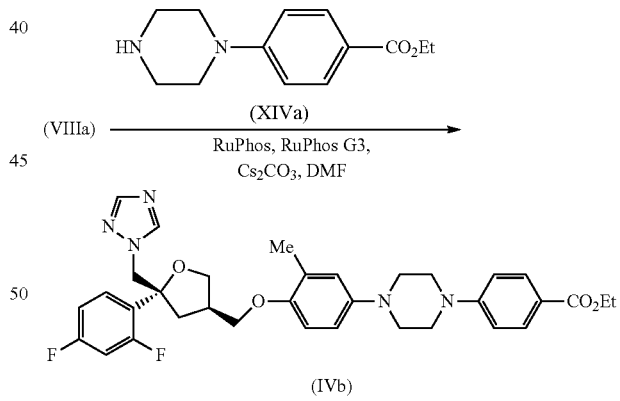

A vial charged with ethyl 4-(piperazin-1-yl)benzoate (XIVa) (103 mg, 0.44 mmol), intermediate (VIIIa) (170 mg, 0.37 mmol), RuPhos (8.5 mg, 18 μmol), RuPhos G3 (14.2 mg, 18 μmol) and cesium carbonate (191 mg, 0.59 mmol) was evacuated and backfilled with nitrogen three times before DMF (3.0 mL) was added. The mixture was heated at 80° C. for 18 h and then at 100° C. for 24 hr. The reaction mixture was cooled to RT and partitioned between water (10 mL) and EtOAc (10 mL). The organic phase was separated and retained and the aq layer was extracted with EtOAc (3×10 mL). The combined organics were washed with brine (3×10 mL) and then dried and evaporated in vacuo. The crude product was purified by flash column chromatography (SiO$_2$, 12 g, 0-100% EtOAc in isohexane, gradient elution) to give the title compound, intermediate (IVb), as a white solid (100 mg, 43%).

3-(((3R,5R)-5-((1H-1,2,4-triazol-1-yl)methyl)-5-(2,4-difluorophenyl)tetrahydrofuran-3-yl) methoxy)-6-bromo-2-methylpyridine

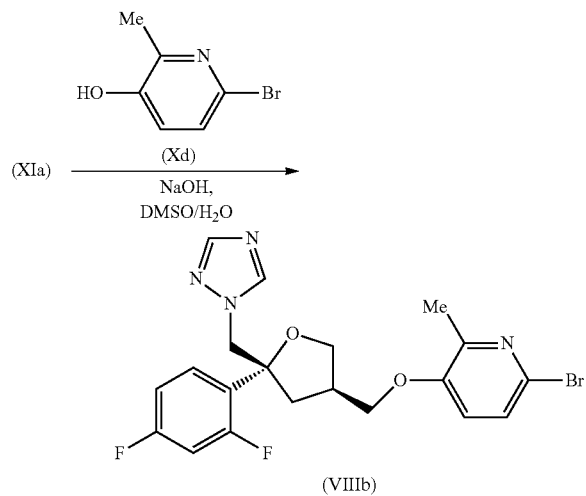

To a solution of 6-bromo-2-methylpyridin-3-ol (Xd) (1.00 g, 5.32 mmol) in DMSO (17 mL) was added aq sodium hydroxide (2.80 mL, 2.0 M, 5.32 mmol) and the mixture stirred at RT for 10 min and then treated portionwise with the tosylate (XIa) (2.17 g, 4.84 mmol). The reaction mixture was stirred at 65° C. for 18 hr, cooled to RT and water (30 mL) was added. The resulting mixture was extracted with EtOAc (3×50 mL) and the combined organics were washed with brine (2×30 mL) and then dried and evaporated in vacuo to afford a yellow oil. The crude product was purified by flash column chromatography (SiO$_2$, 40 g, 0-100% EtOAc in DCM, gradient elution) to afford the title compound, intermediate (VIIIb), as a white solid (1.50 g, 64%); R$^t$ 2.28 min (Method a); m/z 465/467 (M+H)$^+$ (ES$^+$); $^1$H NMR δ: 2.17 (1H, dd), 2.29 (3H, s), 2.38-2.44 (1H, m), 2.54-2.62 (1H, m), 3.74-3.88 (3H, m), 4.03 (1H, dd), 4.58 (2H, dd), 7.00 (1H, td), 7.25-7.35 (3H, m), 7.39 (1H, dd), 7.76 (1H, s), 8.34 (1H, s).

tert-Butyl 4-(5-(((3R,5R)-5-((1H-1,2,4-triazol-1-yl)methyl)-5-(2,4-difluorophenyl)tetra hydrofuran-3-yl)methoxy)-6-methylpyridin-2-yl)piperazine-1-carboxylate

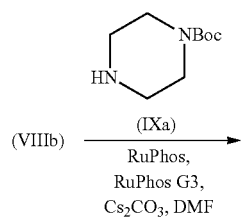

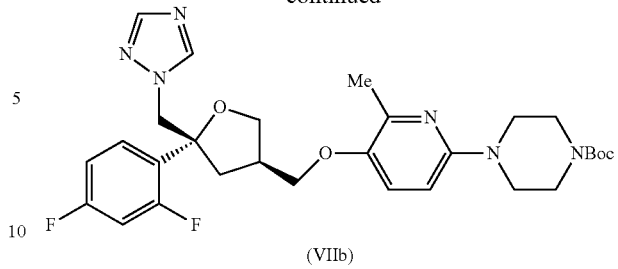

A flask charged with tert-butylpiperazin-1-carboxylate (IXa) (550 mg, 2.93 mmol), intermediate (VIIIb) (1.50 g, 3.22 mmol), RuPhos (68.0 mg, 0.147 mmol), RuPhos G3 (123 mg, 0.147 mmol) and cesium carbonate (1.53 g, 4.69 mmol) was evacuated and backfilled with nitrogen three times before DMF (15 mL) was added. The mixture was heated at 80° C. for 18 hr, then cooled to RT and partitioned between water (100 mL) and EtOAc (100 mL). The organic phase was separated and retained and the aq layer was extracted with EtOAc (2×100 mL). The combined organic extracts were washed with brine (3×50 mL) and then dried and evaporated in vacuo to afford a yellow oil. The crude product was purified by flash column chromatography (SiO$_2$, 80 g, 0-100% EtOAc in DCM, gradient elution) to afford the title compound, intermediate (VIIb), as a white foam (1.38 g, 77%); R$^t$ 2.14 min (Method a); m/z 571 (M+H)$^+$ (ES$^+$); $^1$H NMR δ: 1.41 (9H, s), 2.15 (1H, dd), 2.21 (3H, s), 2.36-2.42 (1H, m), 2.52-2.57 (1H, m), 3.29-3.33 (4H, m), 3.39-3.41 (4H, m), 3.67 (1H, dd), 3.75 (2H, dd), 4.04 (1H, dd), 4.57 (2H, dd), 6.60 (1H, d), 7.00 (1H, td), 7.18 (1H, d), 7.25-7.34 (2H, m), 7.76 (1H, s), 8.34 (1H, s).

1-(5-(((3R,5R)-5-((1H-1,2,4-triazol-1-yl)methyl)-5-(2,4-difluorophenyl)tetrahydrofuran-3-yl)methoxy)-6-methylpyridin-2-yl)piperazine

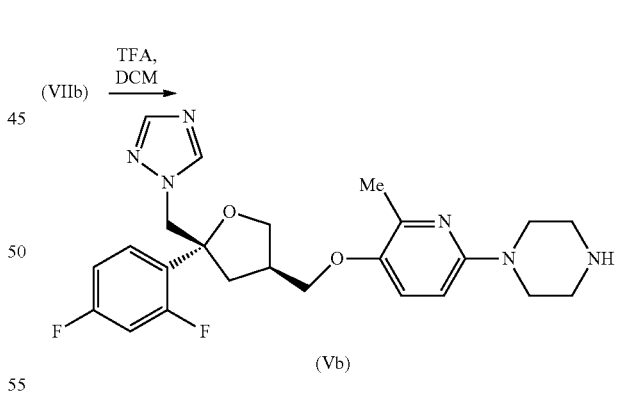

A solution of intermediate (VIIb) in DCM (10 mL) was treated with TFA (2.62 mL, 34.0 mmol) and stirred at RT for 2 hr. The reaction mixture was concentrated in vacuo to give a brown oil, which was partitioned between EtOAc (50 mL) and 1M aq NaHCO$_3$ (20 mL). The organic layer was separated and was washed with brine (20 mL) and then dried and evaporated in vacuo to afford the title compound, intermediate (Vb) as a brown foam (858 mg, 76%); R$^t$ 1.26 min (Method a); m/z 471 (M+H)$^+$ (ES$^+$); $^1$H NMR δ: 2.14 (1H, dd), 2.21 (3H, s), 2.36-2.42 (1H, m), 2.53-2.57 (1H, m), 2.80-2.85 (4H, m), 3.26-3.31 (4H, m), 3.66 (1H, dd), 3.71-

3.77 (2H, dd), 4.04 (1H, t), 4.57 (2H, dd), 6.56 (1H, d), 7.00 (1H, td), 7.17 (1H, d), 7.25-7.34 (2H, m), 7.76 (1H, s), 8.34 (1H, s).

Methyl 4-(4-(5-(((3R,5R)-5-((1H-1,2,4-triazol-1-yl)methyl)-5-(2,4-difluorophenyl)tetra hydrofuran-3-yl)methoxy)-6-methylpyridin-2-yl)piperazin-1-yl)benzoate

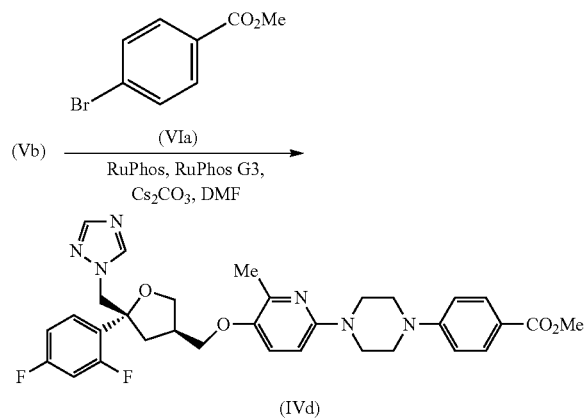

A flask charged with intermediate (Vb) (860 mg, 1.82 mmol), methyl-4-bromobenzoate (VIa) (470 mg, 2.19 mmol), RuPhos (17.0 mg, 0.0360 mmol, 2 mol %), RuPhosG3 (28.0 mg, 0.0360 mmol, 2 mol %) and cesium carbonate (950 mg, 2.92 mmol) was evacuated and refilled with nitrogen three times before DMF (6.0 mL) was added. The mixture was heated at 80° C. for 18 hr, then cooled to RT and partitioned between EtOAc (50 mL) and water (50 mL). The organic layer was separated and was washed with brine (3×50 mL) and then dried and evaporated in vacuo to give a beige solid. The crude product so obtained was purified by flash column chromatography (SiO$_2$, 24 g, 0-100% EtOAc in DCM, gradient elution) to afford the title compound, intermediate (IVd), as a yellow solid (690 mg, 61%); R$^t$ 2.21 min (Method a); m/z 605 (M+H)$^+$ (ES$^+$); $^1$H NMR δ: 2.15 (1H, dd), 2.23 (3H, s), 2.37-2.43 (1H, m), 2.52-2.57 (1H, m), 3.42-3.44 (4H, m), 3.47-3.50 (4H, m), 3.68 (1H, dd), 3.74-3.78 (5H, m), 4.04 (1H, dd), 4.57 (2H, dd), 6.66 (1H, d), 6.97-7.04 (3H, td), 7.21 (1H, d), 7.25-7.34 (2H, m), 7.76 (1H, s), 7.81 (2H, d), 8.34 (1H, s).

4-(4-(4-(((3R,5R)-5-((1H-1,2,4-triazol-1-yl)methyl)-5-(2,4-difluorophenyl)tetrahydrofuran-3-yl)methoxy)-3-methylphenyl)piperazin-1-yl)benzoic acid Hydrolysis of the Methyl Ester (IVa)

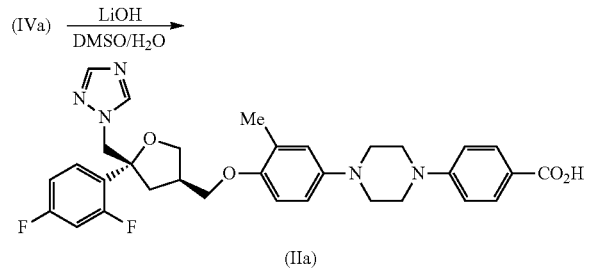

To a suspension of intermediate (IVa) (9.00 g, 14.9 mmol) in DMSO (370 mL) was added a solution of lithium hydroxide (1.79 g, 74.5 mmol) in water (37.0 mL). The mixture was heated at 70° C. for 22 hr and was then cooled to RT, diluted with water (1000 mL) and acidified (to pH 2) by the addition of 1M aq hydrochloric acid (80 mL). The mixture was cooled in an ice bath for 2 hr and the resulting precipitate was collected by filtration. The filter cake was washed with water (3×80 mL) and dried in vacuo at 50° C. to give the title compound, intermediate (IIa) as a white solid (4.66 g, 54%); R$^t$ 2.21 min (Method 1a); m/z 590 (M+H)$^+$ (ES$^+$); $^1$H NMR δ: 2.10 (3H, s), 2.16 (1H, dd), 2.37-2.43 (1H, m), 2.52-2.58 (1H, m), 3.12-3.14 (4H, m), 3.42-3.45 (4H, m), 3.68 (1H, dd), 3.74-3.79 (2H, m), 4.05 (1H, dd), 4.58 (2H, dd), 6.76 (2H, br s), 6.86 (1H, br d), 6.97-7.03 (3H, m), 7.25-7.34 (2H, m), 7.77-7.80 (3H, m), 8.34 (1H, s) and 12.31 (1H, s).

Hydrolysis of the Ethyl Ester (IVb)

To a suspension of intermediate (IVb) (16.4 g, 26.6 mmol) in DMSO (375 mL) was added a solution of lithium hydroxide (3.18 g, 74.5 mmol) in water (50 mL). The mixture was heated at 70° C. for 22 hr and was then cooled to RT, poured into water (500 mL) and acidified (to ~pH 5-6) by the addition of 2M hydrochloric acid (70 mL). The mixture was stirred at RT for 30 min and the resulting solid was collected by filtration and washed with water (2×20 mL) and with diethyl ether (3×30 mL) and then dried in vacuo at 40° C. for 18 hr to afford the title compound, intermediate (IIa) as a tan solid (14.2 g, 84%); R$^t$ 2.26 min (Method 1a); m/z 590 (M+H)$^+$ (ES$^+$); $^1$H NMR δ: 2.09 (3H, s), 2.16 (1H, dd), 2.37-2.42 (1H, m), 2.52-2.58 (1H, m), 3.12-3.14 (4H, m), 3.42-3.44 (4H, m), 3.68 (1H, dd), 3.74-3.79 (2H, m), 4.05 (1H, dd), 4.58 (2H, dd), 6.75 (2H, br s), 6.86 (1H, br s), 6.97-7.03 (3H, m), 7.26-7.34 (2H, m), 7.77-7.80 (3H, m), 8.34 (1H, s), 12.31 (1H, br s).

4-(4-(4-(((3R,5R)-5-((1H-1,2,4-triazol-1-yl)methyl)-5-(2,4-difluorophenyl)tetrahydrofuran-3-yl)methoxy)-3-cyanophenyl)piperazin-1-yl)benzoic acid

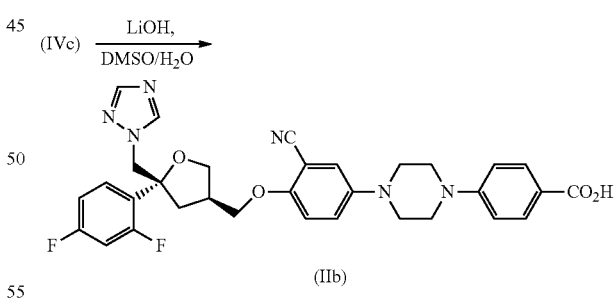

To a suspension of intermediate (IVc) (100 mg, 0.163 mmol) in DMSO (8.0 mL) was added a solution of lithium hydroxide (19 mg, 0.81 mmol) in water (1.0 mL). The mixture was heated at 50° C. for 18 hr, then cooled to RT, diluted with water (10 mL) and acidified (to ~pH 3) by the addition of 1M hydrochloric acid (2.0 mL). The mixture was extracted with 4:1 DCM/EtOAc (2×25 mL) and the combined organics were washed with water (2×10 mL) and dried and evaporated in vacuo to afford a white solid that was dried in vacuo at 40° C. to give the title compound, intermediate (IIb) as a white solid (74 mg, 75%); R$^t$ 2.32 min (Method a); m/z 601 (M+H)⁺ (ES⁺); ¹H NMR δ: 2.18 (1H, dd), 2.40-2.46 (1H, m), 2.58-2.64 (1H, m), 3.21-3.24 (4H, m), 3.43-3.45 (4H, m), 3.78-3.96 (3H, m), 4.04 (1H, dd), 4.59 (2H, dd), 6.98 (1H, td), 7.03 (2H, d), 7.11 (1H, d), 7.25-7.35 (4H, m), 7.74 (1H, s), 7.79 (2H, d), 8.34 (1H, s), 12.30 (1H, br s).

4-(4-(5-(((3R,5R)-5-((1H-1,2,4-triazol-1-yl)methyl)-5-(2,4-difluorophenyl)tetrahydrofuran-3-yl) methoxy)-6-methylpyridin-2-yl)piperazin-1-yl)benzoic acid

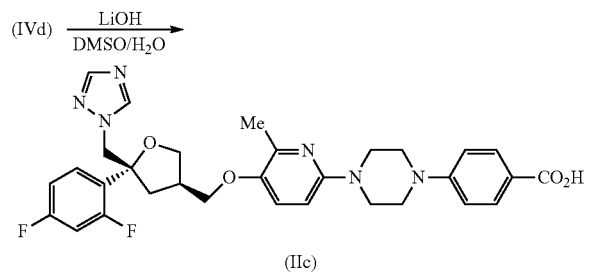

To a suspension of intermediate (IVd) (690 mg, 1.14 mmol) in DMSO (54 mL) was added a solution of lithium hydroxide (140 mg, 5.71 mmol) in water (9.0 mL). The mixture was heated at 70° C. for 22 hr and then cooled to RT, diluted with water (100 mL) and acidified (to ~pH 2) by the addition of 1M hydrochloric acid (6.0 mL). The mixture was cooled in an ice bath for 15 min and the resulting precipitate was collected by filtration, washed with water (3×50 mL) and dried in vacuo at 40° C. to give the title compound, intermediate (IIc), as a yellow solid (617 mg, 87%); R$^t$ 1.91 min (Method a); m/z 591 (M+H)⁺ (ES⁺); ¹H NMR δ: 2.15 (1H, dd), 2.23 (3H, s), 2.37-2.43 (1H, m), 2.52-2.57 (1H, m), 3.39-3.42 (4H, m), 3.47-3.50 (4H, m), 3.68 (1H, dd), 3.74-3.78 (2H, m), 4.04 (1H, dd), 4.57 (2H, dd), 6.66 (1H, d), 6.97-7.02 (3H, td), 7.21 (1H, d), 7.25-7.34 (2H, m), 7.76-7.80 (3H, m), 8.34 (1H, s), 12.31 (1H, br s).

4-Bromo-N-(4-fluorophenyl)benzamide

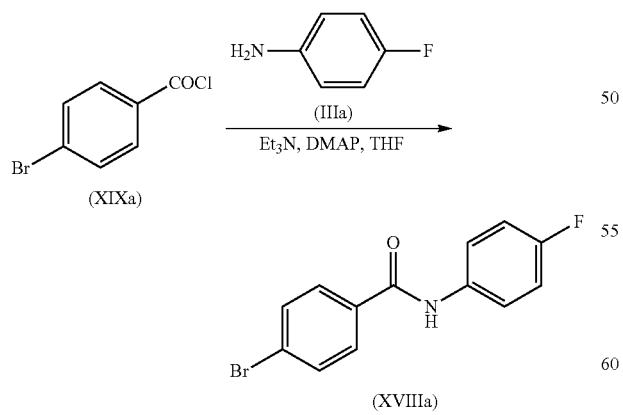

To a solution of 4-fluoroaniline (IIIa) (0.85 mL, 9.00 mmol), triethylamine (1.88 mL, 13.5 mmol) and DMAP (0.11 g, 0.90 mmol) in THF (15 mL) was added 4-bromobenzoyl chloride (XIXa) (2.37 g, 10.8 mmol). The reaction mixture was maintained at RT for 1 hr and was then partitioned between EtOAc (100 mL) and 1M hydrochloric acid (100 mL). The organic phase was separated and was washed sequentially with 1M hydrochloric acid (100 mL), sat. aq. NaHCO₃ (100 mL) and brine (100 mL) and then dried and evaporated in vacuo. The crude residue was triturated from warm DCM (100 mL) and the mixture was heated at reflux to give a white suspension which was allowed to cool to RT. The resulting precipitate was collected by filtration to afford the title compound, intermediate (XVIIIa), as white solid (1.81 g, 65%); R$^t$ 2.23 min; m/z 294/296 (M+H)⁺ (ES⁺); ¹H NMR δ: 7.20 (2H, t), 7.74-7.79 (4H, m), 7.90 (2H, d) and 10.36 (1H, s).

tert-Butyl 4-(4-((4-fluorophenyl)carbamoyl)phenyl) piperazine-1-carboxylate

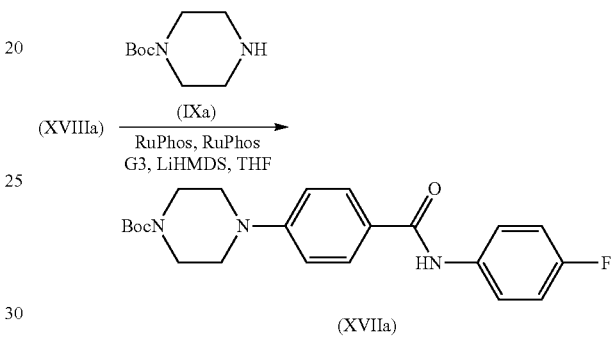

A flask charged with tert-butyl piperazine-1-carboxylate (IXa) (4.00 g, 215 mmol), intermediate (XVIIIa) (6.63 g, 22.6 mmol), RuPhos (100 mg, 0.215 mmol) and RuPhos G3 (180 mg, 0.215 mmol) was evacuated and backfilled with nitrogen three times. A solution of LiHMDS (1M in THF, 75.0 mL, 75.0 mmol) was added and the reaction mixture was heated at 70° C. for 5 hr. After cooling to RT the mixture was partitioned between EtOAc (150 mL) and 1M hydrochloric acid (150 mL). The organic phase was separated and retained and the aq phase was extracted with EtOAc (3×150 mL). The combined organics were dried and concentrated in vacuo to afford a brown solid which was triturated in a mixture of isohexanes and diethyl ether (1:1, 100 mL). The product so obtained was collected by filtration, washed with a mixture of isohexanes and diethyl ether (1:1, 25 mL) and then dried in vacuo at 40° C. to provide the title compound, intermediate (XVIIa) as a tan solid (6.44 g, 85%); R$^t$ 2.40 min (Method a); m/z 400 (M+H)⁺; ¹H NMR δ: 1.43 (9H, s), 3.27-3.30 (4H, m), 3.45-3.48 (4H, m), 7.03 (2H, d), 7.14-7.18 (2H, m), 7.74-7.79 (2H, m), 7.88 (2H, d), 9.99 (1H, s).

N-(4-fluorophenyl)-4-(piperazin-1-yl)benzamide

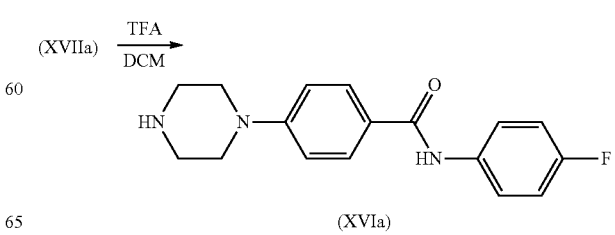

To a solution of intermediate (XVIIa) (6.44 g, 16.1 mmol) in DCM (200 mL) was added TFA (24.7 mL, 322 mmol). The reaction was stirred at RT for 2 hr and was then evaporated in vacuo. Toluene (5.0 mL) was added and the mixture was again evaporated in vacuo. The resulting oil was taken up in a mixture of DCM (90 mL) and methanol (10 mL) and was then extracted with a mixture of water (50 mL) and sat. aq NaHCO$_3$ (50 mL). The organic phase was separated and retained and the aq layer was extracted with a mixture of DCM and methanol (9:1, 3×100 mL). The combined organic layers were dried and concentrated in vacuo to afford the title compound, intermediate (XVIa), as a brown solid (3.74 g, 70%); R$^t$ 1.02 min (Method a); m/z 300 (M+H)$^+$; $^1$H NMR δ: 2.81-2.83 (4H, m), 3.18-3.20 (4H, m), 6.99 (2H, d), 7.14-7.18 (2H, m), 7.74-7.80 (2H, m), 7.85 (2H, d), 9.99 (1H, s).

N-(4-fluorophenyl)-4-(4-(4-methoxy-3-methylphenyl)piperazin-1-yl)benzamide

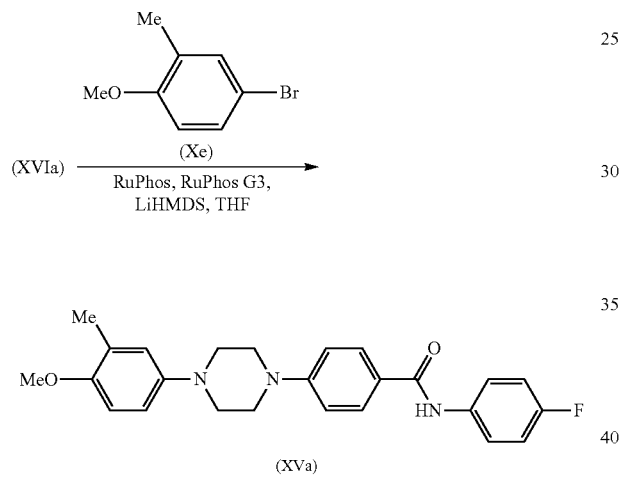

A flask charged with 4-bromo-1-methoxy-2-methylbenzene (Xe) (406 mg, 2.02 mmol), intermediate (XVIa) (550 mg, 1.84 mmol), RuPhos (43 mg, 0.092 mmol) and RuPhos G3 (77 mg, 0.092 mmol) was evacuated and backfilled with nitrogen three times. A solution of LiHMDS (9.2 mL, 1M in THF, 9.2 mmol) was added and the reaction mixture was heated at 70° C. for 8 hr. After cooling to RT the mixture was quenched by the addition of 1M aq. hydrochloric acid (9.0 mL) and then partitioned between water (15 mL) and EtOAc (15 mL). The organic layer was separated and retained and the aq layer was extracted with EtOAc (2×15 mL). The combined organics were washed with brine (20 mL) and then dried and evaporated in vacuo. The crude product so obtained was purified by flash column chromatography (SiO$_2$, 12 g, 0-100% EtOAc in isohexane, gradient elution) to afford a yellow solid. This material was repurified by flash column chromatography (SiO$_2$, 4 g, 0-10% EtOAc in DCM, gradient elution) to afford the title compound, intermediate (XVa), as an off-white solid (83 mg, 11%); R$^t$ 2.27 min (Method a); m/z 420 (M+H)$^+$ (ES$^+$); $^1$H NMR δ: 2.13 (3H, s), 3.13-3.16 (4H, m), 3.42-3.45 (4H, m), 3.72 (3H, s), 6.77-6.88 (3H, m), 7.08 (2H, d), 7.17 (2H, t), 7.75-7.80 (2H, m), 7.89 (2H, d), 10.02 (1H, s).

N-(4-fluorophenyl)-4-(4-(4-hydroxy-3-methylphenyl)piperazin-1-yl)benzamide

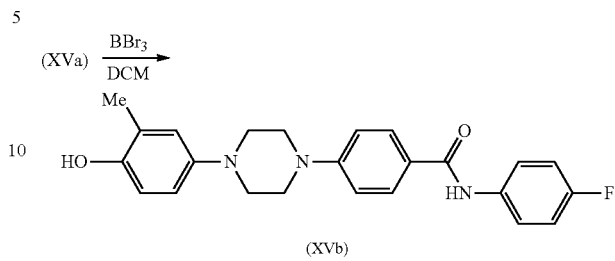

To a suspension of intermediate (XVa) (83 mg, 0.20 mmol) in DCM (5.0 mL) at 0° C. was added a solution of boron tribromide (0.59 mL, 1M in DCM, 0.59 mmol). The reaction mixture was stirred at 0° C. for 30 min, allowed to warm to RT for 8 hr and was then partitioned between water (15 mL) and DCM (10 mL). The organic layer was separated and retained and the aq layer was extracted with a mixture of DCM and MeOH (90:10, 5×15 mL). The combined organics were dried and evaporated in vacuo to give a crude product which was purified by flash column chromatography (SiO$_2$, 4.0 g, 0-3% MeOH in DCM, gradient elution) to afford the title compound, intermediate (XVb), as a beige solid (61 mg, 72%); R$^t$ 1.73 min (Method a); m/z 406 (M+H)$^+$ (ES$^+$); $^1$H NMR δ: 2.10 (3H, s), 3.08-3.11 (4H, m), 3.41-3.43 (4H, m), 6.67 (2H, br s), 6.77 (1H, br s), 7.07 (2H, d), 7.17 (2H, t), 7.76-7.80 (2H, m), 7.89 (2H, d), 8.73 (1H, s), 10.01 (1H, s).

N-(4-fluorophenyl)-4-(4-(4-hydroxy-2,5-dimethylphenyl)piperazin-1-yl)benzamide

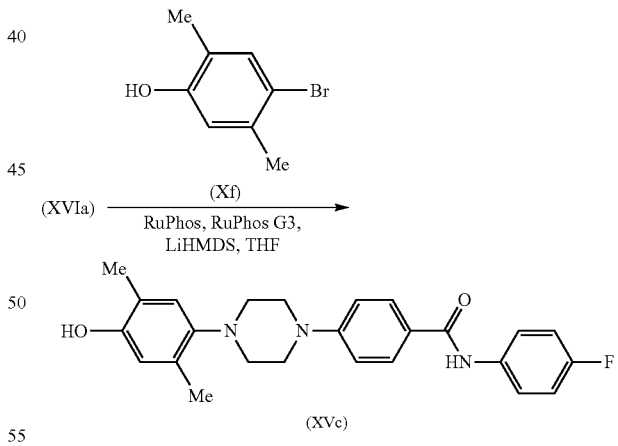

A flask charged with 4-bromo-2,5-dimethylphenol (Xf) (73.1 mg, 0.364 mmol), intermediate (XVIa) (120 mg, 0.400 mmol), RuPhos (8.48 mg, 0.0180 mmol) and RuPhos G3 (15.2 mg, 0.0180 mmol) was evacuated and backfilled with nitrogen three times. A solution of LiHMDS (1M in THF, 1.46 mL, 1.46 mmol) was added and the reaction mixture was heated at 70° C. for 18 hr. After cooling to RT the mixture was quenched by the addition of 1 M hydrochloric acid (5.0 mL) and was then basified with 2M aq. NaOH (10 mL). The aq layer was extracted with EtOAc (3×15 mL) and the combined organics dried and evaporated in vacuo. The crude product so obtained was purified by flash column chromatography (SiO$_2$, 24 g, 0-5% methanol (1% NH$_3$) in DCM, gradient elution) to afford a brown solid. The solid was triturated in diethyl ether (20 mL) and collected by filtration, washed with diethyl ether (10 mL) and dried at 40° C. in vacuo to afford the title compound, intermediate (XVc), as an off-white solid (72.0 mg, 47%); R$^t$ 2.19 min (Method a); m/z 420 (M+H)$^+$ (ES$^+$); $^1$H NMR δ: 2.07 (3H, s), 2.18 (3H, s), 2.87-2.89 (4H, m), 3.39-3.42 (4H, m), 6.60 (1H, s), 6.80 (1H, s), 7.06 (2H, d), 7.14-7.19 (2H, m), 7.76-7.80 (2H, m), 7.89 (2H, d), 8.81 (1H, s), 10.00 (1H, s).

4-(4-(4-(((3R,5R)-5-((1H-1,2,4-triazol-1-yl)methyl)-5-(2,4-difluorophenyl)tetrahydrofuran-3-yl)methoxy)-3-methylphenyl)piperazin-1-yl)benzamide

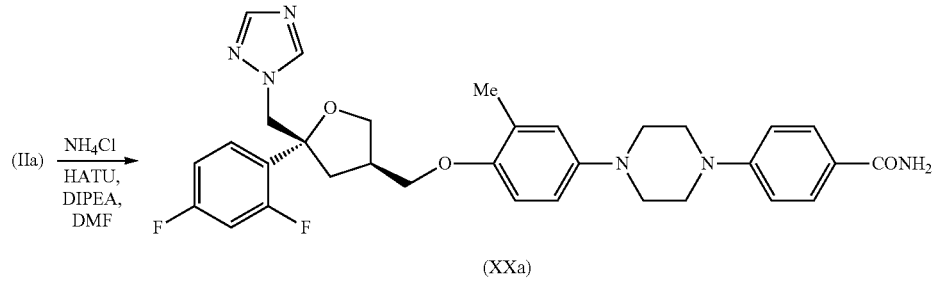 [SMILES: "NH4Cl" ; Cc1cc(N2CCN(c3ccc(C(N)=O)cc3)CC2)ccc1OC[C@@H]1CO[C@@](Cn2cncn2)(c2ccc(F)cc2F)C1]

To a solution of intermediate (IIa) (1.00 g, 1.70 mmol), DIPEA (1.78 mL, 10.2 mmol) and ammonium chloride (0.454 g, 8.48 mmol) in DMF (30 mL) at 0° C. was added HATU (1.30 g, 3.39 mmol) portionwise over 2 min. The reaction mixture was warmed to RT for 2 hr, then diluted with water (70 mL) and the resulting solid collected by filtration. The filter cake was washed with water (2×50 mL) and the solid dried in vacuo at 40° C. to give the title compound, intermediate (XXa) as an off-white powder (850 mg, 83%); R$^t$ 2.24 min (Method b); m/z 589 (M+H)$^+$ (ES$^+$); $^1$H NMR δ: 2.09 (3H, s), 2.16 (1H, dd), 2.37-2.42 (1H, m), 2.51-2.57 (1H, m), 3.11-3.14 (4H, m), 3.36-3.39 (4H, m), 3.68 (1H, dd), 3.74-3.79 (2H, m), 4.04 (1H, t), 4.58 (2H, dd), 6.75 (2H, br s), 6.85 (1H, br s), 6.97-7.04 (4H, br s), 7.26-7.34 (2H, m), 7.72 (1H, br s), 7.77 (3H, t), 8.34 (1H, s).

PREPARATION OF COMPOUND EXAMPLES OF THE INVENTION

Example 1: 4-(4-(4-(((3R,5R)-5-((1H-1,2,4-triazol-1-yl)methyl)-5-(2,4-difluorophenyl)tetra hydrofuran-3-yl)methoxy)-3-methylphenyl)piperazin-1-yl)-N-(4-fluorophenyl) benzamide 1. From Intermediate (IIa)

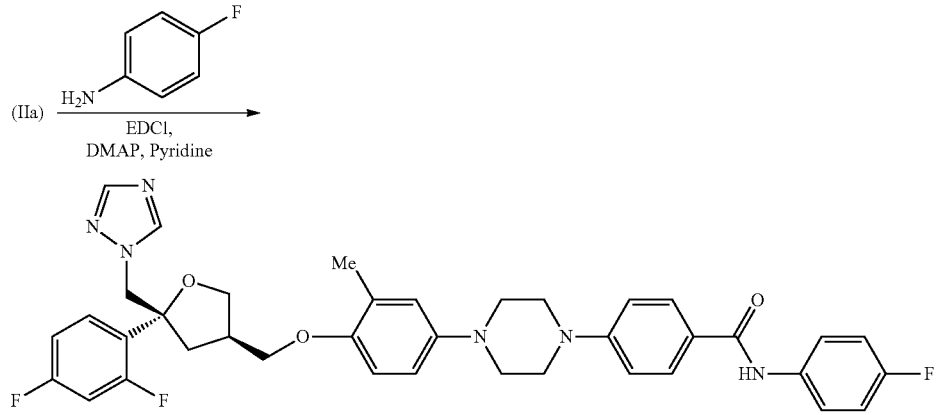

To a suspension of intermediate (11a) (2.50 g, 4.24 mmol), EDCl (1.63 g, 8.48 mmol) and DMAP (30 mg, 0.21 mmol) in pyridine (30 mL) was added 4-fluoroaniline (0.41 mL, 4.3 mmol) and the reaction mixture heated at 60° C. for 2 hr and then cooled to RT. Dilution of the mixture with water (60 mL) and stirring for 5 min produced a solid, which was collected by filtration and then washed with water (3×10 mL) and with diethyl ether (2×15 mL) to give a tan coloured powder. The crude product so obtained was purified by flash column chromatography (SiO$_2$, 40 g, 0-3% MeOH in DCM, gradient elution) to afford the title compound, Example 1, as a yellow solid (2.47 g, 85%); R$^t$ 2.60 min (Method a); m/z 683 (M+H)$^+$ (ES$^+$); $^1$H NMR δ: 2.10 (3H, s), 2.15 (1H, dd), 2.37-2.43 (1H, m), 2.53-2.58 (1H, m), 3.13-3.16 (4H, m), 3.42-3.44 (4H, m), 3.68 (1H, dd), 3.74-3.79 (2H, m), 4.05 (1H, dd), 4.58 (2H, dd), 6.76 (2H, br s), 6.86 (1H, br s), 6.99 (1H, td), 7.08 (2H, d), 7.16 (2H, t), 7.25-7.35 (2H, m), 7.76-7.80 (3H, m), 7.89 (2H, d), 8.34 (1H, s) and 10.00 (1H, s).

2. From Intermediate (XVc)

To a solution of intermediate (XVc) (19 mg, 0.047 mmol) in DMSO (1.5 mL) was added aq sodium hydroxide (1M, 98 µL, 0.098 mmol). The mixture was stirred at RT for 10 min and then treated with a solution of tosylate (XIa) (ex APIChem, Catalogue Number: AC-8330, 12.4 mg, 27.6 mmol) in DMSO (0.5 mL). The reaction mixture was stirred at 60° C. for 2 h, cooled to RT and water (10 mL) was added. The resulting mixture was extracted with EtOAc (3×10 mL) and the combined organic extracts were dried and evaporated in vacuo to afford a brown oil. The crude product so obtained was purified by flash column chromatography (SiO$_2$, 4 g, 0-2% MeOH in DCM, gradient elution) to afford the beige solid (23 mg). The product was repurified by flash column chromatography (SiO$_2$, 4.0 g, 0-50% EtOAc in DCM, gradient elution) to afford the title compound, Example 1, as an off-white solid (14 mg, 42%); R$^t$ 2.60 min (Method a); m/z 683 (M+H)$^+$ (ES$^+$).

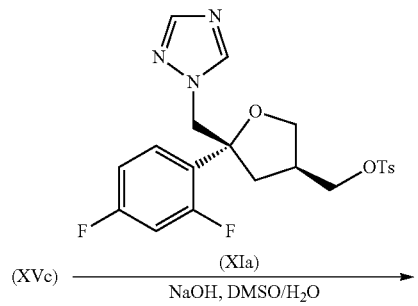

(XVc) —(XIa)/ NaOH, DMSO/H$_2$O→

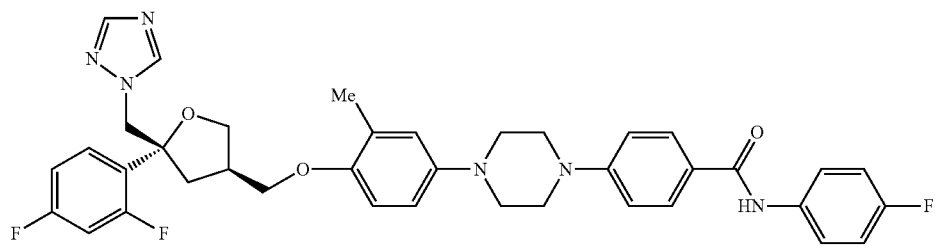

Example 2: 4-(4-(4-(((3R,5R)-5-((1H-1,2,4-triazol-1-yl)methyl)-5-(2,4-difluorophenyl) tetrahydrofuran-3-yl)methoxy)-3-methylphenyl)piperazin-1-yl)-N-(2,4-difluorophenyl) benzamide

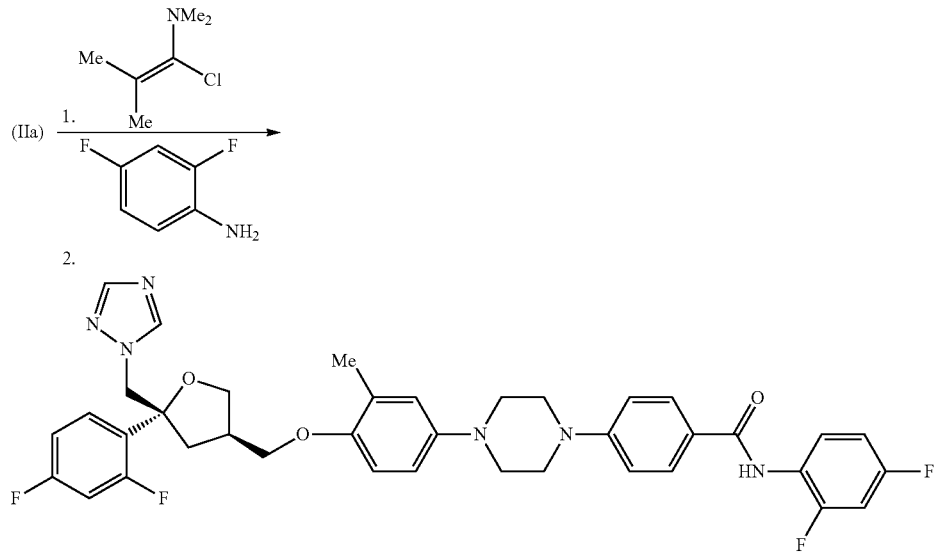

To a suspension of intermediate (11a) (74.0 mg, 0.125 mmol) in DCM (1.0 mL) was added 1-chloro-N,N,2-trimethylprop-1-en-1-amine (50.0 µL, 1.88 mmol) and the reaction mixture stirred at RT for 18 hr and then evaporated in vacuo. The resulting tan coloured solid was dissolved in DCM (1.0 mL) and was added to a solution of 2,4-difluoroaniline (19.0 µL, 0.188 mmol) in pyridine (0.5 mL). The reaction was stirred at RT for 3 h, then diluted with DCM (3.0 mL) and acidified to pH 2 by the addition of 1M hydrochloric acid (6.0 mL). The mixture was passed through a phase separator and the organics evaporated in vacuo. The crude product so obtained was purified by flash column chromatography (SiO$_2$, 12 g, 50-100% EtOAc in isohexane, gradient elution) to afford the title compound, Example 2, as an off-white solid (59.0 mg, 66%); R$^t$ 2.53 min (Method a); m/z 701 (M+H)$^+$ (ES$^+$); $^1$H NMR δ: 2.10 (3H, s), 2.16 (1H, dd), 2.37-2.43 (1H, m), 2.52-2.58 (1H, m), 3.13-3.16 (4H, m), 3.42-3.45 (4H, m), 3.68 (1H, dd), 3.74-3.80 (2H, m), 4.05 (1H, dd), 4.58 (2H, dd), 6.76 (2H, br s), 6.86 (1H, br s), 7.00 (1H, td), 7.06-7.12 (3H, m), 7.25-7.36 (3H, m), 7.56 (1H, td), 7.77 (1H, s), 7.89 (2H, d), 8.34 (1H, s), 9.81 (1H, s).

Example 3: 4-(4-(5-(((3R,5R)-5-((1H-1,2,4-triazol-1-yl)methyl)-5-(2,4-difluorophenyl)tetra hydrofuran-3-yl)methoxy)-6-methylpyridin-2-yl)piperazin-1-yl)-N-(4-fluorophenyl) benzamide

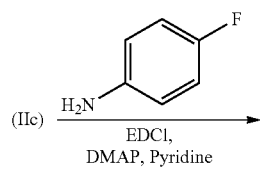

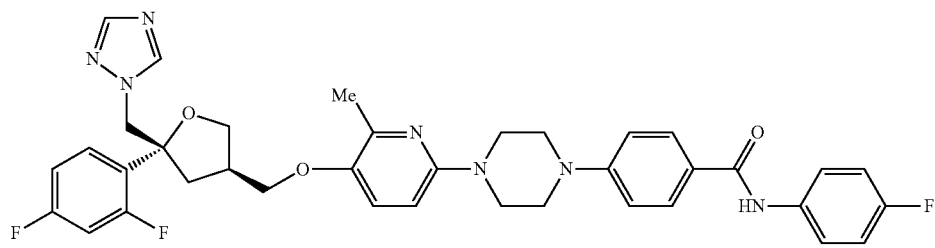

To a suspension of intermediate (11c) (100 mg, 0.169 mmol), EDCl (64.9 mg, 0.339 mmol) and DMAP (1.03 mg, 8.47 μmol) in pyridine (900 μL) was added 4-fluoroaniline (17.6 μL, 0.186 mmol). The reaction mixture was stirred at RT for 18 hr and was then poured into water (50 mL). The resulting solid was collected by filtration and was washed with water (10 mL) and with diethyl ether (10 mL) and dried in vacuo at 40° C. to give the title compound, Example 3, as an off-white powder (94.0 mg, 80%); R$^t$ 2.25 min (Method a); m/z 684 (M+H)$^+$ (ES$^+$); $^1$H NMR δ: 2.16 (1H, dd), 2.24 (3H, s), 2.37-2.43 (1H, m), 2.52-2.57 (1H, m), 3.39-3.42 (4H, m), 3.49-3.51 (4H, m), 3.69 (1H, dd), 3.74-3.78 (2H, m), 4.05 (1H, dd), 4.58 (2H, dd), 6.67 (1H, d), 7.00 (1H, td), 7.07 (2H, d), 7.13-7.22 (3H, m), 7.25-7.34 (2H, m), 7.76-7.79 (3H, m), 7.89 (2H, d), 8.34 (1H, s), 10.00 (1H, s).

Example 4: 4-(4-(4-(((3R,5R)-5-((1H-1,2,4-triazol-1-yl)methyl)-5-(2,4-difluorophenyl) tetrahydrofuran-3-yl)methoxy)-3-cyanophenyl)piperazin-1-yl)-N-(4-fluorophenyl) benzamide

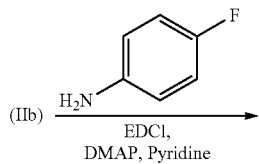

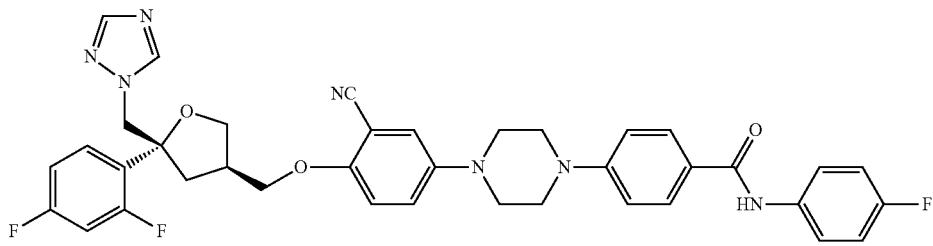

To a suspension of intermediate (11b) (72.0 mg, 0.120 mmol), EDCl (45.1 mg, 0.235 mmol) and DMAP (1.00 mg, 8.19 μmol) in pyridine (1.0 mL) was added 4-fluoroaniline (11.1 μL, 0.118 mmol) and the reaction mixture stirred at RT for 72 hr. The mixture was diluted with water (30 mL) and stirred for 5 min. The solid so formed was collected by filtration and purified by flash column chromatography (SiO$_2$, 4 g, 0-10% MeOH in DCM, gradient elution) to afford the title compound, Example 4, as a white solid (36.8 mg, 44%); R$^t$ 2.59 min (Method a); 694 m/z (M+H)$^+$ (ES$^+$); $^1$H NMR δ: 2.18 (1H, dd), 2.40-2.46 (1H, m), 2.56-2.64 (1H, m), 3.23-3.26 (4H, m), 3.43-3.45 (4H, m), 3.78-3.96 (3H, m), 4.04 (1H, dd), 4.59 (2H, dd), 6.98 (1H, td), 7.08-7.19 (5H, m), 7.25-7.37 (4H, m), 7.74-7.80 (3H, m), 7.89 (2H, d), 8.34 (1H, s), 10.03 (1H, s).

Example 5: 4-(4-(4-(((3R,5R)-5-((1H-1,2,4-triazol-1-yl)methyl)-5-(2,4-difluorophenyl) tetrahydrofuran-3-yl)methoxy)-2,5-dimethylphenyl)piperazin-1-yl)-N-(4-fluorophenyl) benzamide

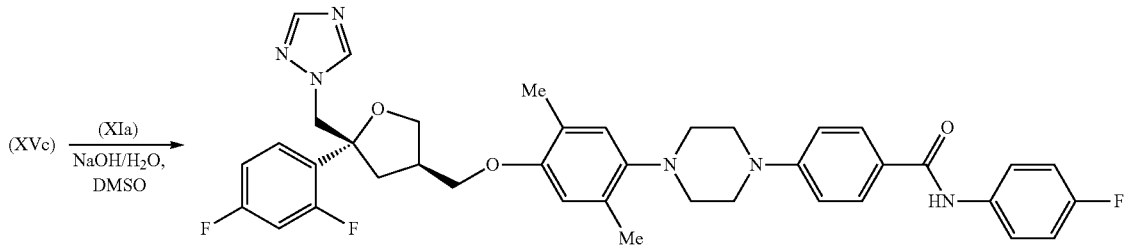 [SMILES: Cc1cc(N2CCN(c3ccc(C(=O)Nc4ccc(F)cc4)cc3)CC2)c(C)cc1OC[C@@H]1CO[C@@](Cn2cncn2)(c2ccc(F)cc2F)C1]

To a solution of intermediate (XVc) (70.0 mg, 0.167 mmol) in DMSO (1.0 mL) at 30° C. was added aq. NaOH (20.0 μL, 12.5 M, 0.250 mmol). After 30 min the tosylate (XIa) (83.0 mg, 0.184 mmol) was added and the reaction mixture was stirred at 30° C. for 18 hr, then cooled to RT and poured into water (15 mL). The resulting precipitate was collected by filtration, and was washed with water (20 mL) to provide a white solid. The crude product was purified by preparative HPLC (Method 2) to provide the title compound, Example 5 as a white solid (34.0 mg, 29%); $R^t$ 2.89 min (Method a); m/z 697 (M+H)$^+$ (ES$^+$); $^1$H NMR δ: 2.07 (3H, s), 2.16 (1H, dd), 2.25 (3H, s), 2.37-2.43 (1H, s), 2.53-2.57 (1H, m), 2.89-2.92 (4H, m), 3.41-3.44 (4H, m), 3.69 (1H, dd), 3.74-3.81 (2H, m), 4.05 (1H, dd), 4.58 (2H, dd), 6.71 (1H, s), 6.88 (1H, s), 7.00 (1H, td), 7.07 (2H, d), 7.16 (2H, t), 7.26-7.35 (2H, m), 7.76-7.80 (3H, m), 7.89 (2H, d), 8.35 (1H, s), 10.00 (1H, s).

Example 6: 4-(4-(4-(((3R,5R)-5-((1H-1,2,4-triazol-1-yl)methyl)-5-(2,4-difluorophenyl)tetra hydrofuran-3-yl)methoxy)-3-methylphenyl)piperazin-1-yl)-N-(5-fluoropyridin-2-yl) benzamide

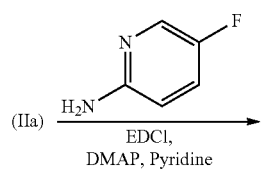

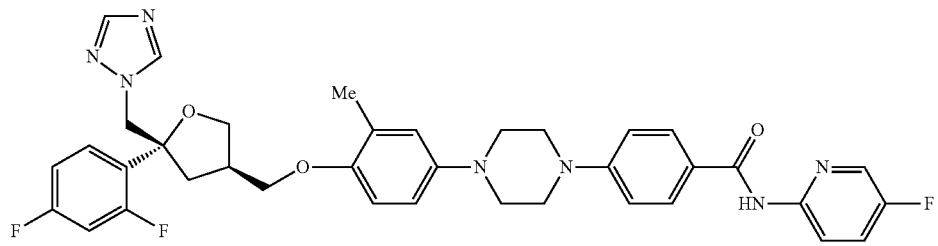

To a suspension of intermediate (11a) (100 mg, 0.17 mmol), EDCl (65 mg, 0.34 mmol) and DMAP (1.04 mg, 8.48 μmol) in pyridine (1.40 mL) was added 5-fluoropyridin-2-amine (23.9 mg, 0.25 mmol) and the reaction mixture was stirred at RT for 15 hr. The mixture was diluted with DCM (8.0 mL) and acidified by the addition of 1M hydrochloric acid (2.0 mL). The mixture was then passed through a phase separator and the organics evaporated in vacuo. The crude product was purified by preparative HPLC (Method 2) to provide the title compound, Example 6 as a white solid (41.0 mg, 34%); $R^t$ 2.51 min (Method a); m/z 684 (M+H)$^+$ (ES$^+$); $^1$H NMR δ: 2.10 (3H, s), 2.16 (1H, dd), 2.37-2.43 (1H, m), 2.52-2.58 (1H, m), 3.13-3.16 (4H, m), 3.43-3.46 (4H, m), 3.69 (1H, dd), 3.74-3.80 (2H, m), 4.05 (1H, dd), 4.58 (2H, dd), 6.76 (2H, br s), 6.86 (1H, br s), 7.00 (1H, td), 7.05 (2H, d), 7.25-7.34 (2H, m), 7.74-7.79 (2H, m), 7.97 (2H, d), 8.20 (1H, dd), 8.34 (1H, s), 8.37 (1H, d), 10.56 (1H, s).

Example 7: 4-(4-(5-(((3R,5R)-5-((1H-1,2,4-triazol-1-yl)methyl)-5-(2,4-difluorophenyl)tetra hydrofuran-3-yl)methoxy)-3-methylphenyl)piperazin-1-yl)-N-(5-cyanopyridin-2-yl) benzamide

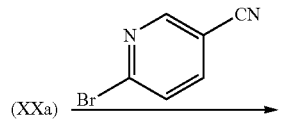

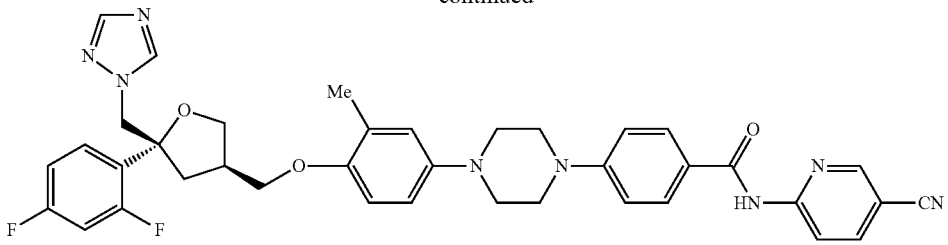

A vial charged with intermediate (XXa) (100 mg, 0.170 mmol), 6-bromonicotinonitrile (31.1 mg, 0.170 mmol), Xantphos (4.91 mg, 8.49 μmol, 5 mol %), tris(dibenzylideneacetone) dipalladium(0) (3.89 mg, 4.25 μmol, 2.5 mol %) and cesium carbonate (166 mg, 0.510 mmol) was evacuated and refilled with nitrogen three times before DMF (1.0 mL) was added. The reaction was heated to 100° C. for 18 hr, then cooled to RT and partitioned between DCM (15 mL) and brine (20 mL). The phases were separated and the organic layer was dried and concentrated in vacuo to give an oily residue which was triturated in methanol (6.0 mL). The resulting solid was isolated by filtration, washed with diethyl ether (10 mL) and dried in vacuo at 40° C. to give the crude solid. The trituration step was repeated with methanol (3.0 mL) and dried in vacuo to give title compound, Example 7, as an off-white powder (71.5 mg, 59%); $R^t$ 2.71 min (Method b); m/z 691 (M+H)$^+$ (ES$^+$); $^1$H NMR δ: 2.10 (3H, s), 2.16 (1H, dd), 2.37-2.43 (1H, m), 2.52-2.58 (1H, m), 3.13-3.15 (4H, m), 3.45-3.47 (4H, m), 3.69 (1H, dd), 3.74-3.79 (2H, m), 4.05 (1H, t), 4.58 (2H, dd), 6.76 (2H, br s), 6.86 (1H, br s), 7.00 (1H, td), 7.05 (2H, d), 7.25-7.34 (2H, m), 7.74-7.77 (2H, m), 7.99 (2H, d), 8.05 (1H, dd), 8.34 (1H, s), 8.48 (1H, dd), 10.92 (1H, s).

The following compound examples (Table 2) may be prepared by similar synthetic methods to the aforementioned examples or by methods described elsewhere herein:

TABLE 2

Additional Compound Examples of the Invention

Example No., Structure, Name, Purification Method and Analytical and Spectral Data

8

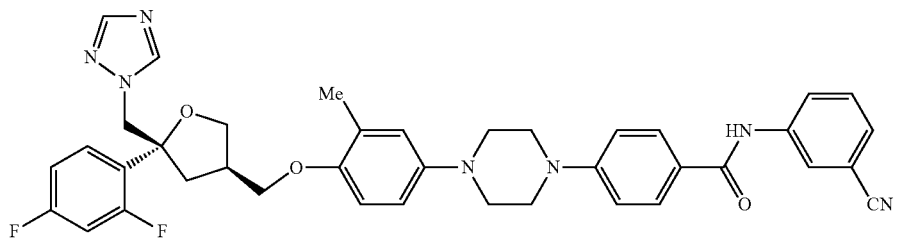

4-(4-(4-(((3R,5R)-5-((1H-1,2,4-triazol-1-yl)methyl)-5-(2,4-difluorophenyl)tetrahydrofuran-3-yl)methoxy)-3-methylphenyl)piperazin-1-yl)-N-(3-cyanophenyl)benzamide.
Purified by trituration from ether/DCM;
$R^t$ 2.53 min (Method a); m/z 690 (M + H)$^+$ (ES$^+$);
1H NMR δ: 2.10 (3H, s), 2.16 (1H, dd), 2.37-2.43 (1H, m), 2.52-2.58 (1H, m), 3.13-3.16 (4H, m), 3.44-3.46 (4H, m), 3.68 (1H, dd), 3.74-3.79 (2H, m), 4.05 (1H, dd), 4.58 (2H, dd), 6.76 (2H, br s), 6.86 (1H, br s), 7.01 (1H, td), 7.10 (2H, d), 7.26-7.34 (2H, m), 7.51-7.58 (2H, m), 7.77 (1H, s), 7.91 (2H, d), 8.05 (1H, td), 8.26-8.27 (1H, m), 8.35 (1H, s), 10.27 (1H, s).

9

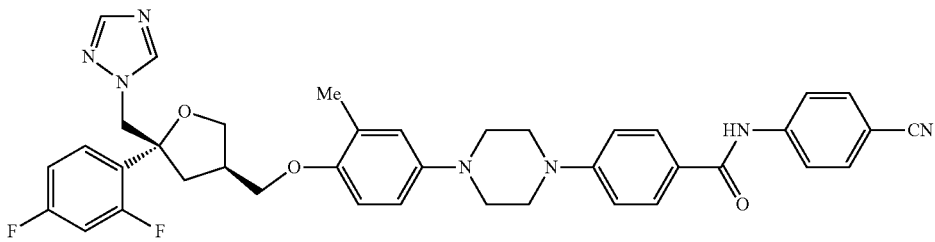 [SMILES: Cc1cc(N2CCN(c3ccc(C(=O)Nc4ccc(C#N)cc4)cc3)CC2)ccc1OC[C@@H]1CO[C@@](Cn2cncn2)(c2ccc(F)cc2F)C1]

4-(4-(4-(((3R,5R)-5-((1H-1,2,4-triazol-1-yl)methyl)-5-(2,4-difluorophenyl)tetrahydrofuran-3-yl)methoxy)-3-methylphenyl)piperazin-1-yl)-N-(4-cyanophenyl)benzamide.
Prep HPLC Method 2;
$R^t$ 2.53 min (Method a); m/z 690 (M + H)$^+$ (ES$^+$);
$^1$H NMR δ: 2.10 (3H, s), 2.16 (1H, dd), 2.37-2.43 (1H, m), 2.52-2.58 (1H, m), 3.13-3.16 (4H, m), 3.44-3.46 (4H, m), 3.68 (1H, dd), 3.74-3.79 (2H, m), 4.05 (1H, dd), 4.58 (2H, dd), 6.76 (2H, br s), 6.86 (1H, br s), 7.00 (1H, td), 7.09 (2H, d), 7.25-7.35 (4H, m), 7.77-7.80 (3H, m), 7.91 (2H, m), 7.97-8.01 (2H, m), 8.34 (1H, s), 10.34 (1H, s).

TABLE 2-continued

Additional Compound Examples of the Invention

Example No., Structure, Name, Purification Method and Analytical and Spectral Data

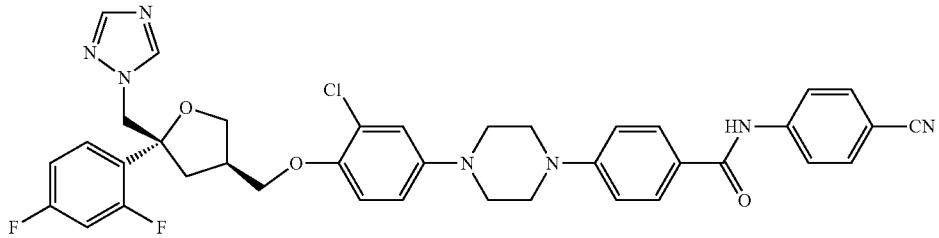

10

4-(4-(4-(((3R,5R)-5-((1H-1,2,4-triazol-1-yl)methyl)-5-(2,4-difluorophenyl)tetrahydrofuran-3-yl)methoxy)-3-chlorophenyl)piperazin-1-yl)-N-(4-cyanophenyl)benzamide.
Purified by column chromatography (SiO$_2$, 0-10% MeOH in DCM, gradient elution);
R$^t$ 2.79 min (Method a); m/z 710 (M + H)$^+$ (ES$^+$);
$^1$H NMR δ: 2.18 (1H, dd), 2.39-2.45 (1H, m), 2.53-2.61 (1H, m), 3.20-3.23 (4H, m), 3.45-3.48 (4H, m), 3.75-3.89 (3H, m), 4.05 (1H, dd), 4.59 (2H, dd), 6.93-7.03 (3H, m), 7.08-7.12 (3H, m), 7.26-7.33 (2H, m), 7.77-7.82 (3H, m), 7.92 (2H, d), 7.98-8.02 (2H, m), 8.34 (1H, s), 10.35 (1H, s).

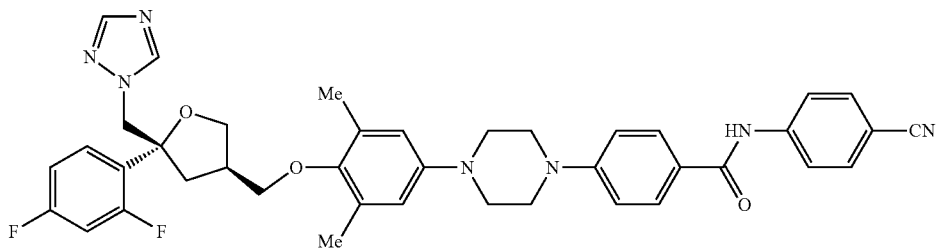 [SMILES: Cc1cc(N2CCN(c3ccc(C(=O)Nc4ccc(C#N)cc4)cc3)CC2)cc(C)c1OC[C@@H]1CO[C@@](Cn2cncn2)(c2ccc(F)cc2F)C1]

11

4-(4-(4-(((3R,5R)-5-((1H-1,2,4-triazol-1-yl)methyl)-5-(2,4-difluorophenyl)tetrahydrofuran-3-yl)methoxy)-3,5-dimethylphenyl)piperazin-1-yl)-N-(4-cyanophenyl)benzamide.
Purified by column chromatography (SiO$_2$, 0-10% MeOH in DCM, gradient elution);
R$^t$ 2.70 min (Method a); m/z 704 (M + H)$^+$ (ES$^+$);
$^1$H NMR δ: 2.09-2.15 (7H, m), 2.40-2.46 (1H, m), 2.52-2.58 (1H, m), 3.17-3.20 (4H, m), 3.41-3.45 (5H, m), 3.55 (1H, dd), 3.84 (1H, dd), 4.09 (1H, t), 4.58 (2H, br s), 6.65 (2H, br s), 7.01 (1H, td), 7.10 (2H, d), 7.26-7.34 (2H, m), 7.77-7.81 (3H, m), 7.91 (2H, d), 7.99 (2H, d), 8.34 (1H, s), 10.35 (1H, s).

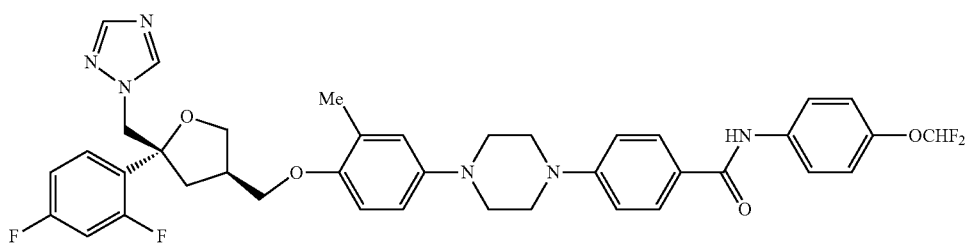

12

4-(4-(4-(((3R,5R)-5-((1H-1,2,4-triazol-1-yl)methyl)-5-(2,4-difluorophenyl)tetrahydrofuran-3-yl)methoxy)-3-methylphenyl)piperazin-1-yl)-N-(4-difluoromethoxyphenyl)benzamide.
Purified by column chromatography (SiO$_2$, 0-10% MeOH in DCM, gradient elution);
R$^t$ 2.59 min (Method a); m/z 731 (M + H)$^+$ (ES$^+$);
$^1$H NMR δ: 2.10 (3H, s), 2.16 (1H, dd), 2.37-2.43 (1H, m), 2.52-2.59 (1H, m), 3.12-3.18 (4H, m), 3.40-3.46 (4H, m), 3.68 (1H, dd), 3.75-3.79 (2H, m), 4.05 (1H, dd), 4.58 (2H, dd), 6.76 (2H, br s), 6.86 (1H, br s), 7.00 (1H, td), 7.08 (2H, d), 7.15 (2H, d), 7.25-7.35 (3H, m), 7.77-7.81 (3H, m), 7.90 (2H, d), 8.34 (1H, s), 10.03 (1H, s).

TABLE 2-continued

Additional Compound Examples of the Invention

Example No., Structure, Name, Purification Method and Analytical and Spectral Data

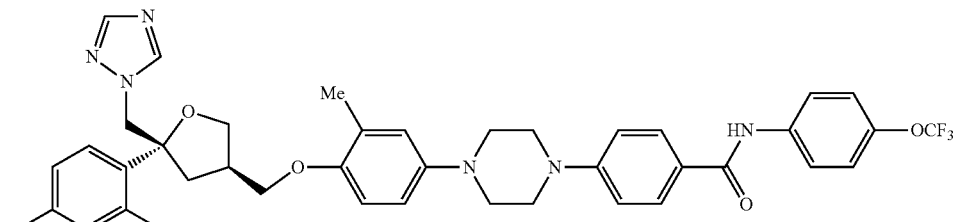

13

4-(4-(5-(((3R,5R)-5-((1H-1,2,4-triazol-1-yl)methyl)-5-(2,4-difluorophenyl)tetrahydrofuran-3-yl) methoxy)-3-methylphenyl)piperazin-1-yl)-N-(4-(trifluoromethoxy)phenyl)benzamide.
Purified by column chromatography (SiO$_2$, 0-10% MeOH in DCM, gradient elution);
R$^t$ 2.83 min (Method a); m/z 749 (M + H)$^+$ (ES$^+$);
$^1$H NMR δ: 2.10 (3H, s), 2.16 (1H, dd), 2.37-2.43 (1H, m), 2.53-2.58 (1H, m), 3.14-3.16 (4H, m), 3.42-3.45 (4H, m), 3.68 (1H, dd), 3.74-3.79 (2H, m), 4.05 (1H, dd), 4.58 (2H, dd), 6.76 (2H, br s), 6.86 (1H, br s), 7.00 (1H, td), 7.09 (2H, d), 7.25-7.35 (4H, m), 7.77 (1H, s), 7.87-7.91 (4H, m), 8.34 (1H, s), 10.13 (1H, s).

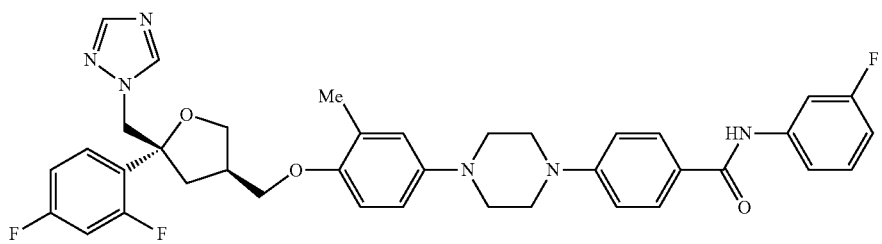 [SMILES: Cc1cc(N2CCN(c3ccc(C(=O)Nc4cccc(F)c4)cc3)CC2)ccc1OC[C@@H]1CO[C@@](Cn2cncn2)(c2ccc(F)cc2F)C1]

14

4-(4-(4-(((3R,5R)-5-((1H-1,2,4-triazol-1-yl)methyl)-5-(2,4-difluorophenyl)tetrahydrofuran-3-yl)methoxy)3-methylphenyl)piperazin-1-yl)-N-(3-fluorophenyl)benzamide.
Purified by column chromatography (SiO$_2$, 50-100% EtOAc in iso-hexane, gradient elution);
R$^t$ 2.60 min (Method a); m/z 683 (M + H)$^+$ (ES$^+$);
$^1$H NMR δ: 2.10 (3H, s), 2.16 (1H, dd), 2.37-2.43 (1H, m), 2.52-2.58 (1H, m), 3.13-3.16 (4H, m), 3.43-3.45 (4H, m), 3.68 (1H, dd), 3.74-3.79 (2H, m), 4.05 (1H, dd), 4.58 (2H, dd), 6.76 (2H, br s), 6.86-6.91 (2H, br m), 7.00 (1H, td), 7.09 (2H, d), 7.25-7.39 (3H, m), 7.54-7.57 (1H, m), 7.74-7.78 (2H, m), 7.90 (2H, d), 8.34 (1H, s), 10.12 (1H, s).

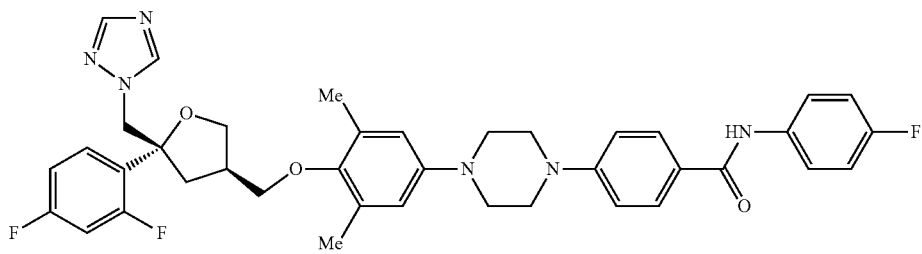 [SMILES: Cc1cc(N2CCN(c3ccc(C(=O)Nc4ccc(F)cc4)cc3)CC2)cc(C)c1OC[C@@H]1CO[C@@](Cn2cncn2)(c2ccc(F)cc2F)C1]

15

4-(4-(4-(((3R,5R)-5-((1H-1,2,4-triazol-1-yl)methyl)-5-(2,4-difluorophenyl)tetrahydrofuran-3-yl)methoxy)-3,5-dimethylphenyl)piperazin-1-yl)-N-(4-fluorophenyl)benzamide.
Purified by column chromatography (SiO$_2$, 0-10% MeOH in DCM, gradient elution);
R$^t$ 2.71 min (Method a); m/z 697 (M + H)$^+$ (ES$^+$);
1H NMR δ: 2.13 (1H, dd), 2.15 (6H, s), 2.40-2.46 (1H, m), 2.52-2.58 (1H, m), 3.17-3.20 (4H, m), 3.40-3.46 (5H, m), 3.56 (1H, dd), 3.84 (1H, t), 4.09 (1H, t), 4.55-4.62 (2H, m), 6.66 (2H, s), 7.01 (1H, td), 7.08 (2H, d), 7.17 (2H, t), 7.26-7.34 (2H, m), 7.76-7.80 (3H, m), 7.89 (2H, d), 8.34 (1H, s), 10.02 (1H, s).

TABLE 2-continued

Additional Compound Examples of the Invention

Example No., Structure, Name, Purification Method and Analytical and Spectral Data

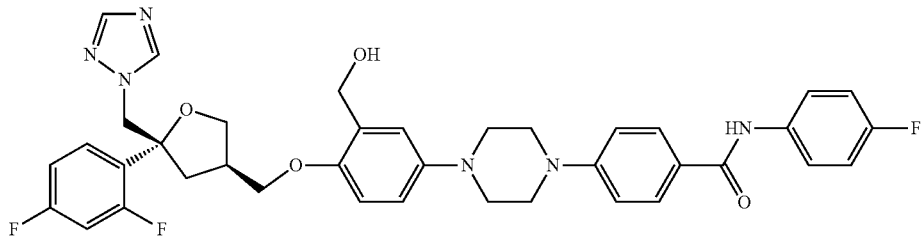 [SMILES: O=C(Nc1ccc(F)cc1)c1ccc(N2CCN(c3ccc(OC[C@@H]4CO[C@@](Cn5cncn5)(c5ccc(F)cc5F)C4)c(CO)c3)CC2)cc1]

16

4-(4-(4-(((3R,5R)-5-((1H-1,2,4-triazol-1-yl)methyl)-5-(2,4-difluorophenyl)tetrahydrofuran-3-yl)methoxy)-3-hydroxymethylphenyl)piperazin-1-yl)-N-(4-fluorophenyl)benzamide.
Purified by column chromatography (SiO$_2$, 0-10% MeOH in DCM, gradient elution);
R$^t$ 2.21 min (Method a); m/z 699 (M + H)$^+$ (ES$^+$);
$^1$H NMR δ: 2.16 (1H, dd), 2.36-2.42 (1H, m), 2.51-2.57 (1H, m), 3.15-3.17 (4H, m), 3.44-3.46 (4H, m), 3.68 (1H, dd), 3.73-3.80 (2H, m), 4.03 (1H, dd), 4.45 (2H, d), 4.58 (2H, d), 4.99 (1H, t), 6.77-6.83 (2H, m), 7.00 (1H, td), 7.07-7.10 (3H, m), 7.15-7.19 (2H, m), 7.26-7.33 (2H, m), 7.76-7.76 (3H, m), 7.89 (2H, d), 8.35 (1H, s), 10.02 (1H, s).

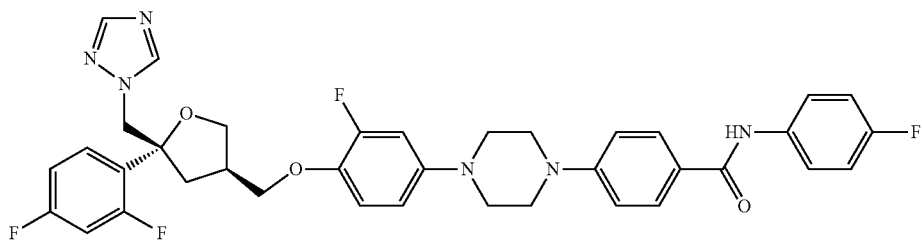 [SMILES: O=C(Nc1ccc(F)cc1)c1ccc(N2CCN(c3ccc(OC[C@@H]4CO[C@@](Cn5cncn5)(c5ccc(F)cc5F)C4)c(Cl)c3)CC2)cc1]

17

4-(4-(4-(((3R,5R)-5-((1H-1,2,4-triazol-1-yl)methyl)-5-(2,4-difluorophenyl)tetrahydrofuran-3-yl)methoxy)-3-fluorophenyl)piperazin-1-yl)-N-(4-fluorophenyl)benzamide.
Prep HPLC Method 2;
R$^t$ 2.67 min (Method a); m/z 687 (M + H)$^+$ (ES$^+$);
$^1$H NMR δ: 2.14 (1H, dd), 2.37-2.43 (1H, m), 2.53-2.58 (1H, m), 3.20-3.22 (4H, m), 3.42-3.44 (4H, m), 3.71-3.84 (3H, m), 4.02 (1H, dd), 4.58 (2H, dd), 6.73 (1H, dd), 6.92-7.02 (3H, m), 7.09 (2H, d), 7.17 (2H, t), 7.25-7.32 (2H, m), 7.76-7.80 (3H, m), 7.89 (2H, d), 8.34 (1H, s), 10.02 (1H, s).

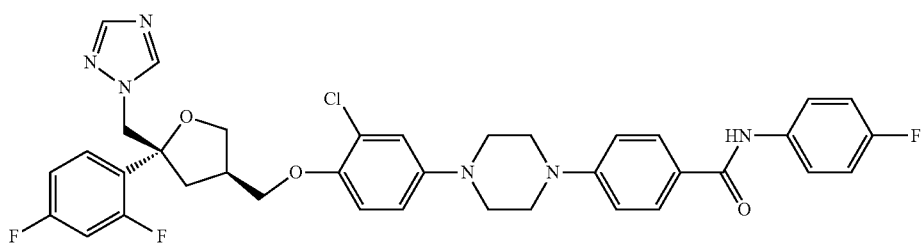

18

4-(4-(4-(((3R,5R)-5-((1H-1,2,4-triazol-1-yl)methyl)-5-(2,4-difluorophenyl)tetrahydrofuran-3-yl)methoxy)-3-chlorophenyl)piperazin-1-yl)-N-(4-fluorophenyl)benzamide.
Purified by column chromatography (SiO$_2$, 0-10% MeOH in DCM, gradient elution);
R$^t$ 2.80 min (Method a); m/z 703 (M + H)$^+$ (ES$^+$);
$^1$H NMR δ: 2.17 (1H, dd), 2.38-2.44 (1H, m), 2.53-2.60 (1H, m), 3.19-3.22 (4H, m), 3.42-3.44 (4H, m), 3.74-3.88 (3H, m), 4.04 (1H, dd), 4.59 (2H, dd), 6.92-7.02 (3H, m), 7.07-7.09 (3H, m), 7.14-7.19 (2H, m), 7.25-7.32 (2H, m), 7.76-7.80 (3H, m), 7.89 (2H, d), 8.33 (1H, s), 10.01 (1H, s).

TABLE 2-continued

Additional Compound Examples of the Invention

Example No., Structure, Name, Purification Method and Analytical and Spectral Data

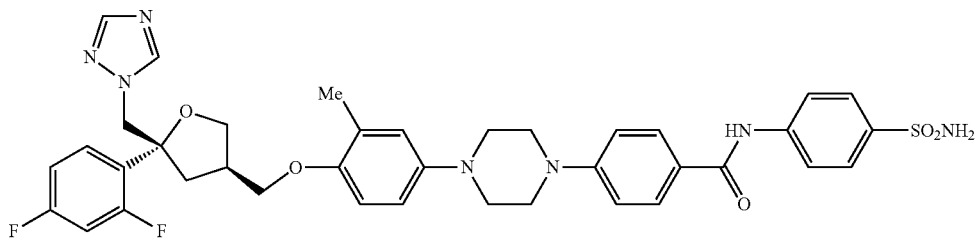 [SMILES: Cc1cc(N2CCN(c3ccc(C(=O)Nc4ccc(S(N)(=O)=O)cc4)cc3)CC2)ccc1OC[C@@H]1CO[C@@](Cn2cncn2)(c2ccc(F)cc2F)C1]

19

4-(4-(4-(((3R,5R)-5-((1H-1,2,4-triazol-1-yl)methyl)-5-(2,4-difluorophenyl)tetrahydrofuran-3-yl)methoxy)-3-methylphenyl)piperazin-1-yl)-N-(4-sulfamoylphenyl)benzamide.
Prep HPLC Method 3;
$R^t$ 2.19 min (Method a); m/z 744 (M + H)$^+$ (ES$^+$);
$^1$H NMR δ: 2.10 (3H, s), 2.16 (1H, dd), 2.37-2.43 (1H, m), 2.52-2.58 (1H, m), 3.14-3.16 (4H, m), 3.44-3.46 (4H, m), 3.68 (1H, dd), 3.74-3.80 (2H, m), 4.05 (1H, dd), 4.58 (2H, dd), 6.76 (2H, br s), 6.86 (1H, br s), 7.00 (1H, td), 7.09 (2H, d), 7.24-7.35 (4H, m), 7.76-7.79 (3H, m), 7.91-7.96 (4H, m), 8.34 (1H, s), 10.25 (1H, s).

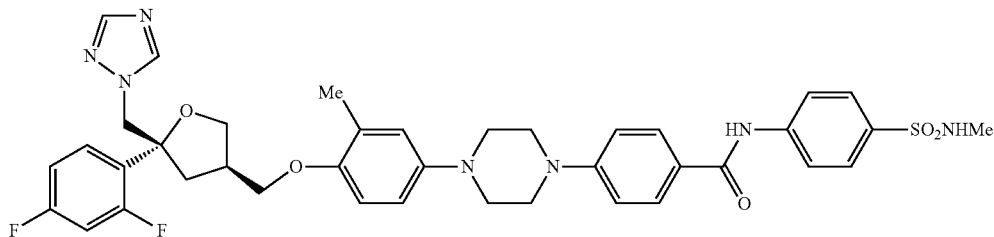

20

4-(4-(4-(((3R,5R)-5-((1H-1,2,4-triazol-1-yl)methyl)-5-(2,4-difluorophenyl)tetrahydrofuran-3-yl)methoxy)-3-methylphenyl)piperazin-1-yl)-N-(4-(N-methylsulfamoyl)phenyl)benzamide.
Purified by column chromatography (SiO$_2$, 0-10% MeOH in DCM, gradient elution);
$R^t$ 2.35 min (Method a); m/z 758 (M + H)$^+$ (ES$^+$);
$^1$H NMR δ: 2.10 (3H, s), 2.16 (1H, dd), 2.37-2.43 (4H, m), 2.52-2.58 (1H, m), 3.14-3.16 (4H, m), 3.44-3.46 (4H, m), 3.68 (1H, dd), 3.74-3.79 (2H, m), 4.05 (1H, dd), 4.58 (2H, dd), 6.76 (2H, br s), 6.86 (1H, br s), 7.00 (1H, td), 7.10 (2H, d), 7.25-7.35 (3H, m), 7.71-7.75 (2H, m), 7.77 (1H, s), 7.92 (2H, d), 7.98-8.01 (2H, m), 8.34 (1H, s), 10.29 (1H, s).

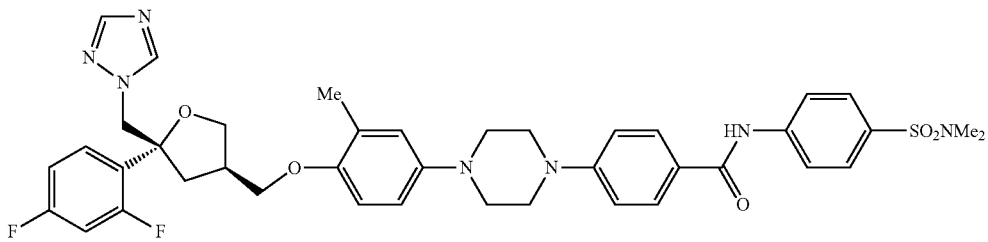

21

4-(4-(4-(((3R,5R)-5-((1H-1,2,4-triazol-1-yl)methyl)-5-(2,4-difluorophenyl)tetrahydrofuran-3-yl)methoxy)3-methylphenyl)piperazin-1-yl)-N-(4-(N,N-dimethylsulfamoylphenyl)benzamide.
Purified by column chromatography (SiO$_2$, 50-100% EtOAc in isohexane, gradient elution);
$R^t$ 2.52 min (Method a); m/z 772 (M + H)$^+$ (ES$^+$);
$^1$H NMR δ: 2.10 (3H, s), 2.16 (1H, dd), 2.37-2.43 (1H, m), 2.52-2.60 (7H, m), 3.14-3.16 (4H, m), 3.43-3.46 (4H, m), 3.68 (1H, dd), 3.74-3.79 (2H, m), 4.05 (1H, dd), 4.58 (2H, dd), 6.76 (2H, br s), 6.86 (1H, br s), 7.00 (1H, td), 7.10 (2H, d), 7.25-7.35 (2H, m), 7.71 (2H, d), 7.77 (1H, s), 7.92 (2H, d), 8.05 (2H, d), 8.34 (1H, s), 10.34 (1H, s).

TABLE 2-continued

Additional Compound Examples of the Invention

Example No., Structure, Name, Purification Method and Analytical and Spectral Data

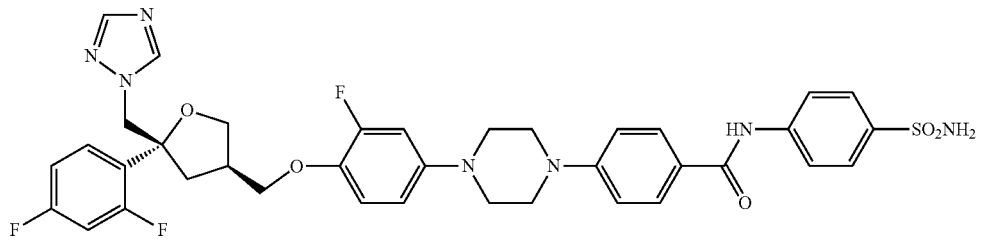

22

4-(4-(4-(((3R,5R)-5-((1H-1,2,4-triazol-1-yl)methyl)-5-(2,4-difluorophenyl)tetrahydrofuran-3-yl)methoxy)-3-fluorophenyl)piperazin-1-yl)-N-(4-sulfamoylphenyl)benzamide.
Purified by column chromatography (SiO$_2$, 50-100% EtOAc in isohexane, then 5-10% MeOH (1% NH$_3$) in DCM, gradient elution);
1H NMR δ: 2.15 (1H, dd), 2.37-2.43 (1H, m), 2.53-2.58 (1H, m), 3.20-3.22 (4H, m), 3.44-3.46 (4H, m), 3.72-3.78 (2H, m), 3.83 (1H, dd), 4.03 (1H, dd), 4.58 (2H, dd), 6.73 (1H, br d), 6.91-7.02 (3H, m), 7.10 (2H, d), 7.24-7.32 (4H, m), 7.76 (1H, s), 7.78 (2H, d), 7.91-7.96 (4H, m), 8.33 (1H, s), 10.25 (1H, s).

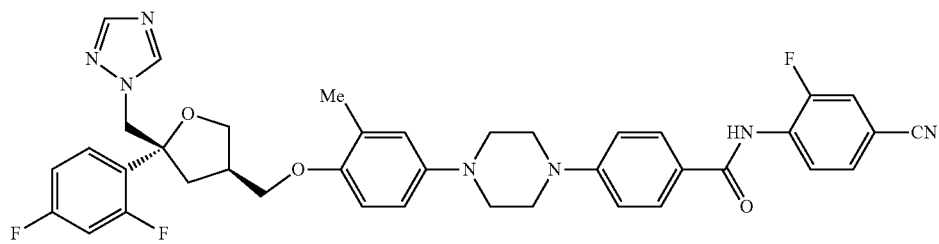

23

4-(4-(4-(((3R,5R)-5-((1H-1,2,4-triazol-1-yl)methyl)-5-(2,4-difluorophenyl)tetrahydrofuran-3-yl)methoxy)-3-methylphenyl)piperazin-1-yl)-N-(4-cyano-2-fluorophenyl)benzamide.
Purified by column chromatography (SiO$_2$, 0-10% MeOH in DCM, gradient elution);
R$^t$ 2.61 min (Method a); m/z 708 (M + H)$^+$ (ES$^+$);
$^1$H NMR δ: 2.10 (3H, s), 2.16 (1H, dd), 2.37-2.42 (1H, m), 2.52-2.58 (1H, m), 3.13-3.15 (4H, m), 3.44-3.46 (4H, m), 3.68 (1H, dd), 3.74-3.79(2H, m), 4.05 (1H, dd), 4.58 (2H, dd), 6.76 (2H, br s), 6.86 (1H, br s), 7.00 (1H, td), 7.09 (2H, d), 7.26-7.34 (2H, m), 7.70 (1H, dd), 7.77 (1H, s), 7.89-7.98 (4H, m), 8.35 (1H, s), 10.10 (1H, s).

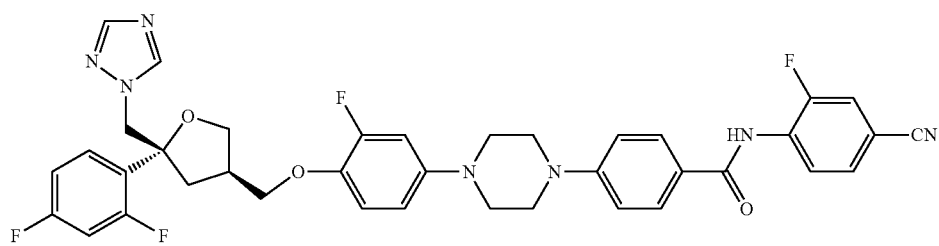 [SMILES: Cc1cc(N2CCN(c3ccc(C(=O)Nc4ccc(C#N)cc4F)cc3)CC2)ccc1OC[C@@H]1CO[C@@](Cn2cncn2)(c2ccc(F)cc2F)C1]

24

4-(4-(4-(((3R,5R)-5-((1H-1,2,4-triazol-1-yl)methyl)-5-(2,4-difluorophenyl)tetrahydrofuran-3-yl)methoxy)3-fluorophenyl)piperazin-1-yl)-N-(4-cyano-2-fluorophenyl)benzamide.
Purified by column chromatography (SiO$_2$, 50-100% EtOAc in isohexane, gradient elution);
R$^t$ 2.69 min (Method a); m/z 712 (M + H)$^+$ (ES$^+$);
$^1$H NMR δ: 2.14 (1H, dd), 2.37-2.43 (1H, m), 2.53-2.57 (1H, m), 3.20-3.22 (4H, m), 3.44-3.47 (4H, m), 3.72-3.84 (3H, m), 4.03 (1H, dd), 4.58 (2H, dd), 6.73 (1H, dd), 6.91-7.02 (3H, m), 7.09 (2H, d), 7.25-7.32 (2H, m), 7.70 (1H, dd), 7.76 (1H, s), 7.89-7.98 (4H, m), 8.33 (1H, s), 10.08 (1H, s).

| | |
|---|---|
| 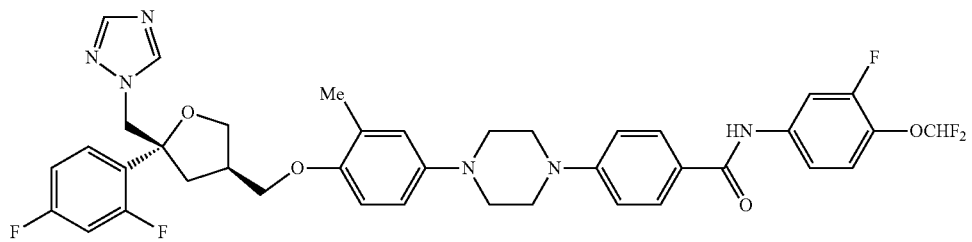 | 25 |

4-(4-(4-(((3R,5R)-5-((1H-1,2,4-triazol-1-yl)methyl)-5-(2,4-difluorophenyl)tetrahydrofuran-3-yl)methoxy)-3-methylphenyl)piperazin-1-yl)-N-(4-(difluoromethoxy)-3-fluorophenyl)benzamide.
Purified by column chromatography (SiO$_2$, 0-4% MeOH in DCM, gradient elution);
R$^t$ 2.51 min (Method a); m/z 749 (M + H)$^+$ (ES$^+$);
$^1$H NMR δ: 2.10 (3H, s), 2.16 (1H, dd), 2.37-2.43 (1H, m), 2.53-2.58 (1H, m), 3.12-3.18 (4H, m), 3.41-3.47 (4H, m), 3.68 (1H, dd), 3.74-3.78 (2H, m), 4.05 (1H, t), 4.58 (2H, dd), 6.76 (2H, br s), 6.86 (1H, br s), 6.97-7.02 (1H, m), 7.09 (2H, d), 7.17-7.35 (4H, m), 7.58 (1H, d), 7.77 (1H, s), 7.89-7.94 (3H, m), 8.34 (1H, s), 10.18 (1H, s).

| | |
|---|---|
| 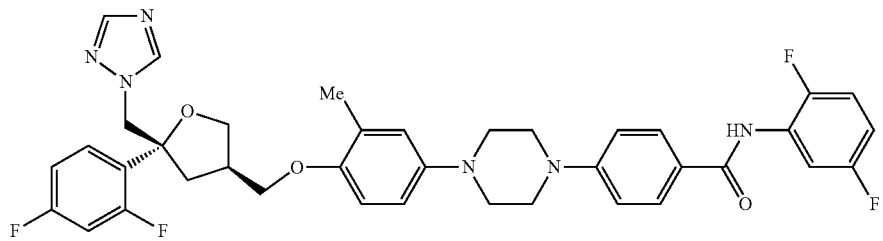 | 26 |

4-(4-(4-(((3R,5R)-5-((1H-1,2,4-triazol-1-yl)methyl)-5-(2,4-difluorophenyl)tetrahydrofuran-3-yl)methoxy)-3-methylphenyl)piperazin-1-yl)-N-(2,5-difluorophenyl)benzamide.
Purified by column chromatography (SiO$_2$, 0-3% MeOH in DCM, gradient elution);
R$^t$ 2.67 min (Method a); m/z 701 (M + H)$^+$ (ES$^+$);
$^1$H NMR δ: 2.12 (3H, s), 2.17 (1H, dd), 2.38-2.43 (1H, m), 2.54-2.60 (1H, m), 3.25-3.43 (4H, m), 3.53-3.62 (4H, m), 3.71-3.83 (3H, m), 4.05 (1H, dd), 4.58 (2H, dd), 6.86 (1H, br s), 6.98-7.12 (5H, m), 7.27-7.37 (4H, m), 7.56-7.61 (1H, m), 7.79 (1H, s), 7.91 (2H, d), 8.37 (1H, s), 9.93 (1H, s).

| | |
|---|---|
| 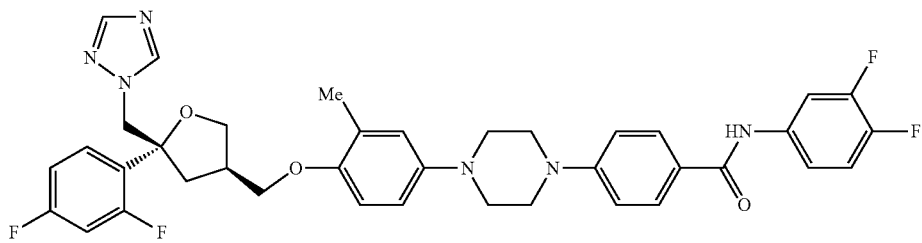 | 27 |

4-(4-(4-(((3R,5R)-5-((1H-1,2,4-triazol-1-yl)methyl)-5-(2,4-difluorophenyl)tetrahydrofuran-3-yl)methoxy)-3-methylphenyl)piperazin-1-yl)-N-(3,4-difluorophenyl)benzamide.
Purified by column chromatography (SiO$_2$, 0-10% MeOH in DCM, gradient elution);
R$^t$ 2.65 min (Method a); m/z 701 (M + H)$^+$ (ES$^+$);
$^1$H NMR δ: 2.10 (3H, s), 2.16 (1H, dd), 2.37-2.43 (1H, m), 2.52-2.58 (1H, m), 3.13-3.16 (4H, m), 3.43-3.45(4H, m), 3.68 (1H, dd), 3.74-3.79 (2H, m), 4.05 (1H, dd), 4.58 (2H, dd), 6.76 (2H, br s), 6.86 (1H, br s), 7.00 (1H, td), 7.08 (2H, d), 7.25-7.43 (3H, m), 7.52-7.56 (1H, m), 7.77 (1H, s), 7.89 (2H, d), 7.95 (1H, ddd), 8.34 (1H, s), 10.14 (1H, s).

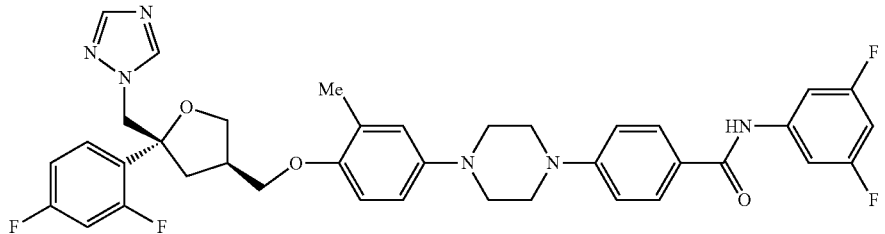 [SMILES: Cc1cc(N2CCN(c3ccc(C(=O)Nc4cc(F)cc(F)c4)cc3)CC2)ccc1OC[C@@H]1CO[C@@](Cn2cncn2)(c2ccc(F)cc2F)C1]

28

4-(4-(4-(((3R,5R)-5-((1H-1,2,4-triazol-1-yl)methyl)-5-(2,4-difluorophenyl)tetrahydrofuran-3-yl)methoxy)3-methylphenyl)piperazin-1-yl)-N-(3,5-difluorophenyl)benzamide.
Prep HPLC Method 1;
R$^t$ 2.73 min (Method a); m/z 701 (M + H)$^+$ (ES$^+$);
$^1$H NMR δ: 2.10 (3H, s), 2.16 (1H, dd), 2.37-2.43 (1H, m), 2.52-2.57 (1H, m), 3.13-3.16 (4H, m), 3.43-3.46 (4H, m), 3.68 (1H, m), 3.74-3.79 (2H, m), 4.05 (1H, dd), 4.58 (2H, dd), 6.76 (2H, br s), 6.86 (1H, br s), 6.90 (1H tt), 7.00 (1H, td), 7.09 (2H, d), 7.25-7.35 (2H, m), 7.55-7.58 (2H, m), 7.77 (1H, s), 7.89 (2H, d), 8.34 (1H, s), 10.26 (1H, s).

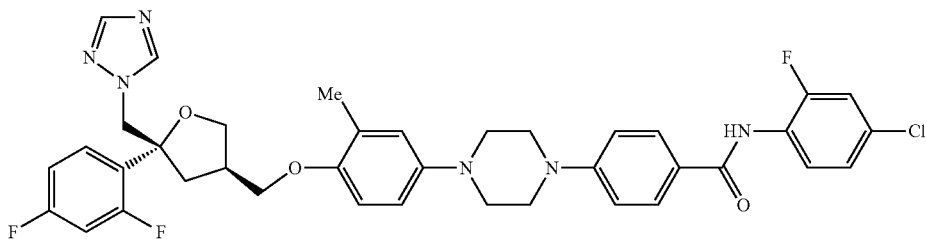 [SMILES: Cc1cc(N2CCN(c3ccc(C(=O)Nc4ccc(Cl)cc4F)cc3)CC2)ccc1OC[C@@H]1CO[C@@](Cn2cncn2)(c2ccc(F)cc2F)C1]

29

4-(4-(4-(((3R,5R)-5-((1H-1,2,4-triazol-1-yl)methyl)-5-(2,4-difluorophenyl)tetrahydrofuran-3-yl)methoxy)-3-methylphenyl)piperazin-1-yl)-N-(4-chloro-2-fluorophenyl)benzamide.
Prep HPLC Method 1;
Rt 2.74 min (Method a); m/z 717 (M + H)$^+$ (ES+);
$^1$H NMR δ: 2.10 (3H, s), 2.16 (1H, dd), 2.37-2.43 (1H, m), 2.52-2.58 (1H, m), 3.13-3.16 (4H, m), 3.43-3.45 (4H, m), 3.68 (1H, dd), 3.74-3.79 (2H, m), 4.05 (1H, dd), 4.58 (2H, dd), 6.76 (2H, br s), 6.86 (1H, br s), 7.00 (1H, td), 7.07 (2H, d), 7.25-7.35 (3H, m), 7.51 (1H, dd), 7.63 (1H, t), 7.77 (1H, s), 7.89 (2H, d), 8.34 (1H, s), 9.87 (1H, s).

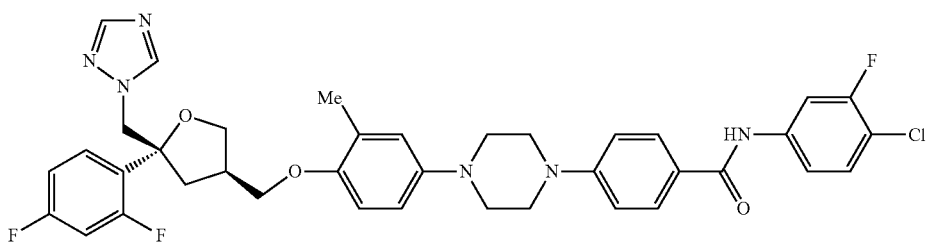 [SMILES: Cc1cc(N2CCN(c3ccc(C(=O)Nc4ccc(Cl)c(F)c4)cc3)CC2)ccc1OC[C@@H]1CO[C@@](Cn2cncn2)(c2ccc(F)cc2F)C1]

30

4-(4-(4-(((3R,5R)-5-((1H-1,2,4-triazol-1-yl)methyl)-5-(2,4-difluorophenyl)tetrahydrofuran-3-yl)methoxy)-3-methylphenyl)piperazin-1-yl)-N-(4-chloro-3-fluorophenyl)benzamide.
Purified by precipitation with water, filtration and washing with water;
R$^t$ 2.80 min (Method a); m/z 717 (M + H)$^+$ (ES$^+$);
$^1$H NMR δ: 2.10 (3H, s), 2.16 (1H, dd), 2.37-2.43 (1H, m), 2.52-2.58 (1H, m), 3.13-3.16 (4H, m), 3.43-3.46 (4H, m), 3.68 (1H, dd), 3.74-3.79 (2H, m), 4.05 (1H, dd), 4.58 (2H, dd), 6.76 (2H, br s), 6.86 (1H, br s), 7.00 (1H, td), 7.09 (2H, d), 7.25-7.35 (2H, m), 7.53 (1H, t), 7.61 (1H, dd), 7.77 (1H, s), 7.89 (2H, d), 7.97 (1H, dd), 8.34 (1H, s), 10.23 (1H, s).

TABLE 2-continued

Additional Compound Examples of the Invention

Example No., Structure, Name, Purification Method and Analytical and Spectral Data

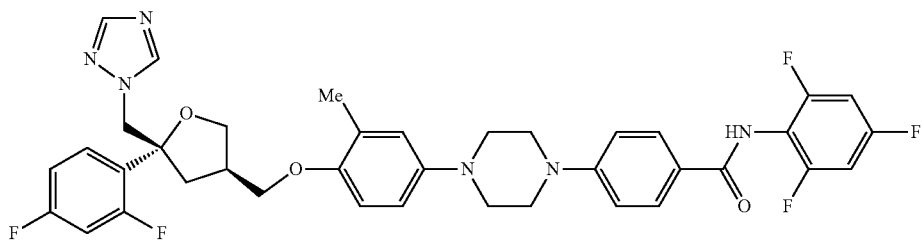 [SMILES: Cc1cc(N2CCN(c3ccc(C(=O)Nc4c(F)cc(F)cc4F)cc3)CC2)ccc1OC[C@@H]1CO[C@@](Cn2cncn2)(c2ccc(F)cc2F)C1]

31

4-(4-(4-(((3R,5R)-5-((1H-1,2,4-triazol-1-yl)methyl)-5-(2,4-difluorophenyl)tetrahydrofuran-3-yl)methoxy)3-methylphenyl)piperazin-1-yl)-N-(2,4,6-trifluorophenyl)benzamide.
Purified by column chromatography (SiO$_2$, 50-100% EtOAc in isohexane, gradient elution);
R$^t$ 2.48 min (Method a); m/z 719 (M + H)$^+$ (ES$^+$);
$^1$H NMR δ: 2.10 (3H, s), 2.16 (1H, dd), 2.37-2.43 (1H, m), 2.52-2.57 (1H, m), 2.92 (2H, t), 3.13-3.16 (4H, m), 3.43-3.45 (4H, m), 3.68 (1H, dd), 3.74-3.79 (2H, m), 4.05 (1H, t), 4.58 (2H, dd), 6.76 (2H, br s), 6.86 (1H, br s), 7.00 (1H, td), 7.09 (2H, d), 7.26-7.34 (2H, m), 7.77 (1H, s), 7.89 (2H, d), 8.34 (1H, s), 9.79 (1H, s).

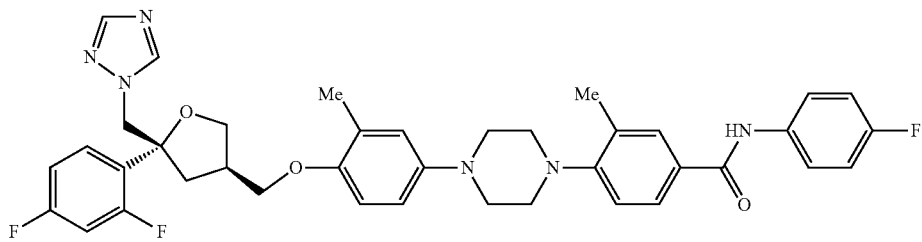 [SMILES: COc1cc(C(=O)Nc2ccc(F)cc2)ccc1N1CCN(c2ccc(OC[C@@H]3CO[C@@](Cn4cncn4)(c4ccc(F)cc4F)C3)c(C)c2)CC1]

32

4-(4-(4-(((3R,5R)-5-((1H-1,2,4-triazol-1-yl)methyl)-5-(2,4-difluorophenyl)tetrahydrofuran-3-yl)methoxy)-3-methylphenyl)piperazin-1-yl)-N-(4-fluorophenyl)-3-methylbenzamide.
Purified by column chromatography (SiO$_2$, 0-4% MeOH in DCM, gradient elution);
R$^t$ 2.58 min (Method a); m/z 697 (M + H)$^+$ (ES$^+$);
$^1$H NMR δ: 2.10 (3H, s), 2.17 (1H, dd), 2.35 (3H, s), 2.37-2.43 (1H, m), 2.52-2.58 (1H, m), 3.05-3.07 (4H, m), 3.17-3.19 (4H, m), 3.69 (1H, dd), 3.75-3.80 (2H, m), 4.06 (1H, dd), 4.58 (2H, dd), 6.76 (2H, br s), 6.86 (1H, br s), 7.00 (1H, td), 7.14-7.20 (3H, m), 7.25-7.35 (2H, m), 7.76-7.80 (5H, m), 8.34 (1H, s), 10.12 (1H, s).

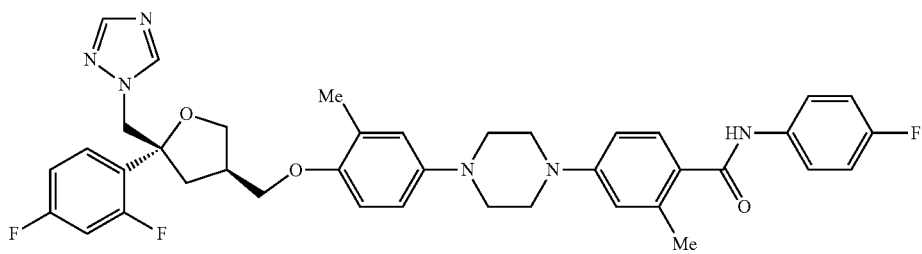

33

4-(4-(4-(((3R,5R)-5-((1H-1,2,4-triazol-1-yl)methyl)-5-(2,4-difluorophenyl)tetrahydrofuran-3-yl)methoxy)-3-methylphenyl)piperazin-1-yl)-N-(4-fluorophenyl)-2-methylbenzamide.
Purified by column chromatography (SiO$_2$, 0-10% MeOH in DCM, gradient elution);
R$^t$ 2.57 min (Method a); m/z 697 (M + H)$^+$ (ES$^+$);
$^1$H NMR δ: 2.10 (3H, s), 2.16 (1H, dd), 2.37-2.43 (4H, m), 2.52-2.58 (1H, m), 3.13-3.15 (4H, m), 3.34-3.37 (4H, m), 3.68 (1H, dd), 3.74-3.79 (2H, m), 4.05 (1H, t), 4.58 (2H, dd), 6.76 (2H, br s), 6.85-6.90 (3H, m), 7.00 (1H, td), 7.13-7.17 (2H, m), 7.25-7.35 (2H, m), 7.40 (1H, d), 7.72-7.77 (3H, m), 8.34 (1H, s), 10.09 (1H, s).

TABLE 2-continued

Additional Compound Examples of the Invention

Example No., Structure, Name, Purification Method and Analytical and Spectral Data

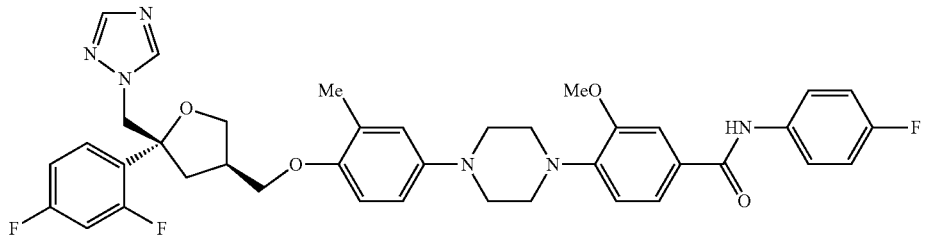

34

4-(4-(4-(((3R,5R)-5-((1H-1,2,4-triazol-1-yl)methyl)-5-(2,4-difluorophenyl)tetrahydrofuran-
3-yl)methoxy)3-methylphenyl)piperazin-1-yl)-N-(4-fluorophenyl)-3-methoxybenzamide.
Purified by column chromatography (SiO$_2$, 50-100% EtOAc in isohexane, gradient elution);
R$^t$ 2.43 min (Method a); m/z 713 (M + H)$^+$ (ES$^+$);
$^1$H NMR δ: 2.10 (3H, s), 2.16 (1H, dd), 2.37-2.43 (1H, m), 2.52-2.56 (1H, m), 3.14-3.22 (8H, m), 3.68 (1H, dd), 3.75-3.80 (2H, m), 3.89 (3H, s), 4.05 (1H, dd), 4.58 (2H, dd), 6.75 (2H, br s), 6.85 (1H, br s), 6.97-7.03 (2H, m), 7.19 (2H, t), 7.25-7.35 (2H, m), 7.51 (1H, d), 7.59 (1H, dd), 7.75-7.79 (3H, m), 8.34 (1H, s), 10.10 (1H, s).

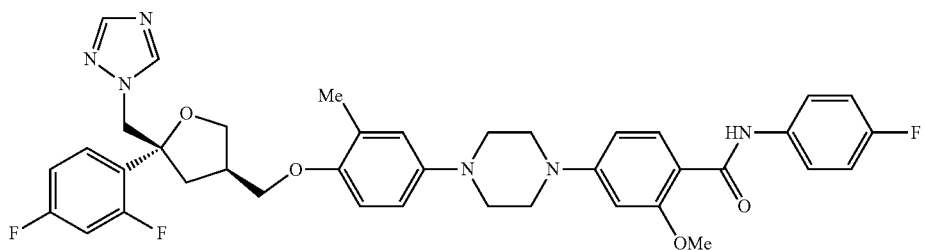 [SMILES: COc1cc(N2CCN(c3ccc(OC[C@@H]4CO[C@@](Cn5cncn5)(c5ccc(F)cc5F)C4)c(C)c3)CC2)ccc1C(=O)Nc1ccc(F)cc1]

35

4-(4-(4-(((3R,5R)-5-((1H-1,2,4-triazol-1-yl)methyl)-5-(2,4-difluorophenyl)tetrahydrofuran-
3-yl)methoxy)-3-methylphenyl)piperazin-1-yl)-N-(4-fluorophenyl)-2-methoxybenzamide.
Purified by column chromatography (SiO$_2$, 0-4% MeOH in DCM, gradient elution);
R$^t$ 2.47 min (Method a); m/z 713 (M + H)$^+$ (ES$^+$);
$^1$H NMR δ: 2.10 (3H, s), 2.16 (1H, dd), 2.37-2.43 (1H, m), 2.52-2.58 (1H, m), 3.13-3.16 (4H, m), 3.44-3.46 (4H, m), 3.68 (1H, dd), 3.74-3.79 (2H, m), 3.99 (3H, s), 4.05 (1H, dd), 4.58 (2H, dd), 6.65 (1H, d), 6.69 (1H, dd), 6.76 (2H, br s), 6.86 (1H, br s), 7.00 (1H, td), 7.16 (2H, t), 7.25-7.35 (2H, m), 7.73-7.77 (4H, m), 8.34 (1H, s), 9.88 (1H, s).

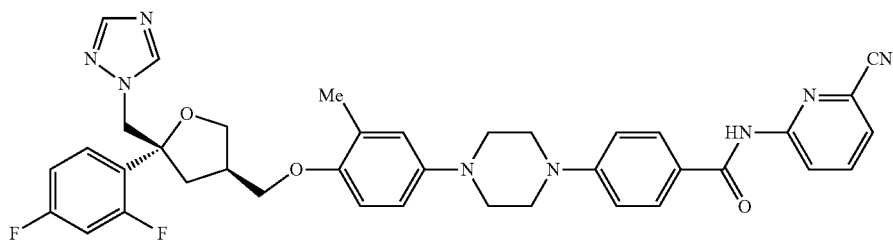

36

4-(4-(4-(((3R,5R)-5-((1H-1,2,4-triazol-1-yl)methyl)-5-(2,4-difluorophenyl)tetrahydrofuran-
3-yl)methoxy)3-methylphenyl)piperazin-1-yl)-N-(6-cyanopyridin-2-yl)benzamide.
Purified by trituration from MeOH;
R$^t$ 2.75 min (Method a); m/z 691 (M + H)$^+$ (ES$^+$);
$^1$H NMR δ: 2.10 (3H, s), 2.16 (1H, dd), 2.37-2.42 (1H, m), 2.52-2.58 (1H, m), 3.12-3.14 (4H, m), 3.44-3.47 (4H, m), 3.67 (1H, dd), 3.74-378 (2H, m), 4.04 (1H, t), 4.58 (2H, dd), 6.75 (2H, br s), 6.86 (1H, br s), 6.97-7.06 (3H, m), 7.26-7.34 (2H, m), 7.75-7.77 (2H, m), 7.99 (2H, d), 8.05 (1H, dd), 8.35 (1H, s), 8.48 (1H, dd), 10.94 (1H, s).

| | |
|---|---|
| 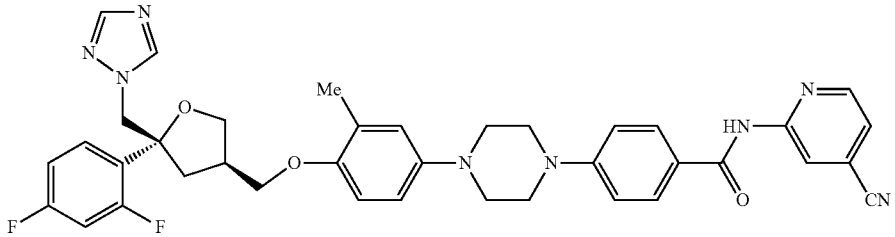 | 37 |

4-(4-(4-(((3R,5R)-5-((1H-1,2,4-triazol-1-yl)methyl)-5-(2,4-difluorophenyl)tetrahydrofuran-3-yl)methoxy)-3-methylphenyl)piperazin-1-yl)-N-(4-cyanopyridin-2-yl)benzamide.
Purified by precipitation from MeOH;
$R^t$ 2.72 min (Method b); m/z 691 (M + H)$^+$ (ES$^+$);
1H NMR δ: 2.10 (3H, s), 2.16 (1H, dd), 2.37-2.43 (1H, m), 2.52-2.58 (1H, m), 3.13-3.15 (4H, m), 3.45-3.47 (4H, m), 3.68 (1H, dd), 3.74-3.79 (2H, m), 4.05 (1H, t), 4.58 (2H, dd), 6.76 (2H, br s), 6.86 (1H, br s), 7.00 (1H, td), 7.06 (2H, d), 7.25-7.34 (2H, m), 7.57 (1H, dd), 7.77 (1H, s), 7.99 (2H, d), 8.34 (1H, s), 8.51 (1H, br s), 8.62 (1H, dd), 10.92 (1H, s).

| | |
|---|---|
| 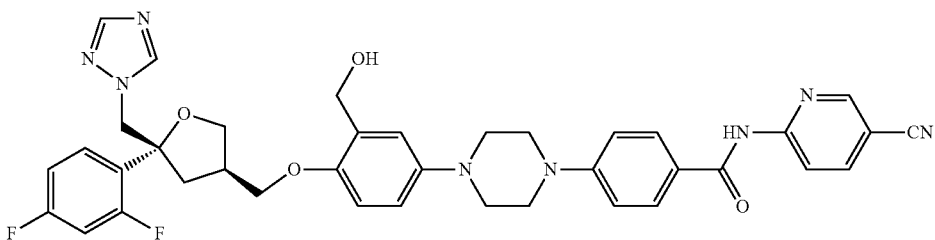 [SMILES: N#Cc1ccc(NC(=O)c2ccc(N3CCN(c4ccc(OC[C@@H]5CO[C@@](Cn6cncn6)(c6ccc(F)cc6F)C5)c(CO)c4)CC3)cc2)nc1] | 38 |

4-(4-(4-(((3R,5R)-5-((1H-1,2,4-triazol-1-yl)methyl)-5-(2,4-difluorophenyl)tetrahydrofuran-3-yl)methoxy)-3-hydroxymethylphenyl)piperazin-1-yl)-N-(5-cyanopyridin-2-yl)benzamide.
Purified by column chromatography (SiO$_2$, 0-10% MeOH in DCM, gradient elution);
$R^t$ 2.19 min (Method a); m/z 707 (M + H)$^+$ (ES$^+$);
$^1$H NMR δ: 2.16 (1H, dd), 2.37-2.42 (1H, m), 2.52-2.57 (1H, m), 3.14-3.17 (4H, m), 3.47-3.49 (4H, m), 3.67-3.80 (3H, m), 4.04 (1H, dd), 4.45 (2H, d), 4.58 (2H, dd), 4.97 (1H, t), 6.77-6.83 (2H, m), 6.99 (1H, td), 7.05-7.08 (3H, m), 7.25-7.33 (2H, m), 7.77 (1H, s), 7.99 (2H, d), 8.27 (1H, dd), 8.34-8.37 (2H, m), 8.84 (1H, dd), 10.99 (1H, s).

| | |
|---|---|
| 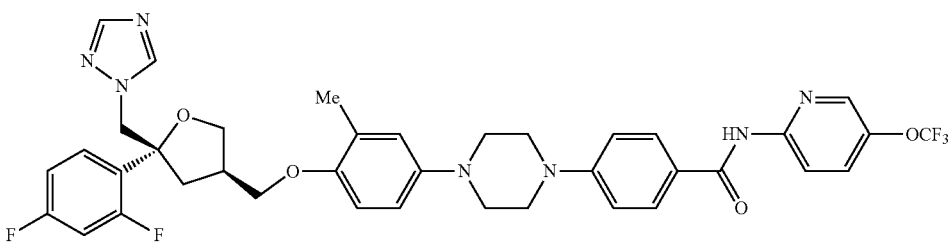 [SMILES: Cc1cc(N2CCN(c3ccc(C(=O)Nc4ccc(OC(F)(F)F)cn4)cc3)CC2)ccc1OC[C@@H]1CO[C@@](Cn2cncn2)(c2ccc(F)cc2F)C1] | 39 |

4-(4-(4-(((3R,5R)-5-((1H-1,2,4-triazol-1-yl)methyl)-5-(2,4-difluorophenyl)tetrahydrofuran-3-yl)methoxy)-3-methylphenyl)piperazin-1-yl)-N-(5-(trifluoromethoxy)pyridin-2-yl)benzamide
Purified by column chromatography (SiO$_2$, 0-100% EtOAc in DCM, gradient elution);
$R^t$ 2.82 min (Method a); m/z 750 (M + H)$^+$ (ES$^+$);
$^1$H NMR δ 2.10 (3H, s), 2.16 (1H, dd), 2.37-2.42 (1H, m), 2.53-2.58 (1H, m), 3.13-3.15 (4H, m), 3.44-3.46 (4H, m), 3.68 (1H, dd), 3.74-3.79 (2H, m), 4.05 (1H, dd), 4.58 (2H, dd), 6.76 (2H, br s), 6.86 (1H, br s), 7.00 (1H, td), 7.06 (2H, d), 7.25-7.34 (2H, m), 7.77 (1H, s), 7.93 (1H, dd), 7.98 (2H, d), 8.31 (1H, d), 8.34 (1H, s), 8.47 (1H, d), 10.74 (1H, s).

TABLE 2-continued

Additional Compound Examples of the Invention

Example No., Structure, Name, Purification Method and Analytical and Spectral Data

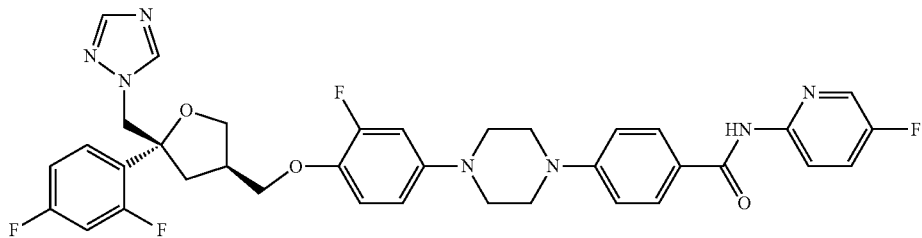 [SMILES: O=C(Nc1ccc(F)cn1)c1ccc(N2CCN(c3ccc(OC[C@@H]4CO[C@@](Cn5cncn5)(c5ccc(F)cc5F)C4)c(F)c3)CC2)cc1]

40

4-(4-(4-(((3R,5R)-5-((1H-1,2,4-triazol-1-yl)methyl)-5-(2,4-difluorophenyl)tetrahydrofuran-3-yl)methoxy)-3-fluorophenyl)piperazin-1-yl)-N-(5-fluoropyridin-2-yl)benzamide.
Purified by column chromatography (SiO$_2$, 0-10% MeOH in DCM, gradient elution);
R$^r$ 2.63 min (Method a); m/z 688 (M + H)$^+$ (ES$^+$);
$^1$H NMR δ: 2.14 (1H, dd), 2.37-2.43 (1H, m), 2.53-2.59 (1H, m), 3.19-3.21 (4H, m), 3.43-3.45 (4H, m), 3.72-3.84 (3H, m), 4.03 (1H, dd), 4.58 (2H, d), 6.73 (1H, dd), 6.90-7.02 (3H, m), 7.05 (2H, d), 7.25-7.31 (2H, m), 7.74-7.79 (2H, m), 7.97 (2H, d), 8.21 (1H, dd), 8.33 (1H, s), 8.37 (1H, d), 10.57 (1H, s).

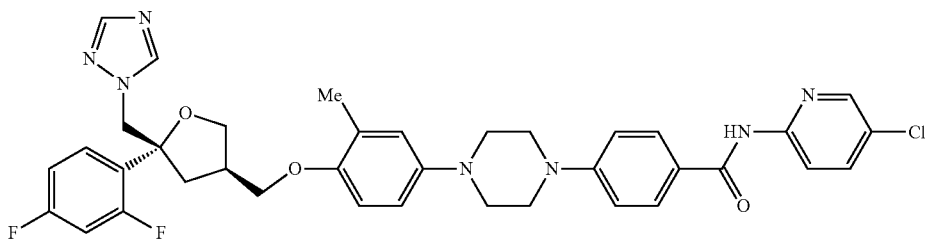 [SMILES: Cc1cc(N2CCN(c3ccc(C(=O)Nc4ccc(Cl)cn4)cc3)CC2)ccc1OC[C@@H]1CO[C@@](Cn2cncn2)(c2ccc(F)cc2F)C1]

41

4-(4-(4-(((3R,5R)-5-((1H-1,2,4-triazol-1-yl)methyl)-5-(2,4-difluorophenyl)tetrahydrofuran-3-yl)methoxy)-3-methylphenyl)piperazin-1-yl)-N-(5-chloropyridin-2-yl)benzamide.
Purified by column chromatography (SiO$_2$, 0-10% MeOH in DCM, gradient elution);
R$^r$ 2.72 min (Method a); m/z 701 (M + H)$^+$ (ES$^+$);
$^1$H NMR δ 2.10 (3H, s), 2.16 (1H, dd), 2.37-2.43 (1H, m), 2.52-2.58 (1H, m), 3.12-3.15 (4H, m), 3.43-3.46 (4H, m), 3.68 (1H, dd), 3.74-3.79 (2H, m), 4.05 (1H, dd), 4.58 (2H, dd), 6.76 (2H, br s), 6.86 (1H, br s), 7.00 (1H, td), 7.05 (2H, d), 7.26-7.34 (2H, m), 7.77 (1H, s), 7.93 (1H, dd), 7.97 (2H, d), 8.23 (1H, dd), 8.34 (1H, s), 8.42 (1H, dd), 10.66 (1H, s).

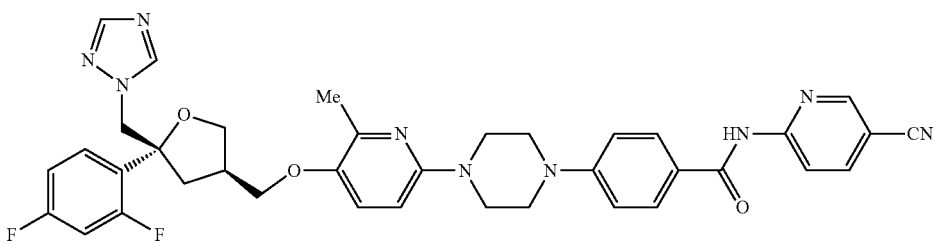

42

4-(4-(4-(((3R,5R)-5-((1H-1,2,4-triazol-1-yl)methyl)-5-(2,4-difluorophenyl)tetrahydrofuran-3-yl)methoxy)6-methylpyridin-2-yl)piperazin-1-yl)-N-(5-cyanopyridin-2-yl)benzamide.
Purified by column chromatography (SiO$_2$, 0-10% MeOH in DCM, gradient elution);
R$^r$ 2.18 min (Method a); m/z 692 (M + H)$^+$ (ES$^+$);
$^1$H NMR δ: 2.15 (1H, dd), 2.24 (3H, s), 2.37-2.43 (1H, m), 2.52-2.57 (1H, m), 3.44-3.50 (8H, m), 3.68 (1H, dd), 3.74-3.78 (2H, m), 4.04 (1H, dd), 4.58 (2H, dd), 6.67 (1H, d), 6.97-7.06 (3H, m), 7.21 (1H, d), 7.25-7.34 (2H, m), 7.77 (1H, s), 7.99 (2H, d), 8.26 (1H, dd), 8.34-8.36 (2H, m), 8.84 (1H, dd), 10.98 (1H, s).

TABLE 2-continued

Additional Compound Examples of the Invention

Example No., Structure, Name, Purification Method and Analytical and Spectral Data

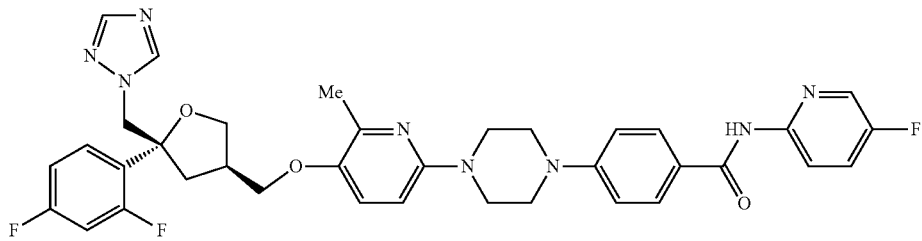

43

4-(4-(4-(((3R,5R)-5-((1H-1,2,4-triazol-1-yl)methyl)-5-(2,4-difluorophenyl)tetrahydrofuran-3-yl)methoxy)-6-methylpyridin-2-yl)piperazin-1-yl)-N-(5-fluoropyridin-2-yl)benzamide.
Purified by column chromatography (SiO$_2$, 0-10% MeOH in DCM, gradient elution);
R$^t$ 2.16 min (Method a); m/z 685 (M + H)$^+$ (ES$^+$);
$^1$H NMR δ: 2.16 (1H, dd), 2.24 (3H, s), 2.37-2.43 (1H, m), 2.54-2.58 (1H, m), 3.41-3.43 (4H, m), 3.48-3.50 (4H, m), 3.68 (1H, dd), 3.74-3.78 (2H, m), 4.04 (1H, dd), 4.58 (2H, dd), 6.67 (1H, d), 6.97-7.05 (3H, m), 7.21 (1H, d), 7.25-7.34 (2H, m), 7.74-7.79 (2H, m), 7.97 (2H, d), 8.21 (1H, dd), 8.34 (1H, s), 8.37 (1H, d), 10.57 (1H, s).

Biological Testing: Experimental Methods

Assessment of Planktonic Fungus Growth a. Resazurin-Microtitre Assay

This assay was conducted using a modified, published method (Monteiro et al., 2012). Spores of *Aspergillus fumigatus* (NCPF2010, Public Health England, Wiltshire) were cultured in Sabouraud dextrose agar for 3 days. A stock spore suspension was prepared from a Sabouraud dextrose agar culture by washing with PBS-tween (10 mL; PBS containing 0.05% Tween-20, 100 U/mL Penicillin and 100 U/mL Streptomycin). The spore count was assessed using a Neubauer haemocytometer and, using PBS adjusted to 10$^6$ spores/mL. A working suspension of spores (10$^4$ spores/mL) was prepared in filter sterilised MOPS RPMI-1640 (50 mL; RPMI-1640 containing 2 mM L-glutamine, 2% glucose and 0.165 M MOPS, buffered to pH 7 with NaOH). Resazurin sodium salt (100 μL of 1% solution; Sigma-Aldrich, Dorset, UK) was added to the spore suspension and mixed well. The spore suspension-resazurin mixture (100 μL/well) was added to 384-well plates (Catalogue number 353962, BD Falcon, Oxford, UK).

Simultaneously, test compounds (0.5 μL DMSO solution) were added to 100 μL of the spore-resazurin mixture in quadruplicate to provide a final DMSO solution of 0.5% using an Integra VIAFLO 96 (Intergra, Zizers, Switzerland). For non-spore control wells, MOPS-RPMI-resazurin solution (100 μL) was added instead of the spore-resazurin mixture. The plate was covered with a Breathe Easier membrane (Catalogue No Z763624, Sigma-Aldrich, Dorset, UK), and incubated (35° C., 5% CO$_2$) until fluorescence in the inoculated wells was double that of the control wells (around 24 hr). The fluorescence of each well (545 nm (excitation)/590 nm (emission), gain 800, focal height 5.5 mm) was determined using a multi-scanner (Clariostar: BMG, Buckinghamshire, UK). The percentage inhibition for each well was calculated and the MIC$_{50}$, MIC$_{75}$ and MIC$_{90}$ values were calculated from the concentration-response curve generated for each test compound.

b. Broth Microdilution Assay

This assay was conducted using a modified method published by EUCAST (Rodriguez-Tudela et al., 2008). Spores of *Aspergillus fumigatus* (NCPF2010, NCPF7010 (Methionine 220 mutation), NCPF7099 (Glycine G54 mutation) from Public Health England, Wiltshire; TR34/L98H mutants from St Louis Hospital, Paris, France) were cultured in Sabouraud dextrose agar for 3 days. A stock spore suspension was prepared from a Sabouraud dextrose agar culture by washing with PBS-tween (10 mL; PBS containing 0.05% Tween-20, 100 U/mL Penicillin and 100 U/mL Streptomycin). The spore count was assessed using a Neubauer haemocytometer and then adjusted to 10$^6$ spores/mL with PBS. A working suspension of spores (2×10$^5$ spores/mL) was prepared in filter sterilised, BSA MOPS RPMI-1640 (50 mL; RPMI-1640 containing 2 mM L-glutamine, 0.5% BSA, 2% glucose, 0.165 M MOPS, buffered to pH 7 with NaOH). For the assay, BSA MOPS RPMI-1640 (50 μL/well) was added throughout the 384-well plate (Catalogue number 353962, BD Falcon, Oxford, UK) first. Test compounds (0.5 μL DMSO solution) were then added in quadruplicate using an Integra VIAFLO 96 (Integra, Zizers, Switzerland), and mixed well using a plate mixer. Subsequently 50 μL of the working spore suspension prepared above was added to all wells except non-spore control wells. For non-spore control wells, BSA MOPS-RPMI solution (50 μL/well) was added instead. The plate was covered with a plastic lid, and incubated (35° C. with ambient air) for 48 hr. The OD of each well at 530 nm was determined using a multi-scanner (Clariostar: BMG, Buckinghamshire, UK). The percentage inhibition for each well was calculated and the MIC$_{50}$, MIC$_{75}$ and MIC$_{90}$ values were calculated from the concentration-response curve generated for each test compound.

Fungus panel screening was conducted by Eurofins Panlabs Inc. The MIC and MIC$_{50}$ values of the test articles were determined following the guidelines of the Clinical and Laboratory Standards Institute, broth microdilution methods for yeast (CLSI M27-A2), (CLSI, 2002) and for filamentous fungi (CLSI M38-A), (CLSI, 2008).

*Aspergillus fumigatus* Infection of Bronchial Epithelial Cells

BEAS2B cells were seeded in 96-well plates (100 μL; 30,000 cells/well; Catalogue No 3596, Sigma Aldrich, Dorset, UK) in 10% FBS RPMI-1640 and were then incubated (37° C., 5% $CO_2$) for one day before experimentation. Test compounds (0.5 μL DMSO solution) or vehicle (DMSO) were added to each well to give a final DMSO concentration of 0.5%. BEAS2B cells were incubated with test compounds for 1 hr (37° C., 5% $CO_2$) before infection with *Aspergillus fumigatus* (20 μL; Public Health England) conidia suspension ($0.5 \times 10^6$/ml in 10% FBS RPMI-1640). The plate was incubated for 24 hr (35° C., 5% $CO_2$). Supernatant (50 μL) was collected and transferred to a PCR plate (Catalogue No L1402-9700, Starlab, Milton Keynes, UK), which was frozen (−20° C.) until use. After thawing, supernatant (5 μL) was diluted 1:20 by adding R7-PBS solution (95 μL; 1:4R7 to PBS; Bio-Rad Laboratories, Redmond, Wash., USA). GM levels in these samples (50 μL) were measured using Platelia GM-EIA kits (Bio-Rad Laboratories, Redmond, Wash., USA). The percentage inhibition for each well was calculated and the $IC_{50}$ value was calculated from the concentration-response curve generated for each test compound.

*Aspergillus fumigatus* Infection of Human Alveoli Bilayers

In vitro models of human alveoli, consisting of a bilayer of human alveolar epithelial cells and endothelial cells, were prepared as previously described (Hope et al., 2007). This system allows administration of a test compound to the upper ("air" space) and/or lower ("systemic" space) compartments. This flexibility has been exploited to explore the effects of combination treatments by dosing compound Example 1 to the upper chamber and posaconazole or other anti-fungal agents to the lower chamber. Primary human pulmonary artery endothelial cells (HPAEC) were harvested and diluted to $10^6$ cells/mL in EGM-2 media (Lonza, Basel, Switzerland). Transwells were inverted and the cell suspension (100 μL/well) was applied to the base of each transwell. The inverted transwells were incubated at RT within a flow hood for 2 hr after which they were turned upright. EGM-2 media was added to the lower (700 μL/well) and upper (100 μL/well) compartments and the transwells were incubated for 48 hr (37° C., 5% $CO_2$). The EGM-2 media in the lower compartment was then replaced with fresh EGM-2 media. A549 cells were harvested and diluted to $5 \times 10^5$ cells/mL in 10% EBM, then added to the upper compartment (100 μL/well) of all transwells and the plates incubated for 72 hr (37° C., 5% $CO_2$). Conidia of *Aspergillus fumigatus* (the itraconazole sensitive strain NCPF2010 and the itraconazole resistant strain TR34-L98H) were cultured separately in Sabouraud dextrose agar for 3 days. A stock conidia suspension of either strain was prepared from a Sabouraud dextrose agar culture by washing with PBS-tween (10 mL; PBS containing 0.05% Tween-20, 100 U/mL Penicillin and 100 U/mL Streptomycin). The conidia count was assessed using a Neubauer haemocytometer and adjusted to $10^6$ conidia/mL with PBS. A working stock of conidia was prepared in EBM (conc of $10^5$ conidia/mL) immediately prior to use.

Test and reference compounds (or neat DMSO as the vehicle) were added to the appropriate wells of 24-well plates (3 μL/well containing 600 μL of 2% FBS EBM) for lower compartment treatment and to 96-well plates (1 μL/well containing 200 μL of 2% FBS EBM) for the treatment of the upper compartment, to provide a final DMSO concentration of 0.5%. The media in the upper compartment was aspirated and that containing the appropriate test and reference compounds, or vehicle, were added (100 μL/well). Transwells were then transferred into the 24-well plate containing the test and reference compounds or DMSO vehicle. After incubation for 1 hr (35° C., 5% $CO_2$) the conidia suspension (10 μL/well) was added to the upper compartment of each transwell. Plates were then incubated for 24 hr (35° C., 5% $CO_2$). Supernatants from each compartment (5 μL/compartment) were collected and stored (−20° C.). Media was replaced daily after collection of the supernatants and all wells were treated with test and reference compounds or with DMSO, as described above, for 3 days. Samples continued to be collected until fungal growth was visible by eye in all transwells. The levels of GM in the supernatant in lower compartment were then measured by ELISA (BioRad, CA, USA) as an index of *Aspergillus fumigatus* invasion.

Cell Viability: Resazurin Assay

BEAS2B cells were seeded in 384-well plates (100 μL; 3000/well/; BD Falcon, Catalogue No 353962) in RPMI-LHC8 (RPMI-1640 and LHC8 media combined in equal proportions) one day before experimentation. For cell-free control wells, RPMI-LHC8 (100 μL) was added. Test compounds (0.5 μL of a DMSO solution) were added to give a final DMSO concentration of 0.5% using an Integra VIA-FLO 96 (Integra, Zizers, Switzerland). BEAS2B cells were incubated with each test compound for 1 day (37° C./5% $CO_2$ in RPMI-LHC8). After addition of resazurin stock solution (5 μL, 0.04%) the plates were incubated for a further 4 hr (37° C./5% $CO_2$). The fluorescence of each well at 545 nm (excitation) and 590 nm (emission) was determined using a multi-scanner (Clariostar: BMG Labtech). The percentage loss of cell viability was calculated for each well relative to vehicle (0.5% DMSO) treatment. Where appropriate, a $CC_{50}$ value was calculated from the concentration-response curve generated from the concentration-response curve for each test compound.

In Vivo Anti-Fungal Activity

*Aspergillus fumigatus* (ATCC 13073 [strain: NIH 5233], American Type Culture Collection, Manassas, Va., USA) was grown on Malt agar (Nissui Pharmaceutical, Tokyo, Japan) plates for 6-7 days at RT (24±1° C.). Spores were aseptically dislodged from the agar plates and suspended in sterile distilled water with 0.05% Tween 80 and 0.1% agar. On the day of infection, spore counts were assessed by haemocytometer and the inoculum was adjusted to obtain a concentration of $1.67 \times 10^8$ spores $mL^{-1}$ of physiological saline.

To induce immunosuppression and neutropenia, A/J mice (males, 5 weeks old) were dosed with hydrocortisone (Sigma H4881; 125 mg/kg, sc) on days 3, 2 and 1 before infection, and with cyclophosphamide (Sigma C0768; 250 mg/kg, ip) 2 days before infection. On day 0, animals were infected with the spore suspension (35 μL intra-nasally).

Test compounds were administered intra-nasally (35 μL of a suspension of 0.08-2.00 mg/mL in physiological saline) once daily, 30 min before infection on day 0 and then on days 1, 2 and 3 (representing prophylactic treatment) or on days 1, 2 and 3 only (representing therapeutic treatment). For extended prophylactic treatment, test compounds (35 μL of a suspension of 0.0032 or 0.016 mg/mL in physiological saline) were administered intra-nasally once daily for seven days; then 30 min before infection on day 0, and thereafter, either on days 1, 2 and 3 after infection, or on day 0 only. The effects of these treatment paradigms were compared with those obtained when treatment was restricted to one day and 30 min before inoculation and then on days 1, 2 and 3 post infection; or reduced still further to one day and 30 min before infection only. Animal body weights were monitored daily and those exhibiting a reduction ≥20%, compared with their body weight on day 0, were culled.

Six hours after the last dose, animals were anesthetised, the trachea was cannulated and BALF was collected. The total number of alveolar cells was determined using a haemocytometer, and the numbers of alveolar macrophages and neutrophils were determined by FACS analysis (EPICS® ALTRA II, Beckman Coulter, Inc., Fullerton, Calif., USA) using anti-mouse MOMA2-FITC (macrophage) or anti-mouse 7/4 (neutrophil), respectively, as previously reported (Kimura et al., 2013). The levels of IFN-γ and IL-17 in BALF, and IL-6 and TNFα in serum were determined using Quantikine® mouse IFN-γ, IL-17, IL-6 or TNF-α ELISA kit (R&D systems, Inc., Minneapolis, Minn., USA) respectively. MDA, an oxidative stress marker, was assayed using OxiSelect® TBARS Assay Kits (MDA Quantitation; Cell Biolabs Inc, San Diego, Calif., USA). *Aspergillus* GM in serum was determination using Platelia GM-EIA kits (Bio-Rad Laboratories, Redmond, Wash., USA). Cut-off index was calculated by the formula: Cut-off index=OD in sample/OD in cut-off control provided in kit. For tissue fungal load assays, 100 mg of lung tissue was removed aseptically and homogenized in 0.2 mL of 0.1% agar in sterile distilled water. Serially diluted lung homogenates were plated on Malt agar plates (50 μL/plate), and incubated at 24±1° C. for 72 to 96 h. The colonies of *A. fumigatus* on each plate was counted and the fungal titre presented as CFU per gram of lung tissue.

Severely immunosuppressed, neutropenic A/J mice (males, 5 weeks old), which had been dosed with hydrocortisone (Sigma H4881; 125 mg/kg, sc) daily for three days before infection and with cyclophosphamide (Sigma C0768; 250 mg/kg, ip) two days before infection were used to evaluate the effects of the combined treatment of compound Example (I) administered intranasally and posaconazole dosed orally. On day 0, animals were infected intranasally with 35 μL of the spore suspension (1.67×10⁸ spores/mL in physiological saline) of *Aspergillus fumigatus* (ATCC 13073 [strain: NIH 5233]). Compound Example (I), prepared as a suspension in isotonic saline (0.4 mg/mL), was dosed once daily by an intra-nasal injection (35 μL/mouse) on days 1-6 after infection. Posaconazole (1 mg/kg) was given orally once daily on days 1-6 after infection. Body weight and survival were monitored daily up to day 7.

Summary of Screening Results

The compounds of the invention, as disclosed herein, demonstrate potent inhibitory activity against infection of bronchial epithelial cells by azole sensitive *Aspergillus fumigatus* and, where tested, fungal growth, as evaluated by the resazurin assay (Table 3). With a single exception, incubation with the compounds of the invention had no or little effect on the viability of BEAS2B bronchial epithelial cells at concentrations up to, at least, 10 μM. Particularly, in these assay systems compound Example 1 showed significantly greater potency than voriconazole and amphotericin B and similar potency to posaconazole.

TABLE 3

The effects of treatment with Voriconazole, Posaconazole, Amphotericin B and the compound examples of the invention on *Aspergillus fumigatus* (NCPF2010) planktonic fungal growth, on fungal infection of BEAS2B bronchial epithelial cells and on BEAS2B cell viability.

| Treatment (Test Compound Example No.) | Planktonic fungal growth[1] $MIC_{50}$ | Planktonic fungal growth[1] $MIC_{75}$ | Infection of BEAS2B cells[2] $MIC_{50}$ | BEAS2B Cell Viability[3] $CC_{50}$ |
|---|---|---|---|---|
| Voriconazole | 90.8 | 168 | 154 | >28600 |
| Posaconazole | 3.64 | 6.94 | 4.48 | >14300 |
| Amphotericin B | 28.5 | 64.4 | nt | 977 |
| 1 | 1.98 | 5.02 | 5.43 | >12200 |
| 2 | 0.74 | 3.06 | 1.42 | >14300 |
| 3 | nt | nt | 51.7 | >14600 |
| 4 | nt | nt | 7.77 | >14400 |
| 5 | nt | nt | 123 | >14400 |
| 6 | nt | nt | 23.9 | >14600 |
| 7 | nt | nt | 12.5 | >14500 |
| 8 | nt | nt | 14.2 | 548 |
| 9 | nt | nt | 5.21 | >14500 |
| 10 | nt | nt | 14.5 | >14100 |
| 11 | nt | nt | 284 | >14200 |
| 12 | nt | nt | 97.3 | >13700 |
| 13 | 4.27 | 17.8 | 23.9 | >13400 |
| 14 | nt | nt | 8.36 | >14600 |
| 15 | nt | nt | 7.64 | >14400 |
| 16 | nt | nt | 0.82 | >14300 |
| 17 | nt | nt | nt | >14600 |
| 18 | nt | nt | 86.6 | >14200 |
| 19 | nt | nt | 17.2 | >13400 |
| 20 | nt | nt | 36.1 | >13200 |
| 21 | nt | nt | 3.86 | >13000 |
| 22 | nt | nt | 4.77 | >13400 |
| 23 | nt | nt | 3.37 | >14100 |
| 24 | nt | nt | nt | >14100 |
| 25 | nt | nt | 230 | >13400 |
| 26 | nt | nt | >1430 | >14300 |
| 27 | nt | nt | nt | >14300 |
| 28 | nt | nt | 11.7 | >14300 |
| 29 | nt | nt | 14.5 | >13900 |
| 30 | nt | nt | 1050 | >13900 |
| 31 | nt | nt | 10.7 | >13900 |
| 32 | nt | nt | 26.1 | >14400 |
| 33 | nt | nt | 43.5 | >14400 |
| 34 | nt | nt | 21.9 | >14000 |
| 35 | nt | nt | 125 | >14000 |
| 36 | nt | nt | 3.52 | >14500 |
| 37 | nt | nt | 18.8 | >14500 |
| 38 | nt | nt | 4.86 | >14100 |
| 39 | nt | nt | nt | >13300 |
| 40 | nt | nt | 6.87 | >14500 |
| 41 | nt | nt | nt | >14300 |
| 42 | nt | nt | nt | >14500 |
| 43 | nt | nt | 2.85 | >14600 |

Table Footnotes:
[1] Resazurin-microtitre assay;
[2] Bronchial epithelial cells;
[3] n = 3-5;

Furthermore, the compounds of the invention exhibit potent inhibitory activity against planktonic fungal growth as evaluated in a broth microdilution assay (Table 4). In this assay, the compounds of the invention commonly showed significantly greater potency versus the posaconazole-resistant strains (NCPF7099, NCPF7100 and TR34/L98H) as well as a posaconazole-sensitive strain (NCPF2010) than did posaconazole, voriconazole and Amphotericin B.

TABLE 4

The effects of treatment with Voriconazole, Posaconazole, Amphotericin B and the compound examples of the invention on planktonic fungal growth of isolates of *Aspergillus fumigatus*.

| Treatment (Test Compound Example No.) | MIC$_{75}$ Values (nM) against the indicted *Aspergillus fumigatus* isolates[1] | | | |
|---|---|---|---|---|
| | NCPF2010 | NCPF7099 | NCPF7100 | L98H |
| Voriconazole | 496 | 96.7 | 596 | >2860 |
| Posaconazole | 15.3 | 112 | 71.5 | 150 |
| Amphotericin B | 382 | 365 | >1080 | 209 |
| 1 | 13.6 | 16.5 | 19.7 | 56.7 |
| 2 | 7.00 | 28.3 | 21.3 | 81.6 |
| 3 | 18.0 | 27.6 | 45.1 | 33 |
| 4 | 8.68 | 41.3 | 38.3 | 73.7 |
| 5 | 13.3 | 157 | 96.6 | 162 |
| 6 | 12.5 | 21.2 | 21.4 | 131 |
| 7 | 5.86 | 14.1 | 4.07 | 41.9 |
| 8 | 12.7 | >1450 | >1450 | >1450 |
| 9 | 29.1 | 7.39 | 23.2 | 114 |
| 10 | 22.0 | 9.96 | 29.5 | 81.2 |
| 11 | 23.6 | 49.0 | 52.9 | 179 |
| 12 | 13.4 | 22.8 | 30.3 | 45.9 |
| 13 | 25.3 | 33.0 | 32.4 | 101 |
| 14 | 43.1 | 33.2 | 41.0 | 73.5 |
| 15 | 29.0 | 18.4 | 8.45 | >1440 |
| 16 | 5.12 | 9.26 | 6.58 | 33.5 |
| 17 | 2.15 | 18.5 | 13.3 | 409 |
| 18 | 22.2 | 11.0 | 47.1 | 73.3 |
| 19 | 16.6 | 8.90 | 22.7 | 57.7 |
| 20 | 18.8 | 11.1 | 14.6 | 46.1 |
| 21 | 37.4 | 21.1 | 31.7 | 51.7 |
| 22 | 11.3 | 16.4 | 22.0 | >1340 |
| 23 | 12.6 | 28.4 | 44.3 | 60.2 |
| 24 | 9.90 | 20.5 | 14.0 | 191 |
| 25 | 84.5 | 25.1 | 47.6 | 65.9 |
| 26 | 31.1 | 131 | 91.0 | 126 |
| 27 | 19.3 | 12.7 | 22.3 | 136 |
| 28 | 31.9 | 26.6 | 36.1 | 198 |
| 29 | 28.5 | 37.0 | 53.8 | 120 |
| 30 | 58.4 | 34.7 | 41.3 | 191 |
| 31 | 43.9 | 10.9 | 67.9 | 163 |
| 32 | 69.7 | 48.1 | 60.9 | 69.5 |
| 33 | 13.5 | 48.9 | 23.6 | 67.9 |
| 34 | 44.6 | 29.0 | 14.8 | 73.9 |
| 35 | 63.4 | 109 | 111 | 178 |
| 36 | 41.0 | 44.5 | 34.6 | 134 |
| 37 | 28.4 | 24.6 | 22.0 | 194 |
| 38 | 12.4 | 31.9 | 33.6 | 65.4 |
| 39 | 52.0 | nt | nt | 65.9 |
| 40 | 12.5 | 24.0 | 14.6 | 73.1 |
| 41 | 57.6 | nt | nt | 261 |
| 42 | 46.8 | 30.1 | 40.6 | 80.2 |
| 43 | 23.7 | 32.3 | 34.3 | 56.4 |

Table Footnotes:
[1] Broth microdilution assay, n = 3

The effects of compound Example 1 on the growth of wide range of fungal pathogens were evaluated using the CLSI broth microdilution methods. Compound Example 1 was found to be a potent inhibitor of the growth of *Rhizopus oryzae, Cryptococcus neoformans, Chaetomimum globosum, Penicillium chrysogenum* and *Trichophyton rubrum* as well as some *Candida* Spp (Table 5).

TABLE 5

The effects of compound Example 1 on the growth of a range of fungi species.

| Fungal Agent | Strain | Example 1 | | Voriconazole | | Posaconazole | |
|---|---|---|---|---|---|---|---|
| | | MIC$_{50}$ (µg/mL) | MIC$_{100}$ (µg/mL) | MIC$_{50}$ (µg/mL) | MIC$_{100}$ (µg/mL) | MIC$_{50}$ (µg/mL) | MIC$_{100}$ (µg/mL) |
| *Aspergillus flavus* | ATCC204304 | 1.0 | >8.0 | 1.0 | 2.0 | 0.063 | 0.13 |
| *Aspergillus pullulans* | ATCC9348 | >8.0 | >8.0 | >8.0 | >8.0 | 0.25 | 1.0 |
| *Candida albicans* | 20240.047 | 0.031 | >8.0 | 0.031 | >8.0 | 0.031 | >8.0 |
| | ATCC10231 | 0.13 | >8.0 | 0.25 | >8.0 | 0.13 | >8.0 |
| | 20183.073 | 0.5 | >8.0 | 4.0 | >8.0 | 0.25 | >8.0 |
| | 20186.025 | >8.0 | >8.0 | >8.0 | >8.0 | >8.0 | >8.0 |
| *Candida glabrata* | ATCC36583 | 0.5 | >8.0 | 0.25 | >8.0 | 0.5 | >8.0 |
| | R363 | 0.5 | >8.0 | >8.0 | >8.0 | 0.5 | >8.0 |
| *Rhizopus oryzae* | ATCC11145 | 0.063 | 2.0 | 8.0 | >8.0 | 0.13 | >8.0 |
| *Cryptococcus neoformans* | ATCC24067 | 0.008 | 1.0 | 0.016 | 1.0 | 0.016 | 0.25 |
| *Chaetomium globosum* | ATCC44699 | 0.063 | >8.0 | 0.5 | 1.0 | 0.13 | 0.25 |
| *Penicillium chrysogenum* | ATCC9480 | 0.031 | >8.0 | 1.0 | 2.0 | 0.063 | 0.13 |
| *Trichophyton rubrum* | ATCC10218 | <0.008 | 0.031 | <0.008 | 0.063 | <0.008 | 0.031 |

Table footnotes:
MIC$_{50}$/MIC$_{100}$ = concentration required for 50% and 100% inhibition of fungal growth by visual inspection (CLSI).

Monotherapy with either compound Example 1 (0.1 µg/mL in the upper chamber) or posaconazole (0.01 µg/mL in the lower chamber) inhibited GM production on day 1 in human alveoli bilayers. However, the inhibitory effects of these treatments were lost rapidly thereafter (Table 6). In contrast, combination treatment of compound Example 1 with posaconazole showed sustained inhibition of invasion post infection. Consequently, the DFB$_{50}$ for the combination treatment was 5.48 days, much longer than the values for either compound alone. This synergistic or additive effect of combination therapy was also confirmed when treatment with compound Example 1 was combined with that of intraconazole, voriconazole or caspofungin (results not shown).

TABLE 6

Effects of compound Example 1, Posaconazole and the treatment combination on *Aspergillus fumigatus* (NCPF2010) invasion into the lower chamber in human alveoli bilayers (transwells).

GM Levels in the Lower Chamber for Treatments Indicated OD value (% inhibition vs. control)I

| Treatment Day | Vehicle | Example 1[1] Upper Chamber | Posaconazole[2] Lower Chamber | Combination Treatment |
|---|---|---|---|---|
| 0 | 0 | 0 | 0 | 0 |
| 1 | 0.68 | 0.091 (86) | 0.064 (91) | 0.007 (99) |
| 2 | 1.19 | 1.15 (3.4) | 1.01 (15) | 0.011 (99) |
| 3 | 1.19 | 1.14 (3.7) | 1.14 (4.1) | 0.025 (98) |
| 4 | 1.18 | 1.13 (4.5) | 1.17 (1.1) | 0.11 (91) |
| 5 | 1.18 | 1.18 (0.3) | 1.18 (−0.6) | 0.42 (64) |
| 6 | 1.18 | 1.18 (−0.3) | 1.19 (−1.1) | 0.73 (38) |
| 7 | 1.18 | 1.16 (0.9) | 1.17 (0.3) | 1.15 (2.0) |
| 8 | 1.16 | 1.13 (2.8) | 1.15 (0.8) | 1.12 (3.7) |
| $DFB_{50}$ Values for treatments indicated | | 1.13 | 1.45 | 5.48 |

Table Footnotes:
[1]Dosed at 0.1 μg/mL;
[2]Dosed at 0.01 μg/mL;
$DFB_{50}$: Days taken to reach a fungal burden of 50% of control In addition, this combination treatment has been tested in bilayers infected with the azole resistant strain of *Aspergillus fumigatus*: TR34-L98H. (Table 7) Monotherapy with compound Example 1 (1 μg/mL) in the upper chamber or with posaconazole (0.1 μg/mL) in the lower chamber showed limited benefit. In contrast, the combination of compound Example 1 and posaconazole showed marked inhibitory effects on fungal invasion into the lower chamber. The beneficial effect of the combination treatment was observed on day 1 post infection, but disappeared after day 2.

TABLE 7

Effects of compound Example 1, Posaconazole and the treatment combination on *Aspergillus fumigatus* (TR34-L98H strain) invasion into the lower chamber in the alveolar bilayer cell system (transwells).

GM Levels in the Lower Chamber for Treatments Indicated OD value (% inhibition vs. control)I

| Treatment Day | Compound Example 1[1] Upper Chamber | Posaconazole[2] Lower Chamber | Combination Treatment |
|---|---|---|---|
| 0 | 0 | 0 | 0 |
| 1 | 0.35 | 0.039 (88) | 0.013 (96) |
| 2 | 0.99 | 1.02 (−2.7) | 0.082 (92) |
| 3 | 0.99 | 0.97 (1.7) | 0.54 (45) |
| 4 | 1.01 | 1.02 (−1.4) | 1.09 (−8.8) |
| $DFB_{50}$ Values for treatments indicated | 1.10 | 1.64 | 2.93 |

Table Footnotes:
[1]Dosed at 1 μg/mL;
[2]Dosed at 0.1 μg/mL;
$DFB_{50}$: Days taken to reach a fungal burden of 50% of control When given intranasally to immunocompromised, neutropenic mice, on day 0 and days 1-3 following inoculation (prophylactic treatment) in a head-to-head comparison, compound Example 1 showed superior effects to posaconazole on reducing body weight loss, measured over 3 days, caused by infection with *Aspergillus fumigatus*. (Table 8).

TABLE 8

Comparison of the effects of treatment with compound Example 1 and Posaconazole on the body weight loss of immunocompromised, neutropenic mice caused by infection with *Aspergillus fumigatus*.

| Drug Treatment[1] | Body weight loss caused by infection with *A. fumigatus*[2] (% Inhibition of weight loss) | | |
|---|---|---|---|
| | Day 1 | Day 2 | Day 3 |
| Vehicle plus Spores | 9.2 ± 1.5 | 14.3 ± 1.9 | 19.3 ± 1.4 |
| Posaconazole | 7.3 ± 2.0 (21) | 13.4 ± 1.9 (6) | 18.1 ± 2.0 (6) |
| Example 1 | 6.1 ± 1.8 (34) | 8.7 ± 2.5 (39) | 11.1 ± 5.6 (42) |

Table Footnotes:
[1]Dosed at 0.4 mg/mL intra-nasally;
[2]% weight loss compared with animal weight on day 0.

Figure 2:
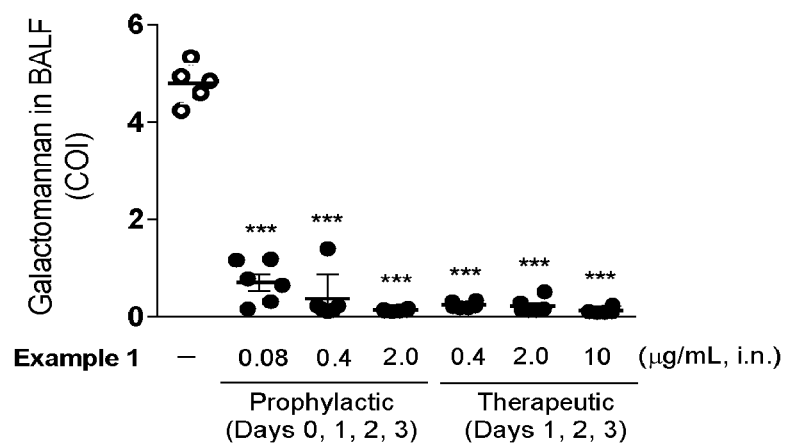
FIG. 2 and FIG. 3 show the effects of prophylactic and therapeutic treatment with compound Example 1 on galactomannan concentrations in BALF and serum respectively, in *Aspergillus fumigatus* infected, immuno-compromised, neutropenic mice.
Figure 3:
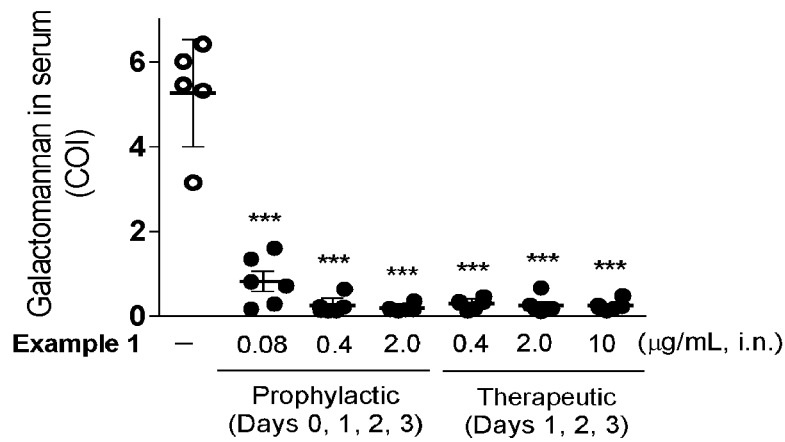

Furthermore, prophylactic and therapeutic treatment with compound Example 1 showed superior effects to posaconazole on fungal load in the lung, as well as on GM concentrations in both BALF and serum, post infection. The data for this compound, used in prophylactic and therapeutic dosing regimens, are shown in Table 9 and FIGS. 1, 2 and 3 ($ID_{50}$ values presented in Table 10).

TABLE 9

The effects of prophylactic and therapeutic treatment with compound Example 1 on CFU in lung and galactomannan concentrations in the BALF and serum of *Aspergillus fumigatus* infected, immuno-compromised, neutropenic mice.

| Treatment Regimen | Drug Conc (mg/mL) | % Inhibition of response | | |
|---|---|---|---|---|
| | | CFU (/mg of lung) | GM in BALF (COI) | GM in serum (COI) |
| Vehicle plus Spores | None | 28.4 ± 16.9 | 4.8 ± 0.40 | 5.3 ± 1.1 |
| Compound Example 1: | 0.08 | 15.2 ± 13.7 (46) | 0.70 ± 0.39 (85) | 0.81 ± 0.52 (85) |
| | 0.4 | 2.1 ± 1.6 (93) | 0.37 ± 0.46 (92) | 0.24 ± 0.18 (95) |

TABLE 9-continued

The effects of prophylactic and therapeutic treatment with compound Example 1 on CFU in lung and galactomannan concentrations in the BALF and serum of *Aspergillus fumigatus* infected, immuno-compromised, neutropenic mice.

| Treatment Regimen | Drug Conc (mg/mL) | % Inhibition of response | | |
|---|---|---|---|---|
| | | CFU (/mg of lung) | GM in BALF (COI) | GM in serum (COI) |
| Prophylactic Treatment | 2 | 0.8 ± 0.7 (97) | 0.13 ± 0.02 (97) | 0.18 ± 0.07 (97) |
| Compound Example 1: | 0.4 | 3.8 ± 1.0 (87) | 0.24 ± 0.06 (95) | 0.29 ± 0.11 (95) |
| | 2 | 1.9 ± 1.7 (93) | 0.22 ± 0.14 (95) | 0.25 ± 0.19 (95) |
| Therapeutic Treatment | 10 | 0.5 ± 0.3 (98) | 0.11 ± 0.05 (98) | 0.24 ± 0.11 (95) |

Table Footnotes:
The data for fungal load are shown as the mean ± standard error of the mean (SEM; n = 5-6).

TABLE 10

The $ID_{50}$ values for prophylactic treatment with Posaconazole and compound Example 1 on fungal load in the lung and on galactomannan concentrations in the BALF and serum, of *Aspergillus fumigatus* infected, immuno-compromised, neutropenic mice.

| Drug substance (Prophylactic Treatment) | $ID_{50}$ Values for response indicated (mg/mL) | | |
|---|---|---|---|
| | Lung Fungal Load | GM in BALF | GM in serum |
| Compound Example 1 | 0.086 | <0.08 | <0.08 |
| Posaconazole | 0.24 | 1.3 | 0.47 |

In addition, prophylactic or therapeutic treatment with certain other compounds of the invention, showed superior effects to posaconazole on fungal load in the lung, as well as on GM concentrations in both BALF and serum, post infection. The data from these studies are shown below (Tables 11 and 12).

TABLE 11

The effects of prophylactic treatment (on days 0, 1, 2 and 3) with test compounds on fungal load in the lung and galactomannan concentrations in the BALF and serum of *Aspergillus fumigatus* infected, immuno-compromised, neutropenic mice.

| Prophylactic Treatment | Drug | % Inhibition versus Infected Controls | | |
|---|---|---|---|---|
| Compound Example No. | Conc (mg/mL) | Lung Fungal Load | GM in BALF | GM in serum |
| Posaconazole | 0.4 | 44 | 20 | 34 |
| 1 | 0.4 | 81 | 92 | 95 |
| 2 | 0.4 | 25 | 43 | 27 |
| 4 | 0.4 | 85 | 84 | 90 |
| 13 | 0.4 | 18 | 49 | 32 |
| 17 | 0.4 | 83 | 45 | 72 |
| 19 | 0.4 | 62 | 16 | 30 |
| 19 | 2 | 74 | 41 | 47 |
| 23 | 0.4 | 56 | 71 | 79 |

TABLE 12

The effects of therapeutic treatment (on days 1, 2 and 3) with test compounds on fungal load in the lung and galactomannan concentrations in both BALF and serum, in *Aspergillus fumigatus* infected, immuno-compromised, neutropenic mice.

| Therapeutic Treatment | Drug | % Inhibition versus Infected Control | | |
|---|---|---|---|---|
| Compound Example No. | Conc (mg/mL) | Lung Fungal Load | GM in BALF | GM in serum |
| 1 | 0.4 | 97 | 94 | 91 |
| 3 | 0.08 | 98 | 95 | 92 |
| 3 | 0.4 | 96 | 86 | 89 |
| 16 | 0.08 | 91 | 76 | 62 |
| 16 | 0.4 | 96 | 88 | 85 |

Prophylactic treatment with compound Example 1, also inhibited inflammatory cell accumulation in BALF (Table 13), in a similar fashion to posaconazole. In addition, prophylactic treatment with compound Example 1 showed superior inhibitory effects to posaconazole versus IL-17, IFNγ and MDA concentrations in BALF, and the comparative $ID_{50}$ values for compound Example 1 and for posaconazole in independent experiments are displayed in Table 14.

TABLE 13

The effects of prophylactic and therapeutic treatment with compound Example 1 on macrophage and neutrophil accumulation into the BALF of *Aspergillus fumigatus* infected, immunocompromised, neutropenic mice.

| Treatment | Drug Conc (mg/mL) | Cell numbers in BALF ×10⁵/mL (% inhibition) | |
|---|---|---|---|
| | | Macrophage | Neutrophil |
| Vehicle plus Spores | | 0.65 ± 0.14 | 0.49 ± 0.09 |
| Compound Example 1 Prophylactic Treatment | 0.08 | 0.40 ± 0.15 (38) | 0.37 ± 0.04 (24) |
| | 0.4 | 0.32 ± 0.07 (51) | 0.26 ± 0.12 (47) |
| | 2 | 0.26 ± 0.05 (60) | 0.22 ± 0.04 (55) |

TABLE 13-continued

The effects of prophylactic and therapeutic treatment
with compound Example 1 on macrophage and neutrophil
accumulation into the BALF of Aspergillus fumigatus
infected, immunocompromised, neutropenic mice.

| Treatment | Drug Conc (mg/mL) | Cell numbers in BALF ×10$^5$/mL (% inhibition) | |
|---|---|---|---|
| | | Macrophage | Neutrophil |
| Compound Example 1 Therapeutic Treatment | 0.4 | 0.43 ± 0.05 (34) | 0.38 ± 0.04 (22) |
| | 2 | 0.40 ± 0.11 (38) | 0.34 ± 0.05 (31) |
| | 10 | 0.32 ± 0.07 (51) | 0.27 ± 0.08 (45) |

Table Footnotes:
The data for cell number are shown as the mean ± standard error of the mean (SEM), N = 5-6.

TABLE 14

The ID$_{50}$ values for prophylactic treatment with Posaconazole
and compound Example 1 on IL-17, IFNγ and MDA levels
in the BALF of Aspergillus fumigatus infected,
immuno-compromised, neutropenic mice.

| Drug substance (Prophylactic Treatment) | ID$_{50}$ Values for biomarkers indicated (mg/mL) | | |
|---|---|---|---|
| | IL-17 | IFNγ | MDA |
| Compound Example 1 | 0.074 | <0.08 | 0.11 |
| Posaconazole | 0.61 | 0.22 | 0.69 |

Furthermore, data showing the effects of compound Example 1 on IFNγ, IL-17 and MDA levels in the BALF, when administered either prophylactically or therapeutically, are shown in Table 15 and the effects on serum, IL-6 and TNFα are shown in Table 16.

TABLE 15

The effects of prophylactic and therapeutic treatment with compound
Example 1 on IFNγ, IL-17 and MDA levels in the BALF of Aspergillus fumigatus
infected, immunocompromised, neutropenic mice.

| Treatment Regimen | Drug Conc (mg/mL) | Biomarker Concentrations in BALF (% Inhibition) | | |
|---|---|---|---|---|
| | | IFNγ (pg/mL) | IL-17 (pg/mL) | MDA (μg/mL) |
| Vehicle plus Spores | | 9.2 ± 1.0 | 19.8 ± 3.6 | 1.8 ± 0.2 |
| Compound Example 1 Prophylactic Treatment | 0.08 | 3.7 ± 1.7 (60) | 9.8 ± 5.3 (51) | 0.96 ± 0.32 (47) |
| | 0.4 | 3.0 ± 0.8 (67) | 6.7 ± 4.9 (66) | 0.57 ± 0.22 (68) |
| | 2 | 2.5 ± 0.3 (73) | 3.2 ± 0.8 (84) | 0.34 ± 0.05 (81) |
| Compound Example 1 Therapeutic Treatment | 0.4 | 4.3 ± 2.2 (53) | 8.5 ± 2.9 (57) | 0.45 ± 0.10 (75) |
| | 2 | 3.3 ± 0.8 (64) | 4.0 ± 0.8 (80) | 0.37 ± 0.10 (79) |
| | 10 | 2.1 ± 0.3 (77) | 2.9 ± 0.7 (85) | 0.25 ± 0.05 (86) |

Table Footnotes:
The data for biomarker concentrations are shown as the mean ± standard error of the mean (SEM), N = 5-6.

TABLE 16

The effects of prophylactic and therapeutic treatment with compound
Example 1 on IL-6 and TNFα levels in the serum of Aspergillus fumigatus
infected, immunocompromised, neutropenic mice.

| Treatment Regimen | Drug Conc (mg/mL) | Conc of Biomarkers (pg/mL) (% Inhibition) | |
|---|---|---|---|
| | | IL-6 | TNFα |
| Vehicle plus Spores | | 284 ± 112 | 25.6 ± 8.0 |
| Compound Example 1 Prophylactic Treatment | 0.08 | 159 ± 73.3 (44) | 11.8 ± 5.9 (54) |
| | 0.4 | 86.3 ± 46.9 (70) | 7.3 ± 3.5 (71) |
| | 2 | 44.5 ± 12.2 (84) | 4.7 ± 0.4 (82) |
| Compound Example 1 Therapeutic Treatment | 0.4 | 51.7 ± 16.8 (82) | 6.2 ± 0.5 (76) |
| | 2 | 44.2 ± 11.4 (84) | 5.5 ± 0.7 (79) |
| | 10 | 35.9 ± 10.4 (87) | 4.9 ± 0.6 (81) |

Table Footnotes:
The data for biomarker concentrations are shown as the mean ± standard error of the mean (SEM), N = 5-6.

Therapeutic treatment with compound Example 1 was also found to maintain potent inhibition of lung fungal load, serum galactomannan levels and on BALF cytokine concentrations in Aspergillus fumigatus infected, immunocompromised, neutropenic mice. (Tables 8, 9, 10 and 13; and FIGS. 1, 2 and 3).

The effects of extended prophylactic dosing with compound Example 1 on biomarkers in Aspergillus fumigatus infected, immuno-compromised, neutropenic mice were also evaluated. Extended prophylaxis with the compound of Example 1 was found to inhibit fungal load in the lung, as well as the GM concentrations in both BALF and serum, at 25 fold lower doses than those used in a previous biomarker study (Table 17). Furthermore, the data suggest an accumulation of anti-fungal effects in the lung on repeat dosing since seven days of prophylaxis produced greater anti-fungal effects than did prophylactic treatment for a single added day. The compound's persistence of action in the lung is suggested by the finding that treatment on days −7 to day 0 generated superior anti-fungal effects on day 3 than those resulting from treatment on days −1 and 0, only. Nevertheless this abbreviated dosing protocol was still protective.

TABLE 17

The effects of extended prophylactic dosing of compound Example 1 on fungal load (CFU) in lung and GM concentrations in the BALF and serum of *Aspergillus fumigatus* infected, immuno-compromised, neutropenic mice.

| Treatment Regimen[1] (Days dosed) | Dose of Compound Example 1 (µg/mL) | CFU (/mg of lung) | GM in BALF (COI) | GM in Serum (COI) |
|---|---|---|---|---|
| Vehicle plus Spores[2] | None | 34.7 ± 10.7 | 5.1 ± 0.9 | 4.3 1.0 |
| −7 to +3 | 3.2 | 8.3 ± 2.0 (76) | 2.6 ± 0.36 (49) | 1.8 ± 0.43 (58) |
| −1 to +3 | 3.2 | 9.5 ± 3.3 (73) | 2.8 ± 0.71 (45) | 2.2 ± 0.69 (49) |
| −7 to +3 | 16 | 5.0 ± 2.3 (86) | 1.7 ± 0.39 (67) | 1.4 ± 0.20 (67) |
| −1 to +3 | 16 | 6.1 ± 2.8 (82) | 2.2 ± 0.61 (57) | 1.6 ± 0.41 (63) |
| −7 to 0 | 16 | 6.7 ± 1.7 (81) | 2.3 ± 0.52 (55) | 1.7 ± 0.59 (60) |
| −1, 0 | 16 | 13.1 ± 2.6 (62) | 4.5 ± 0.50 (12) | 4.0 ± 0.88 (7) |

Table Footnotes:
[1]The N value was six for all drug treated groups;
[2]The N value was five for the vehicle treated group;
[3]The data for fungal load and GM levels are shown as the mean ± standard error of the mean and the percentage inhibition, with respect to vehicle.

The influence on survival of combining the treatments of compound Example 1, dosed topically, with oral Posaconazole, was evaluated in severely immuno-compromised, neutropenic mice after inoculation with *Aspergillus fumigatus*. Monotherapy with compound Example 1 (0.4 mg/mL, given intranasally) or with Posaconazole (1.0 mg/kg, dosed orally) showed only a very limited therapeutic benefit. In contrast, the combination of compound Example 1 and Posaconazole demonstrated a marked increase on survival time following infection (Table 18).

TABLE 18

Effects of compound Example 1 and Posaconazole as monotherapy and in combination on survival in severely immune-compromised, neutropenic mice infected with *Aspergillus fumigatus*.

| Treatment Regimen | Dose (Route) | No. of survivors on day 7 (%) | Median survival (days) | Log-rank test for survival (vs. infection) |
|---|---|---|---|---|
| Vehicle | none | 0/6 (0) | 5 | — |
| Compound Example 1 | 0.4 mg/mL (in) | 0/6 (0) | 6 | p < 0.05 |
| Posaconazole | 1 mg/kg, (po) | 0/6 (0) | 6.5 | Not significant |
| Compound Example 1 plus Posaconazole | 0.4 mg/mL (in) 1 mg/kg (po) | 5/6 (83) | Undefined | p < 0.001 |

Table Footnotes:
N = 8 per group.

In Vivo Pharmacokinetics

It is a commonly used procedure for pulmonary, therapeutic agents to be dosed into the lungs of animals, for example mice, and plasma collected at various time points after dosing in order to characterise the resulting systemic exposure to the administered compound. The compound of the invention may be tested in such in vivo systems.

Summary of the Biological Profile of the Compound Examples of the Invention

The compound examples of the invention disclosed herein have been found to be potent inhibitors of bronchial epithelial cell infection by *Aspergillus fumigatus* and of planktonic growth. The compounds of the invention also inhibited the growth of posaconazole-resistant and voriconazole-resistant *Aspergillus fumigatus* isolates, commonly demonstrating greater potency than posaconazole, voriconazole and intraconazole against these strains. In vivo, in *Aspergillus fumigatus* infected, immunocompromised, neutropenic mice, compounds of the invention, demonstrated potent inhibition of *Aspergillus fumigatus* infection, whether dosed prophylactically or therapeutically. In particular compound Example 1 demonstrated potent inhibition of *Aspergillus fumigatus* infection-associated lung immune responses whether dosed prophylactically or as a treatment. In addition, compound Example 1 was highly efficacious in reducing infection-dependent body weight loss. These inhibitory effects were superior to those of posaconazole. It is significant that the beneficial anti-fungal effects of the compound of Example 1 and the compounds of the invention generally are observed in both a prophylactic and a therapeutic dosing setting.

REFERENCES

Agbetile, J., Fairs, A., Desai, D., Hargadon, B., Bourne, M., Mutalithas, K., Edwards, R., Morley, J. P., Monteiro, W. R., Kulkarni, N. S., Green, R H, Pavord, I. D., Bradding, P., Brightling, C. E., Wardlaw, A. J. and Pashley, C. H. Isolation of filamentous fungi from sputum in asthma is associated with reduced post-bronchodilator FEV1. *Clin. Exp. Allergy,* 2012, 42, 782-91.

Bafadhel M., McKenna S., Aqbetile J., Fairs A., Desai D., Mistry V., Morley J. P., Pancholi M., Pavord I. D., Wardlaw A. J., Pashley C. H. and Brightling C. E. *Aspergillus fumigatus* during stable state and exacerbations of COPD. *Eur. Respir. J.,* 2014, 43, 64-71.

Bowyer P. and Denning D. W. Environmental fungicides and triazole resistance in *Aspergillus*. *Pest Management Science,* 2014, 70, 173-178.

Chishimba L., Niven R. M., Fom M., Cooley J. and Denning D. W. Voriconazole and Posaconazole Improve Asthma Severity in Allergic Bronchopulmonary Aspergillosis and Severe Asthma with Fungal Sensitization. *Pharmacotherapy,* 2012, 49, 423-433.

Chotirmall S. H., O'Donoghue E., Bennett K., Gunaratnam C., O'Neill S. J. and McElvaney N. G. Sputum *Candida albicans* presages $FEV_1$ decline and hospital-treated exacerbations in cystic fibrosis. *Chest,* 2010, 138, 1186-95.

CLSI M27-A2: Reference method for broth dilution antifungal susceptibility testing of yeasts; Approved standard, 2nd ed, NCCLS document M27-A2, Clinical and Laboratory Standards Institute, Wayne, Pa., 2002.

CLSI M38-A2: Reference method for broth dilution antifungal susceptibility testing of filamentous fungi; Approved standard, 2nd ed, CLSI document M38-A2, Clinical and Laboratory Standards Institute, Wayne, Pa., 2008.

Denning D. W., Pleuvry A. and Cole D. C. Global burden of chronic pulmonary aspergillosis as a sequel to pulmonary tuberculosis. *Bulletin of the World Health Organization,* 2011a, 89, 864-872.

Denning D. W., Park S., Lass-Flori C., Fraczek M. G., Kirwan M., Gore R., Smith J., Bueid A., Moore C. B., Bowyer P. and Perlin D. S. High frequency triazole resistance found in nonculturable *Aspergillus fumigatus* from lungs of patients with chronic fungal disease. *Clin. Infect. Dis.,* 2011b, 52, 1123-1129.

Dimopoulos G., Frantzeskaki F., Poulakou G. and Armaganidis A. Invasive aspergillosis in the intensive care unit. *Ann. NY Acad. Sci.,* 2012, 1272, 31-39.

Geist M. J. P., Egerer G., Burhenne J., Riedel K-D. and Mikus G. Induction of voriconazole metabolism by rifampin in a patient with acute myeloid leukemia: importance of interdisciplinary communication to prevent treatment errors with complex medications. *Antimicrob. Agents Chemother.,* 2007, 51, 3455-3456.

Hope W. W., Kruhlak M. J., Lyman C. A., Petraitiene R., Petraitis V., Francesconi A., Kasai M., Mickiene D., Sein T., Peter J., Keleher A. M., Hughes J. E., Cotton M. P., Cotten C. J., Becher J., Tripathi S., Bermudez L., Maugel T. K., Zerfas P. M., Wingard J. R., Drusano G. L. and Walsh T. J. Pathogenesis of *Aspergillus fumigatus* and the kinetics of galactomannan in an in vitro model of early invasive pulmonary aspergillosis: implications for antifungal therapy. *J. Infect. Dis.,* 2007, 195(3), 455-466.

Jeong S., Nguyen P. D. and Desta Z. Comprehensive in vitro analysis of voriconazole inhibition of eight cytochrome P450 (CYP) enzymes: major effect on CYPs 2B6, 2C9, 2C19, and 3A. *Antimcrob. Agents Chemother.,* 2009, 53, 541-551.

Kaur S. and Singh S. Biofilm formation by *Aspergillus fumigatus*. *Med. Mycol.,* 2014, 52, 2-9.

Kimura G., Ueda K., Eto S., Watanabe Y., Masuko T., Kusama T., Barnes P. J., Ito K. and Kizawa Y. Toll-like receptor 3 stimulation causes corticosteroid-refractory airway neutrophilia and hyper-responsiveness in mice. *Chest.* 2013, 144, 99-105.

Lat A. and Thompson G. R. Update on the optimal use of voriconazole for invasive fungal infections. *Infect. Drug Resist.,* 2011, 4, 43-53.

Limper A. H., Knox K. S., Sarosi G. A., Ampel N. M., Bennett J. E., Catanzaro A., Davies S. F., Dismukes W. E., Hage C. A., Marr K. A., Mody C. H., Perfect J. R. and Stevens D. A. An Official American Thoracic Society Statement: Treatment of Fungal Infections in Adult Pulmonary and Critical Care Patients. *Am. J. Respir. Crit. Care Med.,* 2011, 183, 96-128.

Levin M-D., den Hollander J. G., van der Holt B., Rijnders B. J., van Vliet M., Sonneveld P. and van Schaik R. H. Hepatotoxicity of oral and intravenous voriconazole in relation to cytochrome P450 polymorphisms. *J. Antimicrob. Chemother.,* 2007, 60, 1104-1107.

Lin S-J, Scranz J and Teutsch S. M. *Aspergillus* case-fatality rate: systematic review of the literature. *Clin. Infect. Dis.,* 2001, 32, 358-366.

Monteiro M. C., de la Cruz M, Cantizani J., Moreno C., Tormo J. R., Mellado E, De Lucas J. R., Asensio F., Valiante V., Brakhage A. A., Latgé J P, Genilloud O., Vicente F. A new approach to drug discovery: high-throughput screening of microbial natural extracts against *Aspergillus fumigatus* using resazurin. *J. Biomol. Screen.* 2012, 17, 542-549.

Pasqualotto A. C., Powell G., Niven R. and Denning D. W. The effects of antifungal therapy on severe asthma with fungal sensitization and allergic bronchopulmonary aspergillosis. *Respirology,* 2009, 14, 1121-127.

Pierce C. G., Uppuluri P., Tristan A. R., Wormley F. L. Jr., Mowat E., Ramage G., Lopez-Ribot J. L. A simple and reproducible 96-well plate-based method for the formation of fungal biofilms and its application to antifungal susceptibility testing. *Nat. Protoc.,* 2008, 3, 1494-500.

Rankin, N. Disseminated aspergillosis and moniliasis associated with granulocytosis and antibiotic therapy. *Br. Med. J.,* 1953, 183, 918-9.

Rodriguez-Tudela J. L., Arendrup M. C., Arikan S., Barchiesi F., Bille J., Chyssanthou E., Cuenca-Estrella M., Dannaoui E., Denning D. W., Donnelly J. P., Fegeler W., Lass-Flörl C., Moore C., Richardson M., Gaustad P., Schmalreck A., Velegraki A. and Verweij P. Subcommittee of Antifungal Susceptibility Testing (AFST) of the ESCMID European Committee for Antimicrobial Susceptibility testing (EUCAST). EUCAST DEFINITIVE DOCUMENT E.DEF 9.1: Method for the determination of broth dilution minimum inhibitory concentrations of antifungal agents for conidia forming moulds. E.DEF 9.1 2008, 1-13.

Salmeron G., Porcher R., Bergeron A., Robin M., Peffault de Latour R., Ferry C., Rocha V., Petropoulou A., Xhaard A., Lacroix C., Sulahian A., Socié G., and Ribaud P. Persistent poor long-term prognosis of alogeneic hematopoietic stem cell transplant recipients surviving invasive aspergllosis. *Haematolologica,* 2012, 97, 1357-1363.

Thompson G. R. and Patterson T. F. Pulmonary aspergillosis. *Seminars in Respiratory and Critical Care Medicine,* 2008, 29, 103-110.

Wexler D., Courtney R., Richards W., Banfield C., Lim J. and Laughlin M. Effect of posaconazole on cytochrome P450 enzymes: a randomized, open-label two-way crossover study. *Eur. J. Pharm. Sci.,* 2004, 21, 65-653.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

The invention claimed is:

1. An aqueous suspension formulation comprising a compound of formula (I):

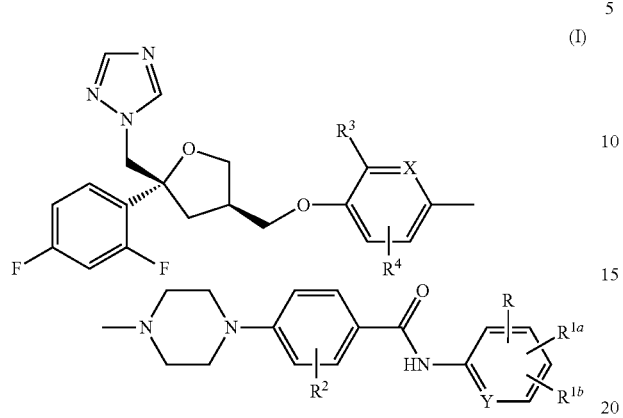

wherein:
R represents hydrogen, halo, cyano, $C_{1-4}$ haloalkyl, $C_{1-4}$ haloalkoxy, or $SO_2NR^5R^6$;
$R^{1a}$ and $R^{1b}$ independently represent hydrogen or halo;
$R^2$ represents hydrogen, halo, cyano, $C_{1-4}$ alkyl, $C_{1-4}$ alkoxy or $C_{1-4}$ haloalkoxy;
$R^3$ represents halo, cyano, $C_{1-4}$ alkyl, or $C_{1-4}$ hydroxyalkyl;
$R^4$ represents hydrogen or $C_{1-4}$ alkyl;
X represents CH or N;
Y represents CH which carbon atom may optionally be substituted by R, $R^{1a}$ or $R^{1b}$, or N;
$R^5$ and $R^6$ independently represent hydrogen or $C_{1-4}$ alkyl;
or a pharmaceutically acceptable salt thereof.

2. The aqueous suspension according to claim 1 wherein R represents H, F, CN, $OCHF_2$, $OCF_3$, $SO_2NH_2$, $SO_2NHMe$, $SO_2NMe_2$ or Cl.

3. The aqueous suspension according to claim 1 wherein $R^{1a}$ represents H, F or Cl, and $R^{1b}$ represents H or F.

4. The aqueous suspension according to claim 1 wherein $R^2$ represents H, Me or OMe.

5. The aqueous suspension according to claim 1 wherein $R^3$ represents Me, CN, Cl, $CH_2OH$ or F.

6. The aqueous suspension according to claim 1 wherein $R^4$ represents H or Me.

7. The aqueous suspension according to claim 1 wherein X represents CH or N, and wherein Y represents CH.

8. The aqueous suspension according to claim 1, wherein the compound of formula (I) is selected from:
4-(4-(4-(((3R,5R)-5-((1H-1,2,4-triazol-1-yl)methyl)-5-(2,4-difluorophenyl)tetrahydrofuran-3-yl) methoxy)-3-methylphenyl)piperazin-1-yl)-N-(4-fluorophenyl)benzamide;
4-(4-(4-(((3R,5R)-5-((1H-1,2,4-triazol-1-yl)methyl)-5-(2,4-difluorophenyl)tetrahydrofuran-3-yl) methoxy)-3-methylphenyl)piperazin-1-yl)-N-(2,4-difluorophenyl)benzamide;
4-(4-(5-(((3R,5R)-5-((1H-1,2,4-triazol-1-yl)methyl)-5-(2,4-difluorophenyl)tetrahydrofuran-3-yl) methoxy)-6-methylpyridin-2-yl)piperazin-1-yl)-N-(4-fluorophenyl)benzamide;
4-(4-(4-(((3R,5R)-5-((1H-1,2,4-triazol-1-yl)methyl)-5-(2,4-difluorophenyl)tetrahydrofuran-3-yl) methoxy)-3-cyanophenyl)piperazin-1-yl)-N-(4-fluorophenyl)benzamide;
4-(4-(4-(((3R,5R)-5-((1H-1,2,4-triazol-1-yl)methyl)-5-(2,4-difluorophenyl)tetrahydrofuran-3-yl) methoxy)-2,5-dimethylphenyl)piperazin-1-yl)-N-(4-fluorophenyl)benzamide;
4-(4-(4-(((3R,5R)-5-((1H-1,2,4-triazol-1-yl)methyl)-5-(2,4-difluorophenyl)tetrahydrofuran-3-yl) methoxy)-3-methylphenyl)piperazin-1-yl)-N-(5-fluoropyridin-2-yl)benzamide;
4-(4-(5-(((3R,5R)-5-((1H-1,2,4-triazol-1-yl)methyl)-5-(2,4-difluorophenyl)tetrahydrofuran-3-yl) methoxy)-3-methylphenyl)piperazin-1-yl)-N-(5-cyanopyridin-2-yl)benzamide;
4-(4-(4-(((3R,5R)-5-((1H-1,2,4-triazol-1-yl)methyl)-5-(2,4-difluorophenyl)tetrahydrofuran-3-yl) methoxy)-3-methylphenyl)piperazin-1-yl)-N-(3-cyanophenyl)benzamide;
4-(4-(4-(((3R,5R)-5-((1H-1,2,4-triazol-1-yl)methyl)-5-(2,4-difluorophenyl)tetrahydrofuran-3-yl) methoxy)-3-methylphenyl)piperazin-1-yl)-N-(4-cyanophenyl)benzamide;
4-(4-(4-(((3R,5R)-5-((1H-1,2,4-triazol-1-yl)methyl)-5-(2,4-difluorophenyl)tetrahydrofuran-3-yl) methoxy)-3-chlorophenyl)piperazin-1-yl)-N-(4-cyanophenyl)benzamide;
4-(4-(4-(((3R,5R)-5-((1H-1,2,4-triazol-1-yl)methyl)-5-(2,4-difluorophenyl)tetrahydrofuran-3-yl) methoxy)-3,5-dimethylphenyl)piperazin-1-yl)-N-(4-cyanophenyl)benzamide;
4-(4-(4-(((3R,5R)-5-((1H-1,2,4-triazol-1-yl)methyl)-5-(2,4-difluorophenyl)tetrahydrofuran-3-yl) methoxy)-3-methylphenyl)piperazin-1-yl)-N-(4-difluoromethoxyphenyl)benzamide;
4-(4-(5-(((3R,5R)-5-((1H-1,2,4-triazol-1-yl)methyl)-5-(2,4-difluorophenyl)tetrahydrofuran-3-yl) methoxy)-3-methylphenyl)piperazin-1-yl)-N-(4-(trifluoromethoxy)phenyl)benzamide;
4-(4-(4-(((3R,5R)-5-((1H-1,2,4-triazol-1-yl)methyl)-5-(2,4-difluorophenyl)tetrahydrofuran-3-yl) methoxy)3-methylphenyl)piperazin-1-yl)-N-(3-fluorophenyl)benzamide;
4-(4-(4-(((3R,5R)-5-((1H-1,2,4-triazol-1-yl)methyl)-5-(2,4-difluorophenyl)tetrahydrofuran-3-yl) methoxy)-3,5-dimethylphenyl)piperazin-1-yl)-N-(4-fluorophenyl)benzamide;
4-(4-(4-(((3R,5R)-5-((1H-1,2,4-triazol-1-yl)methyl)-5-(2,4-difluorophenyl)tetrahydrofuran-3-yl) methoxy)-3-hydroxymethylphenyl)piperazin-1-yl)-N-(4-fluorophenyl)benzamide;
4-(4-(4-(((3R,5R)-5-((1H-1,2,4-triazol-1-yl)methyl)-5-(2,4-difluorophenyl)tetrahydrofuran-3-yl) methoxy)-3-fluorophenyl)piperazin-1-yl)-N-(4-fluorophenyl)benzamide;
4-(4-(4-(((3R,5R)-5-((1H-1,2,4-triazol-1-yl)methyl)-5-(2,4-difluorophenyl)tetrahydrofuran-3-yl) methoxy)-3-chlorophenyl)piperazin-1-yl)-N-(4-fluorophenyl)benzamide;
4-(4-(4-(((3R,5R)-5-((1H-1,2,4-triazol-1-yl)methyl)-5-(2,4-difluorophenyl)tetrahydrofuran-3-yl) methoxy)-3-methylphenyl)piperazin-1-yl)-N-(4-sulfamoylphenyl)benzamide;
4-(4-(4-(((3R,5R)-5-((1H-1,2,4-triazol-1-yl)methyl)-5-(2,4-difluorophenyl)tetrahydrofuran-3-yl) methoxy)-3-methylphenyl)piperazin-1-yl)-N-(4-(N-methylsulfamoyl)phenyl)benzamide;

4-(4-(4-(((3R,5R)-5-((1H-1,2,4-triazol-1-yl)methyl)-5-(2,4-difluorophenyl)tetrahydrofuran-3-yl)methoxy)3-methylphenyl)piperazin-1-yl)-N-(4-(N,N-dimethylsulfamoylphenyl)benzamide;

4-(4-(4-(((3R,5R)-5-((1H-1,2,4-triazol-1-yl)methyl)-5-(2,4-difluorophenyl)tetrahydrofuran-3-yl) methoxy)-3-fluorophenyl)piperazin-1-yl)-N-(4-sulfamoylphenyl)benzamide;

4-(4-(4-(((3R,5R)-5-((1H-1,2,4-triazol-1-yl)methyl)-5-(2,4-difluorophenyl)tetrahydrofuran-3-yl) methoxy)-3-methylphenyl)piperazin-1-yl)-N-(4-cyano-2-fluorophenyl)benzamide;

4-(4-(4-(((3R,5R)-5-((1H-1,2,4-triazol-1-yl)methyl)-5-(2,4-difluorophenyl)tetrahydrofuran-3-yl) methoxy)3-fluorophenyl)piperazin-1-yl)-N-(4-cyano-2-fluorophenyl)benzamide;

4-(4-(4-(((3R,5R)-5-((1H-1,2,4-triazol-1-yl)methyl)-5-(2,4-difluorophenyl)tetrahydrofuran-3-yl) methoxy)-3-methylphenyl)piperazin-1-yl)-N-(4-(difluoromethoxy)-3-fluorophenyl)benzamide;

4-(4-(4-(((3R,5R)-5-((1H-1,2,4-triazol-1-yl)methyl)-5-(2,4-difluorophenyl)tetrahydrofuran-3-yl) methoxy)-3-methylphenyl)piperazin-1-yl)-N-(2,5-difluorophenyl)benzamide;

4-(4-(4-(((3R,5R)-5-((1H-1,2,4-triazol-1-yl)methyl)-5-(2,4-difluorophenyl)tetrahydrofuran-3-yl) methoxy)-3-methylphenyl)piperazin-1-yl)-N-(3,4-difluorophenyl)benzamide;

4-(4-(4-(((3R,5R)-5-((1H-1,2,4-triazol-1-yl)methyl)-5-(2,4-difluorophenyl)tetrahydrofuran-3-yl) methoxy)3-methylphenyl)piperazin-1-yl)-N-(3,5-difluorophenyl)benzamide;

4-(4-(4-(((3R,5R)-5-((1H-1,2,4-triazol-1-yl)methyl)-5-(2,4-difluorophenyl)tetrahydrofuran-3-yl) methoxy)-3-methylphenyl)piperazin-1-yl)-N-(4-chloro-2-fluorophenyl)benzamide;

4-(4-(4-(((3R,5R)-5-((1H-1,2,4-triazol-1-yl)methyl)-5-(2,4-difluorophenyl)tetrahydrofuran-3-yl) methoxy)-3-methylphenyl)piperazin-1-yl)-N-(4-chloro-3-fluorophenyl)benzamide;

4-(4-(4-(((3R,5R)-5-((1H-1,2,4-triazol-1-yl)methyl)-5-(2,4-difluorophenyl)tetrahydrofuran-3-yl) methoxy)3-methylphenyl)piperazin-1-yl)-N-(2,4,6-trifluorophenyl)benzamide;

4-(4-(4-(((3R,5R)-5-((1H-1,2,4-triazol-1-yl)methyl)-5-(2,4-difluorophenyl)tetrahydrofuran-3-yl) methoxy)-3-methylphenyl)piperazin-1-yl)-N-(4-fluorophenyl)-3-methylbenzamide;

4-(4-(4-(((3R,5R)-5-((1H-1,2,4-triazol-1-yl)methyl)-5-(2,4-difluorophenyl)tetrahydrofuran-3-yl) methoxy)-3-methylphenyl)piperazin-1-yl)-N-(4-fluorophenyl)-2-methylbenzamide;

4-(4-(4-(((3R,5R)-5-((1H-1,2,4-triazol-1-yl)methyl)-5-(2,4-difluorophenyl)tetrahydrofuran-3-yl) methoxy)3-methylphenyl)piperazin-1-yl)-N-(4-fluorophenyl)-3-methoxybenzamide;

4-(4-(4-(((3R,5R)-5-((1H-1,2,4-triazol-1-yl)methyl)-5-(2,4-difluorophenyl)tetrahydrofuran-3-yl) methoxy)-3-methylphenyl)piperazin-1-yl)-N-(4-fluorophenyl)-2-methoxybenzamide;

4-(4-(4-(((3R,5R)-5-((1H-1,2,4-triazol-1-yl)methyl)-5-(2,4-difluorophenyl)tetrahydrofuran-3-yl) methoxy)3-methylphenyl)piperazin-1-yl)-N-(6-cyanopyridin-2-yl)benzamide;

4-(4-(4-(((3R,5R)-5-((1H-1,2,4-triazol-1-yl)methyl)-5-(2,4-difluorophenyl)tetrahydrofuran-3-yl) methoxy)-3-methylphenyl)piperazin-1-yl)-N-(4-cyanopyridin-2-yl)benzamide;

4-(4-(4-(((3R,5R)-5-((1H-1,2,4-triazol-1-yl)methyl)-5-(2,4-difluorophenyl)tetrahydrofuran-3-yl) methoxy)-3-hydroxymethylphenyl)piperazin-1-yl)-N-(5-cyanopyridin-2-yl)benzamide;

4-(4-(4-(((3R,5R)-5-((1H-1,2,4-triazol-1-yl)methyl)-5-(2,4-difluorophenyl)tetrahydrofuran-3-yl) methoxy)-3-methylphenyl)piperazin-1-yl)-N-(5-(trifluoromethoxy)pyridin-2-yl)benzamide;

4-(4-(4-(((3R,5R)-5-((1H-1,2,4-triazol-1-yl)methyl)-5-(2,4-difluorophenyl)tetrahydrofuran-3-yl) methoxy)-3-fluorophenyl)piperazin-1-yl)-N-(5-fluoropyridin-2-yl)benzamide;

4-(4-(4-(((3R,5R)-5-((1H-1,2,4-triazol-1-yl)methyl)-5-(2,4-difluorophenyl)tetrahydrofuran-3-yl) methoxy)-3-methylphenyl)piperazin-1-yl)-N-(5-chloropyridin-2-yl)benzamide;

4-(4-(4-(((3R,5R)-5-((1H-1,2,4-triazol-1-yl)methyl)-5-(2,4-difluorophenyl)tetrahydrofuran-3-yl) methoxy)6-methylpyridin-2-yl)piperazin-1-yl)-N-(5-cyanopyridin-2-yl)benzamide; and 4-(4-(4-(((3R,5R)-5-((1H-1,2,4-triazol-1-yl)methyl)-5-(2,4-difluorophenyl)tetrahydrofuran-3-yl) methoxy)-6-methylpyridin-2-yl)piperazin-1-yl)-N-(5-fluoropyridin-2-yl)benzamide;

and pharmaceutically acceptable salts thereof.

9. A method of treatment of a subject with a mycosis or a method of prevention or treatment of disease associated with a mycosis in a subject which comprises administering to said subject an effective amount of an aqueous suspension according to claim 1.

10. The method according to claim 9 wherein the mycosis is caused by *Aspergillus* spp.

11. The method according to claim 10 wherein the *Aspergillus* spp. is an azole resistant strain of *Aspergillus fumigatus*.

12. The method according to claim 9 wherein the mycosis is caused by *Candida* spp., *Rhizopus* spp., *Cryptococcus* spp., *Chaetomium* spp., *Penicillium* spp., or *Trichophyton* spp.

13. The aqueous suspension according to claim 1 which further comprises one or more excipients selected from the group consisting of buffers, tonicity adjusting agents, pH adjusting agents, viscosity modifiers, surfactants and co-solvents.

14. The aqueous suspension according to claim 1 wherein the compound of formula (I) is in finely divided form.

15. The aqueous suspension according to claim 14 wherein the compound of formula (I) in finely divided form has a $D_{50}$ of 0.5-10 μm.

16. The aqueous suspension according to claim 1 which is intended for topical administration to the nose or lung.

17. The aqueous suspension according to claim 1 which comprises a second or further active ingredient.

18. The aqueous suspension according to claim 17 wherein the second or further active ingredient is selected from anti-fungal agents, amphotericin B, an echinocandin and an inhibitor of 3-hydroxy-3-methyl-glutaryl-CoA reductase.

19. The aqueous suspension according to claim 17 wherein the second or further active ingredient is selected from candicidin, filipin, hamycin, natamycin, nystatin, rimocidin, bifonazole, butoconazole, clotrimazole, econazole, fenticonazole, isoconazole, ketoconazole, luliconazole, miconazole, omoconazole, oxiconazole, sertaconazole, sulconazole, tioconazole, albaconazole, efinaconazole, epoxiconazole, fluconazole, isavuconazole, itraconazole, propiconazole, ravuconazole, terconazole, abafungin, amorolfin, butenafine, naftifine, terbinafine, anidulafungin, micafungin, benzoic acid, ciclopirox, flucytosine (5-fluorocytosine), griseofulvin, tolnaftate and undecylenic acid.

20. A kit of parts comprising the aqueous suspension according to claim 1 optionally in combination with one or more excipients, and instructions for the administration of the aqueous suspension to a subject in need thereof, wherein the one or more excipients is selected from the group consisting of buffers, tonicity adjusting agents, pH adjusting agents, viscosity modifiers, surfactants and co-solvents.

* * * * *